US008142789B2

(12) United States Patent
Leenhouts et al.

(10) Patent No.: US 8,142,789 B2
(45) Date of Patent: Mar. 27, 2012

(54) METHOD FOR SELECTING AND PRODUCING VACCINE COMPONENTS AND VACCINES BASED THEREON

(75) Inventors: Cornelis Johannes Leenhouts, Haren (NL); Ronald de Groot, Rotterdam (NL); Peter Wilhelmus Maria Hermans, Oud Beijerland (NL)

(73) Assignee: Mucosis B.V., AG Groningen (NL)

( * ) Notice: Subject to any disclaimer, the term of this patent is extended or adjusted under 35 U.S.C. 154(b) by 1491 days.

(21) Appl. No.: 10/556,733

(22) PCT Filed: May 17, 2004

(86) PCT No.: PCT/NL2004/000338
§ 371 (c)(1),
(2), (4) Date: Aug. 4, 2006

(87) PCT Pub. No.: WO2004/102199
PCT Pub. Date: Nov. 25, 2004

(65) Prior Publication Data
US 2007/0082003 A1 Apr. 12, 2007

(30) Foreign Application Priority Data
May 16, 2003 (EP) .................................... 03076492

(51) Int. Cl.
*A61K 39/02* (2006.01)
(52) U.S. Cl. .................................................. 424/190.1
(58) Field of Classification Search .................. None
See application file for complete search history.

(56) References Cited

U.S. PATENT DOCUMENTS
5,976,542 A 11/1999 Weiser et al.
7,541,039 B2 * 6/2009 Leenhouts et al. ......... 424/234.1

FOREIGN PATENT DOCUMENTS
EP 1 075 841 A1 2/2001
WO WO 02/077021 A2 10/2002

OTHER PUBLICATIONS

Tettelin et al. (Science vol. 293, pp. 498-506, Jul. 20, 2001).*
Zhang, et al., "Immune Responses to Novel Pneumococcal Proteins Pneumolysin, PspA, PsaA, and CbpA in Adenoidal B Cells from Children", *Infection and Immunity*, Oct. 2002, 70(10):5363-5369.
De, et al., "Purification and characterization of *Streptococcus pneumoniae* palmitoylated pneumococcal surface adhesin A expressed in *Escherichia coli*", Vaccine, 2000, 18:1811-1821.
Hoskins, et al., "Genome of the Bacterium *Streptococcus pneumoniae* Strain R6", *Journal of Bacteriology*, Oct. 2001, 183(19):5709-5717.
Tettelin, et al., "Complete Genome Sequence of a Virulent Isolate of *Streptococcus pneumoniae*", *Science*, Jul. 2001, 293:498-506.
Zysk, et al., "Detection of 23 Immunogenic Pneumococcal Proteins Using Convalescent-Phase Serum", Infection and Immunity, 2000, 68(6):3740-3743.
Wizemann, et al., "Use of Whole Genome Approach to Identify Vaccine Molecules Affording Protection against *Streptococcus pneumoniae* Infection", Infection and Immunity, 2001, 69(3):1593-1598.
Overweg, et al., "The Putative Proteinase Maturation Protein A of *Streptococcus pneumoniae* Is a Conserved Surface Protein with Potential to Elicit Protective Immune Responses", Infection and Immunity, 2000, 68(7):4180-4188.
Bogaert, et al., "Multiplex opsonophagocytosis assay (MOPA): a useful tool for the monitoring of the 7-valent pneumococcal conjugate vaccine", Vaccine, 2004, 22:4014-4020.
Darkes et al., "Pneumococcal Conjugate Vaccine (PrevnarTM1; PNCRM7) A Review of its Use in the Prevention of *Sreptococcus pneumoniae* Infection," Pediatr Drugs 2002; 4 (9); 609-630.
Klugman, "Efficacy of pneumococcal conjugate vaccines and their effect on carriage and antimicrobial resistance," The Lancet Infectious Diseases vol. 1 Sep. 2001 85-91.
Lee et al., "Development and Evaluation of Pneumococcal Conjugate Vaccines: Clinical Trials and Control Tests," Critical Reviews in Microbiology 28(1):27-41 2002.
McCool et al., "The Immune Response to Pneumococcal Proteins during Experimental Human Carriage," J. Exp. Med. vol. 195 (3) Feb. 2002 359-365.
Obaro, "The new pneumococcal vaccine," European Soeicty of Clinical Microbiology and Infectious Diseases CMI 8 2002 623-633.
Overweg et al., "Differential Protein Expression in Phenotypic Variants of *Streptococcus pneumoniae*," Infection and Immunity Aug. 2000 4604-4610.
Overweg et al., "The Putative Proteinase Maturation Protein a of *Streptococcus pneumoniae* Is a Conserved Surface Protein with Potential to Elicit Protective Immune Responses," Infection and Immunity Jul. 2000 4180-4188.

(Continued)

*Primary Examiner* — Gary Nickol
*Assistant Examiner* — Khatol Shahnan-Shah
(74) *Attorney, Agent, or Firm* — Hoffmann & Baron, LLP

(57) ABSTRACT

The invention relates to the field of biology, more specifically to the field of immunology and microbiology. The invention further relates to the field of vaccines against microbial infections and especially bacterial vaccines, in particular to pneumococcal vaccines. More in particular, the invention relates to means and methods to identify, select and isolate a vaccine component for passive and/or active immunisation against a microorganism that can be killed by opsonophagocytic cells. The invention relates to a method to identify an opsonophagocytosis inducing antigen as a vaccine component for immunisation against a microorganism. The invention describes three pneumococcal proteins SlrA, IgA1 proteinase, and PsaA, and their use as a vaccine component with or without PpmA. The invention also discloses the use of antibodies against said proteins for passive immunization and diagnosis.

13 Claims, 17 Drawing Sheets

OTHER PUBLICATIONS

Rapola et al., "Antibody response tot he pneumococcal proteins pneumococcal surface adhesin A and pneumolysin in children with acute otitis media," The Pediatric Infectious Disease Journal vol. 20 No. 5 2001 482-487.

Rapola et al., "Natural Development of Antibodies to Pneumococcal Surface Protein A, Pneumococcal Surface Adhesin A, and Pneumolysin in Relation to Pneumococcal Carriage and Acute Otitis Media," The Journal of Infectious Diseases 2000 182: 1146-1152.

Wuorimaa et al., "Current State of Pneumococcal Vaccines," Scandinavian Journal of Immunology 56 111-129, 2002.

Zysk et al., "Immune Response to Capsular Polysaccharide and Surface Proteins of *Streptococcus pneumoniae* in Patients with Invasive Pneumococcal Disease," JID 2003 187 330-333.

* cited by examiner

Fig.1 Anti-PpmA
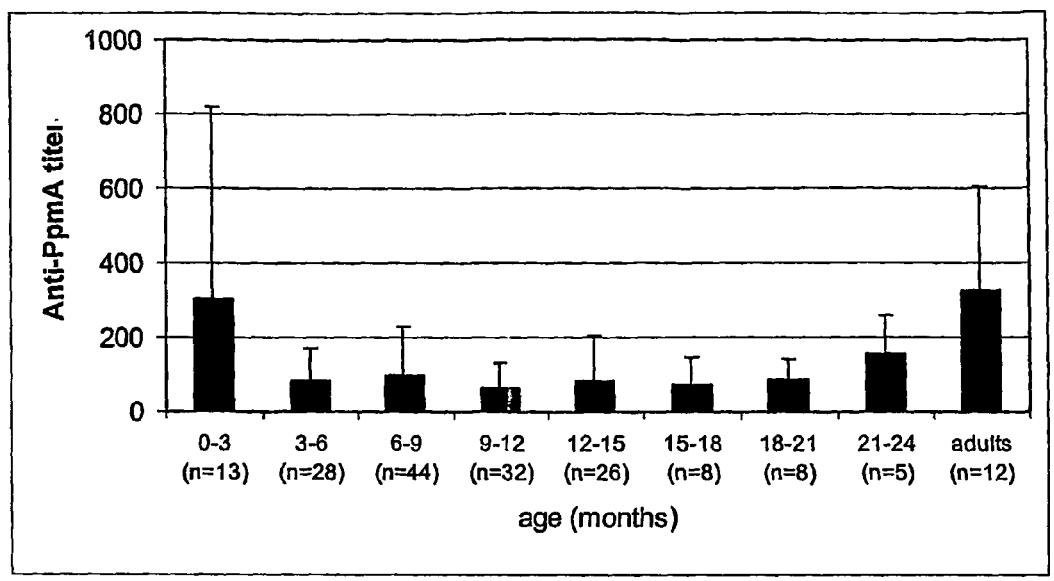
Fig. 2 Anti-Pneumolysin
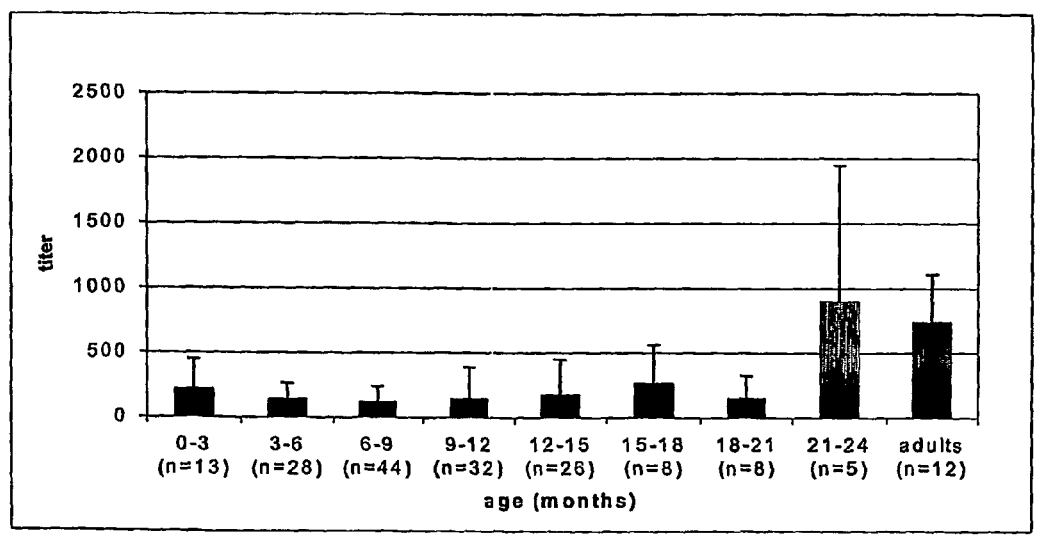

Fig. 3 Anti-IgA1 proteinase
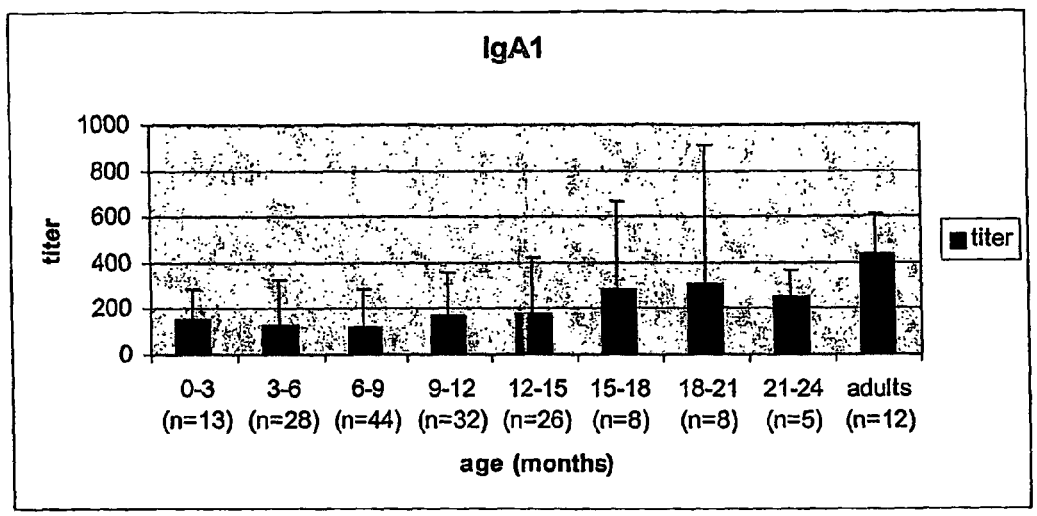
Fig. 4 Anti-α-Enolase
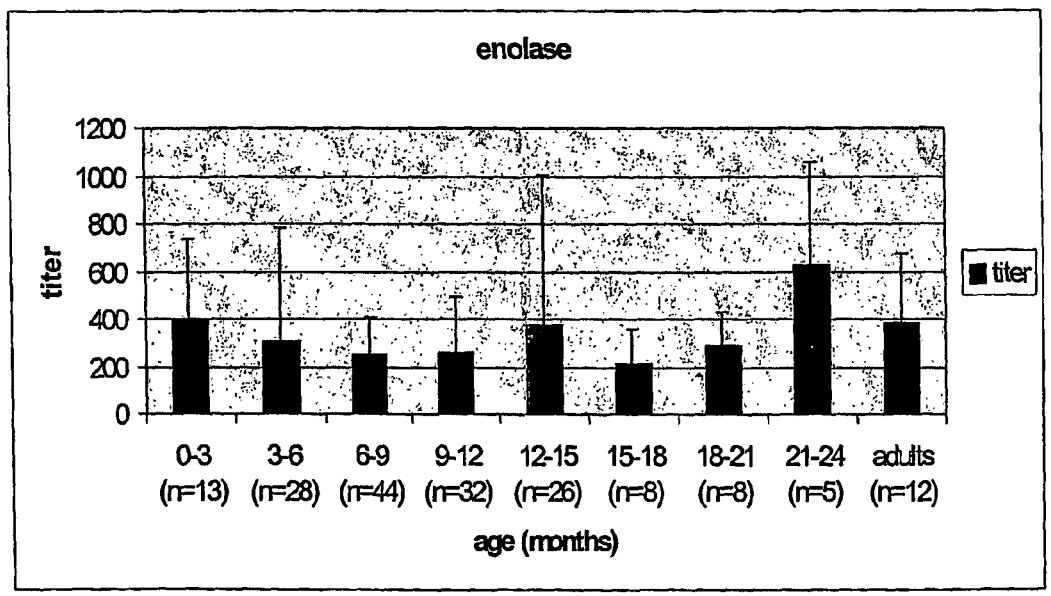

Fig. 5 Anti-SlrA
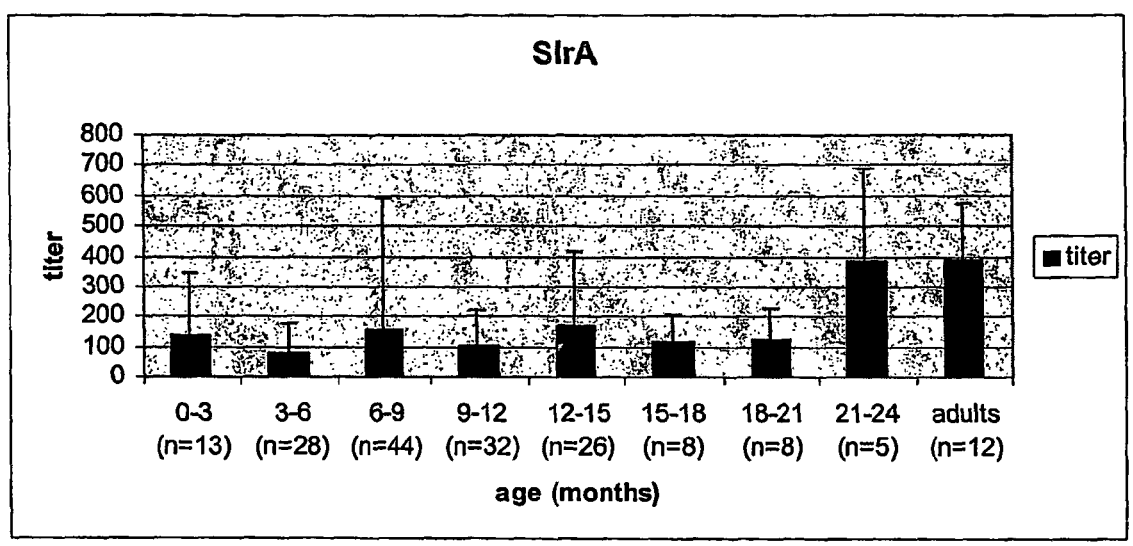

Passive immunization of CD-1 mice with pre-immune serum (PIS), Anti-PpmA serum (APS) and challenged intranasaly with S.pneumoniae D39 or a PpmA-ve knockout.

Survival of MF1 mice passively vaccinated with anti-PpmA antiserum and intranasally infected with 10-6 CFUD39

Time post challenge (h)

Fig. 12.

Product:    PpmA + PA

DTNSMSKGSEGADLISMKGDVITEHQFYEQVKSNPSAQQV
LLNMTIQKVFEKQYGSELDDKEVDDTIAEEKKQYGENYQR
VLSQAGMTLETRKAQIRTSKLVELAVKKVAEAELTDEAYK
KAFDEYTPDVTAQIIRLNNEDKAKEVLEKAKAEGADFAQL
AKDNSTDEKTKENGGEITFDSASTEVPEQVKKAAFALDVD
GVSDVITATGTQAYSSQYYIVKLTKKTEKSSNIDDYKEKL
KTVILTQKQNDSTFVQSIIGKELQAANIKVKDQAFQNIFT
QYIGGGDSSSSSSTSNEAIRAPSTSS*GNTNSGGSTTTITN
NNSGTNSSSTTYTVKSGDTLWGISQRYGISVAQIQSANNL
KS TIIYIGQKLVLTGSASSTNSGGSNNSAS TTPTTSVTPA
KPTSQTTVKVKSGDTLWALSVKYKTSIAQLKSWNHLSSDT
IYIGQNLIVSQSAAASNPSTGSGSTATNNSNSTSSNSNAS
IHKWKGDTLWGLSQKSGSPIASIKAWNHLSSDTILIGQY
LRIK* (SEQ ID NO: 57)
Molecular weight = 56229
Residues = 524

Fig 13.

**product: Igalprt + *PA***

DTNSMGQTEPEPSNGNSTEDVSTESNTSNSNGNEEIKQENE
LDPDKKVEE
PEKTLELRNVSDLELYSLSNGTYKQHISLEQVPSNPNSYFV
KVKSSSFKD
VYLPVASISEERKNDKILYKITAKVEKLQQEIESRYKDNFT
FYLAKKGTE
ETTNFTSFSNLVKAINQNPSGTYHLAASLNANEVELGPDERSYIKDTFTG
RLIGEKDGKNYAIYNLKKPLFENLSGATVEKLSLKNVAISG
KDDIGSLAN
EAQNNTKIKQVHVDGVIAGERGIGGLLAKAEOSSITESSFK
GRIINTYET
TAAYNIGGWGHLTGDKALLTKSKATVAISSNTNTSDQTVG
GLAGLVDRD
aqiqdsyaegdinnvkhfgrvagvagnlwdrtsgdvrhagslt
nvlsdvn
VTNGNAITGYHYNEMKVKDTFSSKANRVYNVTLVKDEVVSK
ESFEERGTM
LDASQIASKKAEINPLILPTVEPLSTSGICKDSDFSKVAYYQ
AKRNLTYKN
IEKLLPFYNKATIVKYGNLVNENSLLYQKELLSAVMMKDNQ
VITDIVSNK
QTANKLLLHYKDDLSEKLDLKYQNDFAKLAEYSLGNTGLLY
TPNQFLYDQ
TSIIKQVLPDLQKVDYHSEAIRKTLGISPNVKQTELYLEDQ
FAKTKQQLE
DSLKKLLSADAGLARIRAPSTSS*GNTNSGGSTTTITNNNSG*
*TN*
*SSSTTYTVKSGDTLWGISQRYGISVAQIQSANNLKSTIIYI*
*GQKLVLTGS*
*ASSTNSGGSNNSASTTPTTSVTPAKPTSQTTVKVKSGDTLW*
*ALSVKYKTS*
*IAQLKSWNHLSSDTIYIGQNLIVSQSAAASNPSTGSGSTAT*
*NNSNSTSSN*
*SNASIHKWKGDTLWGLSQKSGSPIASIKAWNHLSSDTILI*
*GQYLRIK* (SEQ ID NO: 58)

Fig 14.

**Product: SlrA + *PA***
DTNSMVQRSLRGDDY<u>VDSSLAAEES
SKVAAQSAKELNDALTNENANFPQLSKEVA
EDEAEVIFHTSQGDIRIKLFPKLAPLAVEN
FLTHAKEGYYNGITFHRVIDGFMVQTGDPK
6DGTGGQSIWHDKDKTKDK6T6FKNEITPY
LYNIRGALAMANTGQPNTNGSQFFINQNST
DTSSKLPTSKYPQKIIEAYKEGGNPSLDGK
HPVFGQVIDGMDWDKIAKAEKDEKDKPTT
AITIDSIEWKDYDFKS</u>GIRAPSTSSGNTN
*SGGSTTTITNNNSGTNSSSTTYTVKSGDTL
WGISQRYGISVAQIQSANNLKSTIIYIGQK
 LVLTGSASSTNSGGSNNSASTTPTTSVTPA
 KPTSQTTVKVKSGDTLWALSVKYKTSIAQL
KSWNHLSSDTIYIGQNLIVSQSAAASNPST
 GSGSTATNNSNSTSSNSNASIHKWKGDTL
WGLSQKSGSPIASIKAWNHLSSDTILIGQY
LRIK* (SEQ ID NO: 59)
Molecular weight - 50999 Da
Residues = 479
Isoelectric Point = 8.9172

METHOD FOR SELECTING AND PRODUCING VACCINE COMPONENTS AND VACCINES BASED THEREON

This application is the U.S. National Phase of International Application Number PCT/NL2004/000338 filed on 17 May 2004, which is incorporated herein by reference.

INCORPORATION OF SEQUENCE LISTING

Incorporated herein by reference in its entirety is the Sequence Listing for the above-identified Application. The Sequence Listing is disclosed in a computer-readable ASCII text file titled "Sequence Listing.txt," created on. The sequence.txt file is bytes in size.

The invention relates to the field of biology, more specifically to the field of immunology and microbiology. The invention further relates to the field of vaccines against microbial infections and more in particular bacterial vaccines such as pneumococcal vaccines. More in particular, the invention relates to means and methods to identify, select and isolate a vaccine component to produce a vaccine for passive and/or active immunization against a microorganism that can be recognized and preferably taken up and more preferably killed by opsonophagocytic cells.

Streptococcus pneumoniae is the leading etiological agent of severe infections such as pneumonia, septicemia, meningitis and otitis media, and causes over three million deaths per year worldwide, of which a million are children. The problem of antimicrobial resistance in Streptococcus pneumoniae has been enhanced by the successful spread of a limited number of internationally recognized multi-resistant strains. These strains have complicated the treatment of pneumococcal disease, and this has further emphasized the need for vaccination as an alternative means of preventing the large-scale morbidity and mortality associated with pneumococcal infection. The initial attempt to develop an anti-pneumococcal vaccine that consisted of 23 out of 90 of the most prevalent capsular polysaccharides (Pneumovax 23©) was unsuccessful, since the vaccine polysaccharides were unable to elicit an immune response in people at most risk of pneumococcal infection: young children, immuno-compromised patients, and the elderly. Technical advances have allowed the linkage of capsular polysaccharides to highly immunogenic carrier proteins. The implementation of this technology using a vaccine consisting of tetanus toxoid linked to Haemophilus influenzae type B-polysaccharide has led to undetectable levels of carriage of Haemophilus influenzae type B, and an elimination of disease caused by this organism in vaccinated populations. Recently, a polysaccharide conjugate pneumococcal vaccine (Prevnar©) has been licensed in the USA by Wyeth Lederle Vaccines. Prevnar© has been released in The Netherlands in 2001. The vaccine formulation is immunogenic in children, and consists of 7 of the most prevalent capsule polysaccharides conjugated to a highly immunogenic (non-pneumococcal) carrier protein. However, unlike the Haemophilus influenzae vaccine, this vaccine covers only 7 out of 90 of the known pneumococcal capsule serotypes, and clinical data from phase three trials conducted in the USA, Israel, and South Africa have shown that the use of this vaccine causes a shift in colonization by non-vaccine serotypes in place of vaccine serotypes (1, 2, 3, 4, 5). As a result of this apparent weakness associated with narrow spectrum polysaccharide based antigens, attention has been focused on the non-polysaccharide capsule related pneumococcal proteins, many of which are involved in the pathogenesis of infections. These proteins are considered to be interesting components for future vaccines, since they cover all serotypes of pneumococci. The protein loci are less variable than those encoding the genes for capsular polysaccharide production, and they are more likely to be able to elicit an immune response in children (6, 7, 8, 9).

Further all the vaccines that have been developed thus far are systemic vaccines, i.e. vaccines that have to be injected. A mucosal vaccine that could e.g. be administered intranasally would be preferred for ease of administration, especially in children.

In our ongoing studies on the molecular epidemiology and pathogenesis of Streptococcus pneumoniae, we have developed a method for the extraction of surface associated pneumococcal proteins and the subsequent testing of said proteins for binding to antibodies. The antibody-antigen complex is identified, said antigen is isolated and characterized and antibodies, produced against said antigen, are subsequently tested for their opsonizing ability for the microorganism. The antigen, which is binding to an antibody with opsonizing ability for the microorganism having such an antigen on its surface, is identified by for example high-resolution two dimensional PAGE (polyacrylamide gel electrophorsesis) and mass spectrometric identification of the gel spots. This method has provided a means by which we isolated and identified a pneumococcal maturation protein (PpmA) with vaccine potential (10, 11).

The techniques used in the identification of surface-associated pneumococcal proteins, the sequence of ppmA and its protein product (PpmA) and its therapeutic potential are filed under European Patent application nr. 99202640.1.

Many microorganisms are characterized in that they are killed by a phagocytic cell after phagocytosis. Many microorganisms need to be opsonized by opsonins to enhance their phagocytosis. Opsonization is the process of making a microorganism more susceptible for the uptake by a phagocyte. In said process, opsonizing antibodies and/or proteins bind to said microorganism, thereby facilitating the uptake of said microorganism by said phagocyte. Opsonophagocytosis is measured in living phagocytic cells and comprises measuring the uptake by phagocytic cells of microorganisms pretreated with opsonizing antibodies. With this method a selection can be made for surface antigens i.e. antigens naturally or artificially associated with the surface of a microorganism that specifically induce opsonophagocytosis. Of course, surface antigens with opsonophagocytosis inducing ability can be selected from a collection of surface proteins. This typically implies that said surface proteins are isolated from microorganisms and subsequently are purified and tested.

DESCRIPTION OF THE INVENTION

In the present application we disclose a method for identifying surface proteins with opsonophagocytosis inducing ability that does not require the above described mixture of surface antigens as used in the patent application 99202640.1. We hereby disclose a method to combine selection, especially in silico selection with a functional test for opsonophagocytosis. By searching in silico for sequence motifs coding for a membrane anchor, or more preferably for a cell wall binding domain, a protein with opsonophagocytic potential is identified. Said in silico selection is followed by recombinant production of at least part of said selected protein. Said recombinant protein is subsequently used to immunize animals, and/or to contact a collection of antibodies. In mice, active and passive immunization procedures with said recombinant protein or with antibodies against said protein are performed to test the opsonizing potential of said recombinant protein.

Protective ability of the selected protein or part thereof may be measured in a vaccination challenge experiment.

With this method, three proteins have been identified as possible phagocytosis inducing vaccine components and are disclosed herein. One of said proteins is a protein called pneumococcal IgA1 protease (IgA1 proteinase), a protease that can convert human dimer IgA molecules into monomers. Another protein is a peptidyl prolyl isomerase, which we named streptococcal lipoprotein rotamase A (SlrA). Yet another protein is pneumococcal surface adhesion protein A (PsaA)

PpmA protein has been classified as an isomerase enzyme. In our search for other proteins with a homologous function on the surface of the microorganism, we found a protein with a peptidyl prolyl isomerase activity, SlrA. In this application, homologous is defined as sequential homology and/or functional homology.

SlrA, although belonging to another family of proteins than PpmA also appeared to be an opsonophagocytosis-inducing antigen. Surprisingly, abovementioned proteins have not been identified by any other method as being opsonophagocytosis enhancing proteins. For example, there was no correlation between antibody titers against SlrA, or IgA1 proteinase and the first episode of acute otitis media (middle ear infection) in children in a large serological survey in Finland as is described in example one. In the absence of such a correlation, these proteins were not considered to be important for the defense against streptococcal infection.

Since the opsonophagocytic activity correlates with in vivo protection, these data show that SlrA, IgA1 proteinase and PsaA have potential to elicit immune protection. Loss of virulence of microorganisms is often tested in vitro by investigating the replication of a microorganism missing said protein. The absence of SlrA, IgA1 proteinase, or PsaA in recombinant strains of *Streptococcus pneumoniae* did not influence the in vitro characteristics of said microorganism. Therefore, said proteins would not have been selected as vaccine components by methods that are state of the art.

We disclose, in one embodiment, a method to identify an opsonophagocytosis inducing antigen as a vaccine component for immunization against a microorganism, comprising selecting (in silico) via a molecule associated with the surface of a microorganism such as a membrane anchoring motif and/or a cell wall binding domain, a nucleotide sequence encoding at least part of a bacterial protein, and producing at least part of said protein, and contacting a collection of antibodies to said protein and testing for binding between at least one antibody and at least one antigen, and measuring the opsonizing ability of said binding antibody for a microorganism having such an antigen.

The motifs which can be used for the in silico selection comprise, for example, a lipobox (anchoring to membrane via a lipid group), a peptidoglycan binding domain(PBD), a chohne binding domain (CBD) or a LPxTG motief (cell wall binding domain). The above mentioned motifs are characterized as follows:

PBD: [YV]-X$_{(0,4)}$-G-D-[ST]-[VLIA]-X$_{(0,2)}$-[VLIA] (SEQ ID NO:1)

CBD: G-X$_{(0,5)}$-G-X-[WYI]-[WYT]-[YVL]-[FV] (SEQ ID NO:2)

Lipobox (+signal peptide):<M-X$_{(1,10)}$-[RK]-X-{DERK}$_{(7,17)}$-[LVTIMG]-[ASTIVGMLCPFL]-[AGLIS-VTFP]-C (SEQ ID NO: 3)

LPxTG: L-P-X-T-G (SEQ ID NO: 4)

in which X denotes any naturally occurring amino acid, and in which the square brackets indicate one position which can be filled with any of the amino acids indicated between the square brackets. The numbers is subscript indicate that the corresponding amino acid is repeated the indicated number of times.

Of course, said collection of antibodies can be produced by raising antibodies in an animal, by immunizing for example a rabbit or a mouse or a rat or another animal with at least part of said selected protein of said microorganism. Therefore, this application also teaches a method to identify an opsonophagocytosis inducing antigen as a vaccine component for immunisation against a microorganism as described above wherein said collection of antibodies is raised by immunizing an animal with at least one antigen of said microorganism. Antibodies against said proteins may also be selected from pre-existing collections of antibodies or functional parts, derivatives or analogues thereof. This method can be applied to any microorganism for which the defense by the immune system depends on opsonophagocytosis. Therefore, the application teaches a method to identify an opsonophagocytosis inducing antigen as a vaccine component for immunisation against a microorganism as described, wherein said microorganism is for example a member of the genus *Streptococcus*, for example a member of the species of *Streptococcus pneumoniae*, or *Streptococcus viridans*, or *Streptococcus canis*, or *Streptococcus suis*, or a member of the genus *Staphylococcus*, for example a member of the species *Staphylococcus aureus*, or *Staphylococcus epidermidis*, or a coagulase negative *Staphylococcus*, or a member of the species *Moraxella catarrhalis*, or *Neisseria meningitidis*, or *Neisseria ghonorrhoeae*, or *Helicobacter pylori*, or *Haemophilus influenzae* or *Campylobacter jejuni*, or a member of the genus *Pseudomonas*, or the genus *Bacillus*.

Once identified, said partially homologous protein or a part thereof is recombinantly produced and tested for its capability to induce opsonophagocytosis. Therefore, this application also teaches a nucleotide sequence at least encoding for a functional part of a protein, said protein inducing opsonophagocytosis of a microorganism having such a protein, wherein said protein is partially homologous with a protein selected by the method as described above. Said nucleotide sequence can be incorporated into a recombinant vector and herewith, recombinant cells can be provided. Said recombinant cell produces protein based on said nucleotide sequence, therefore, this application teaches a recombinant vector comprising a nucleotide sequence at least encoding for a functional part of a protein, said protein inducing opsonophagocytosis of a microorganism having such a protein, wherein said protein is partially homologous with a protein selected by the method as described above. The application also teaches a recombinant cell expressing at least part of a nucleotide, and a purified protein, produced by said recombinant cell. Said antigen or protein or a part thereof can be used as a vaccine component for immunisation against a microorganism, therefore this application teaches a vaccine component for immunisation against a micro organism which can be killed by opsonophagocytic cells, said vaccine component comprising said protein, and/or an antigenic part thereof. In one embodiment, said vaccine component may comprise at least a functional part of streptococcal lipoprotein rotamase A (SlrA) of *Streptococcus pneumoniae*. Therefore, this patent application discloses said vaccine component, comprising at least a functional part of streptococcal lipoprotein rotamase A (SlrA) of *Streptococcus pneumoniae*. In another embodiment, said vaccine component may comprise at least a functional part of pneumococcal IgA1 protease (IgA1) of *Streptococcus pneumoniae*. Therefore, this patent application discloses said vaccine component, comprising at least a functional part of pneumococcal IgA1 protease (IgA1) of *Streptococcus pneumoniae*.

In yet another embodiment, said vaccine component may comprise at least a functional part of pneumococcal surface adhesion protein A (PsaA) of *Streptococcus pneumoniae*. Therefore, this patent application discloses said vaccine component, comprising at least a functional part of pneumococcal surface adhesion protein A (PsaA) of *Streptococcus pneumoniae*.

With the wording "at least a functional part" of a protein it is meant that the minimal amount of amino acid is taken which is still able to raise an immune response in the vaccinate subject. Also the term "antigenic part" is used in this specification to identify such a functional part of a protein. Generally, such parts will at least be more than 10 amino acids, and preferably about 50-100 amino acids.

We disclose in this patent application the protective ability of said proteins by active and passive immunization in a mouse model both with systemic vaccination and mucosal vaccination.

It may be advantageous to combine more than one surface protein or a functional part thereof in a vaccine, and also to combine at least one surface protein or functional part thereof with PpmA or with another protein to induce an even better immunity. Therefore, in another embodiment, said vaccine component may also comprise at least an antigenic part of pneumococcal maturation protein A (PpmA) of *Streptococcus pneumoniae* or another protein. With said vaccine components, a vaccine may be produced for the treatment of an infection by a microorganism, which can be killed by opsonophagocytic cells.

Therefore, this application teaches a vaccine comprising at least one of said vaccine components and/or a homologous and/or functionally homologous protein or protein fragment thereof for the treatment of an infection by a microorganism that can be killed by opsonophagocytic cells. Of course, one may formulate said vaccine with a pharmaceutically acceptable carrier and/or adjuvant. Preferably said adjuvant comprises cell wall material of Gram positive bacteria, more preferable it comprises co-called ghosts (empty bacterial cells, which still have an intact cell wall structure). It is further preferable to couple the antigens to such ghosts, for example by using protein anchors, such as the AcmA protein anchor. Other adjuvants may be chosen from adjuvant preparations known in the art, such as emulsions with vitamin E. Therefore, this application also teaches said vaccine, also comprising a pharmaceutically acceptable carrier and/or adjuvant.

For passive immunization, specific antibodies against each of said proteins were administered to mice and the protection of said passive immunity against a challenge infection with virulent *Streptococcus pneumoniae* was measured. Of course, this method can now be applied to all microorganisms for which the immune response by the host is based on killing of said microorganism by phagocytes, for example but not restricted to for example a member of the genus *Strepococcus*, for example a member of the species of *Strepococcus pneumoniae*, or *Strepococcus viridans*, or *Strepococcus canis*, or *Strepococcus suis*, or a member of the genus *Staphylococcus*, for example a member of the species *Staphylococcus aureus*, or *Staphylococcus epidermidis*, or a coagulase negative *Staphylococcus*, or a member of the species *Moraxella catarrhalis*, or *Neisseria meningitidis*, or *Neisseria ghonorrhoeae*, or *Helicobacter pylori*, or *Haemophilus influenzae* or *Cainpylobacter jejuni*, or a member of the genus *Pseudomonas*, or the genus *Bacillus*.

As used herein, the terms "antibody" and "antibodies" refer to monoclonal antibodies, multispecific antibodies (e.g., bi-specific), human antibodies, humanized antibodies, camelised antibodies, chimeric antibodies, single-chain Fvs (scFv), single chain antibodies, synthetic antibodies, single domain antibodies, Fab fragments, F(ab) fragments, disulfide-linked Fvs (sdFv), and anti-idiotypic (anti-Id) antibodies, and epitope-binding fragments of any of the above. In particular, antibodies include immunoglobulin molecules and immunologically active fragments of immunoglobulin molecules, i.e., molecules that contain an antigen binding site. Immunoglobulin molecules can be of any type (e.g., IgG, IgE, IgM, IgD, IgA and IgY), class (e.g., IgG1, IgG2, IgG3, IgG4, IgA1 and IgA2) or subclass.

Antibodies of the invention include, but are not limited to, monoclonal antibodies, multispecific antibodies, synthetic antibodies, human antibodies, humanized antibodies, chimeric antibodies, single-chain Fvs (scFv), single chain antibodies, Fab fragments, F(ab') fragments, disulfide-linked Fvs (sdFv), and anti-idiotypic (anti-Id) antibodies (including, e.g., anti-Id antibodies to antibodies of the invention), and epitope-binding fragments of any of the above. In particular, antibodies of the present invention include immunoglobulin molecules and immunologically active portions of immunoglobulin molecules, i.e., molecules that contain an antigen binding site that immunospecifically binds to a vaccine component according to the invention. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule.

The antibodies of the invention may be from any animal origin including birds and mammals (e.g., human, murine, donkey, sheep, rabbit, goat, guinea pig, camel, horse, or chicken). Preferably, the antibodies of the invention are human or humanized monoclonal antibodies. As used herein, "human" antibodies include antibodies having the amino acid sequence of a human immunoglobulin and include antibodies isolated from human immunoglobulin libraries (including, but not limited to, synthetic libraries of immunoglobulin sequences homologous to human immunoglobulin sequences) or from mice that express antibodies from human genes.

In certain embodiments, high potency antibodies can be used in the methods of the invention. For example, high potency antibodies can be produced by genetically engineering appropriate antibody gene sequences and expressing the antibody sequences in a suitable host. The antibodies produced can be screened to identify antibodies with, e.g., high kon values in a BIAcore assay (see below).

In certain embodiments, an antibody to be used with the methods of the present invention or fragment thereof has an affinity constant or $K_a$ (kon/koff) of at least $10^2$ M-1, at least $5\times10^2$ M-1, at least $10^3$ M-1, at least $5\times10^3$ M-1, at least $10^4$ M-1, at least $5\times10^4$ M-1, at least $10^5$ M-1, at least $5\times10^5$ M-1, at least $10^6$ M-1, at least $5\times10^6$ M-1, at least $10^7$ M-1, at least $5\times10^7$ M-1, at least $10^8$ M-1, at least $5\times10^8$ M-1, at least $10^9$ M-1, at least $5\times10^9$ M-1, at least $10^{10}$ M-1, at least $5\times10^{10}$ M-1, at least $10^{11}$ M-1, at least $5\times10^{11}$ M-1, at least $10^{12}$ M-1, at least $5\times10^{12}$ M-1, at least $10^{13}$ M-1, at least $5\times10^{13}$ M-1, at least $10^{14}$ M-1, at least $5\times10^{14}$ M-1, at least $10^{15}$ M-1, or at least $5\times10^{15}$ M-1. In yet another embodiment, an antibody to be used with the methods of the invention or fragment thereof has a dissociation constant or $K_d$ (koff/kon) of less than $10^{-2}$ M, less than $5\times10^{-2}$ M, less than $10^{-3}$ M, less than $5\times10^{-3}$ M, less than $10^{-4}$ M, less than $5\times10^{-4}$ M, less than $10^{-5}$ M, less than $5\times10^{-5}$ M, less than $10^{-6}$ M, less than $5\times10^{-6}$ M, less than $10^{-7}$ M, less than $5\times10^{-7}$ M, less than $10^{-8}$ M, less than $5 \times 10^{-8}$ M, less than $10^{-9}$ M, less than $5 \times 10^{-9}$ M, less than $10^{-10}$ M, less than $5 \times 10^{-10}$ M, less than $10^{-11}$ M, less than $5 \times 10^{-11}$ M, less than $10^{-12}$ M, less than $5 \times 10^{-12}$ M, less than $10^{-13}$ M, less than $5 \times 10^{-13}$ M, less than $10^{-14}$ M, less than $5 \times 10^{-14}$ M, less than $10^{-15}$ M, or less than $5 \times 10^{-15}$ M.

In certain embodiments, an antibody to be used with the methods of the invention or fragment thereof that has a median effective concentration (EC50) of less than 0.01 nM, less than 0.025 nM, less than 0.05 nM, less than 0.1 nM, less than 0.25 nM, less than 0.5 nM, less than 0.75 nM, less than 1 nM, less than 1.25 nM, less than 1.5 nM, less than 1.75 nM, or less than 2 nM, in an in vitro microneutralization assay. The median effective concentration is the concentration of antibody or antibody fragments that neutralizes 50% of the infective micro-organism in an in vitro microneutralization assay. In a preferred embodiment, an antibody to be used with the methods of the invention or fragment thereof has an EC50 of less than 0.01 nM, less than 0.025 nM, less than 0.05 nM, less than 0.1 nM, less than 0.25 nM, less than 0.5 nM, less than 0.75 nM, less than 1 nM, less than 1.25 nM, less than 1.5 nM, less than 1.75 nM, or less than 2 nM, in an in vitro microneutralization assay.

The antibodies to be used with the methods of the invention include derivatives that are modified, i.e, by the covalent attachment of any type of molecule to the antibody. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, synthesis in the presence of tunicamycin, etc. Additionally, the derivative may contain one or more non-classical amino acids.

The present invention also provides antibodies of the invention or fragments thereof that comprise a framework region known to those of skill in the art. In certain embodiments, one or more framework regions, preferably, all of the framework regions, of an antibody to be used in the methods of the invention or fragment thereof are human. In certain other embodiments of the invention, the framework region of an antibody of the invention or fragment thereof is humanized. In certain embodiments, the antibody to be used with the methods of the invention is a synthetic antibody, a monoclonal antibody, an intrabody, a chimeric antibody, a human antibody, a humanized chimeric antibody, a humanized antibody, a glycosylated antibody, a multispecific antibody, a human antibody, a single-chain antibody, or a bispecific antibody.

In certain embodiments of the invention, the antibodies to be used with the invention have half-lives in a mammal, preferably a human, of greater than 12 hours, greater than 1 day, greater than 3 days, greater than 6 days, greater than 10 days, greater than 15 days, greater than 20 days, greater than 25 days, greater than 30 days, greater than 35 days, greater than 40 days, greater than 45 days, greater than 2 months, greater than 3 months, greater than 4 months, or greater than 5 months. Antibodies or antigen-binding fragments thereof having increased in vivo half-lives can be generated by techniques known to those of skill in the art. For example, antibodies or antigen-binding fragments thereof with increased in vivo half-lives can be generated by modifying (e.g., substituting, deleting or adding) amino acid residues identified as involved in the interaction between the Fc domain and the FcRn receptor (see, e.g., PCT Publication No. WO 97/34631 and U.S. Patent Application No.: 10/020,354, entitled "Molecules with Extended Half-Lives, Compositions and Uses Thereof", filed Dec. 12, 2001, by Johnson et al., which are incorporated herein by reference). Such antibodies or antigen-binding fragments thereof can be tested for binding activity to the vaccine components of the invention as well as for in vivo efficacy using methods known to those skilled in the art, for example, by immunoassays described herein.

Further, antibodies or antigen-binding fragments thereof with increased in vivo half-lives can be generated by attaching to said antibodies or antibody fragments polymer molecules such as high molecular weight polyethyleneglycol. (PEG). PEG can be attached to said antibodies or antibody fragments with or without a multifunctional linker either through site-specific conjugation of the PEG to the N- or C-terminus of said antibodies or antibody fragments or via epsilon-amino groups present on lysine residues. Linear or branched polymer derivatization that results in minimal loss of biological activity will be used. The degree of conjugation will be closely monitored by SDS-PAGE and mass spectrometry to ensure proper conjugation of PEG molecules to the antibodies. Unreacted PEG can be separated from antibody-PEG conjugates by, e.g., size exclusion or ion-exchange chromatography. PEG-derivatizated antibodies or antigen-binding fragments thereof can be tested for binding activity to the vaccine components of the invention as well as for in vivo efficacy using methods known to those skilled in the art, for example, by immunoassays described herein.

In certain embodiments, the antibodies to be used with the methods of the invention are fusion proteins comprising an antibody or fragment thereof that immunospecifically binds to a vaccine component of the invention and a heterologous polypeptide. Preferably, the heterologous polypeptide that the antibody or antibody fragment is fused to is useful for targeting the antibody to cells which are prone to infection.

In certain embodiments, antibodies to be used with the methods of the invention or fragments thereof disrupt or prevent the interaction between an microbial antigen and its host cell receptor.

In certain embodiments, antibodies to be used with the methods of the invention are single-chain antibodies. The design and construction of a single-chain antibody is described in Marasco et al, 1993, Proc Natl Acad Sci 90:7889-7893, which is incorporated herein by reference.

In certain embodiments, the antibodies to be used with the invention bind to an intracellular epitope, i.e., are intrabodies. An intrabody comprises at least a portion of an antibody that is capable of immunospecifically binding an antigen and preferably does not contain sequences coding for its secretion. Such antibodies will bind its antigen intracellularly. In one embodiment, the intrabody comprises a single-chain Fv ("sFv"). sFv are antibody fragments comprising the VH (variable heavy) and VL (variable light) domains of antibody, wherein these domains are present in a single polypeptide chain. Generally, the Fv polypeptide further comprises a polypeptide linker between the VH and VL domains which enables the sFv to form the desired structure for antigen binding. For a review of sFv see Pluckthun in The Pharmacology of Monoclonal Antibodies, vol. 113, Rosenburg and Moore eds. Springer-Verlag, New York, pp. 269-315 (1994). In a further embodiment, the intrabody preferably does not encode an operable secretory sequence and thus remains within the cell (see generally Marasco, Wash., 1998, "Intrabodies: Basic Research and Clinical Gene Therapy Applications" Springer:New York).

Generation of intrabodies is well-known to the skilled artisan and is described for example in U.S. Pat. Nos. 6,004,940; 6,072,036; 5,965,371, which are incorporated by reference. Further, the construction of intrabodies is discussed in Ohage and Steipe, 1999, J. Mol. Biol. 291:1119-1128; Ohage et al., 1999, J. Mol. Biol. 291:1129-1134; and Wirtz and Steipe, 1999, Protein Science 8:2245-2250. Recombinant molecular biological techniques such as those described for recombinant production of antibodies (see below) may also be used in the generation of intrabodies.

In one embodiment, intrabodies of the invention retain at least about 75% of the binding effectiveness of the complete antibody (i.e., having constant as well as variable regions) to the antigen. More preferably, the intrabody retains at least 85% of the binding effectiveness of the complete antibody. Still more preferably, the intrabody retains at least 90% of the binding effectiveness of the complete antibody. Even more preferably, the intrabody retains at least 95% of the binding effectiveness of the complete antibody.

In producing intrabodies, polynucleotides encoding the variable region for both the VH and VL chains of interest can be cloned by using, for example, hybridoma mRNA or splenic mRNA as a template for PCR amplification of such domains (Huse et al., 1989, Science 246:1276). In one preferred embodiment, the polynucleotides encoding the VH and VL domains are joined by a polynucleotide sequence encoding a linker to make a single chain antibody (sFv). The sFv typically comprises a single peptide with the sequence VH-linker-VL or VL-linker-VH. The linker is chosen to permit the heavy chain and light chain to bind together in their proper conformational orientation (see for example, Huston, et al., 1991, Methods in Enzym. 203:46-121). In a further embodiment, the linker can span the distance between its points of fusion to each of the variable domains (e.g., 3.5 nm) to minimize distortion of the native Fv conformation. In such an embodiment, the linker is a polypeptide of at least 5 amino acid residues, at least 10 amino acid residues, at least 15 amino acid residues, or greater. In a further embodiment, the linker should not cause a steric interference with the VH and VL domains of the combining site. In such an embodiment, the linker is 35 amino acids or less, 30 amino acids or less, or 25 amino acids or less. Thus, in a most preferred embodiment, the linker is between 15-25 amino acid residues in length. In a further embodiment, the linker is hydrophilic and sufficiently flexible such that the VH and VL domains can adopt the conformation necessary to detect antigen. Intrabodies can be generated with different linker sequences inserted between identical VH and VL domains. A linker with the appropriate properties for a particular pair of VH and VL domains can be determined empirically by assess the degree of antigen binding for each. Examples of linkers include, but are not limited to, those sequences disclosed in Table 1A.

TABLE 1A

Sequence (SEQ ID NO: 5)
(Gly Gly Gly Gly Ser)3

(SEQ ID NO: 6)
Glu Ser Gly Arg Ser Gly Gly Gly Ser Gly Gly
Gly Gly Ser (SEQ ID NO: 7)
Glu Gly Lys Ser Ser Gly Ser Gly Ser Glu Ser Lys
Ser Thr (SEQ ID NO: 8)
Glu Gly Lys Ser Ser Gly Ser Gly Ser Glu Ser Lys
Ser Thr Gln

TABLE 1A-continued (SEQ ID NO: 9)
Glu Gly Lys Ser Ser Gly Ser Gly Ser Glu Ser Lys
Val Asp (SEQ ID NO: 10)
Gly Ser Thr Ser Gly Ser Gly Lys Ser Ser Glu Gly
Lys Gly (SEQ ID NO: 11)
Lys Glu Ser Gly Ser Val Ser Ser Glu Gln Leu Ala
Gln Phe Arg Ser Leu Asp (SEQ ID NO: 12)
Glu Ser Gly Ser Val Ser Ser Glu Glu Leu Ala Phe
Arg Ser Leu Asp In one embodiment, intrabodies are expressed in the cytoplasm. In other embodiments, the intrabodies are localized to various intracellular locations. In such embodiments, specific localization sequences can be attached to the intranucleotide polypepetide to direct the intrabody to a specific location. Intrabodies can be localized, for example, to the following intracellular locations: endoplasmic reticulum (Munro et al., 1987, Cell 48:899-907; Hangejorden et al., 1991, J. Biol. Chem. 266:6015); nucleus (Lanford et al., 1986, Cell 46:575; Stanton et al., 1986, PNAS 83:1772; Harlow et al., 1985, Mol. Cell Biol. 5:1605); nucleolar region (Seomi et al., 1990, J. Virology 64:1803; Kubota et al., 1989, Biochem. Biophys. Res. Comm. 162:963; Siomi et al., 1998, Cell 55:197); endosomal compartment (Bakke et al., 1990, Cell 63:707-716); mitochondrial matrix (Pugsley, A. P., 1989, "Protein Targeting", Academic Press, Inc.); Golgi apparatus (Tang et al., 1992, J. Bio. Chem. 267:10122-6); liposomes (Letourneur et al., 1992, Cell 69:1183); and plasma membrane (Marchildon et al., 1984, PNAS 81:7679-82; Henderson et al., 1987, PNAS 89:339-43; Rhee et al., 1987, J. Virol. 61:1045-53; Schultz et al., 1984, J. Virol. 133:431-7; Ootsuyama et al., 1985, Jpn. J. Can. Res. 76:1132-5; Ratner et al., 1985, Nature 313:277-84). Examples of localization signals include, but are not limited to, those sequences disclosed in Table 2A.

TABLE 2A

| Localization | Sequence |
|---|---|
| endoplasmic reticulum | Lys Asp Glu Leu (SEQ ID NO: 13) |
| endoplasmic reticulum | Asp Asp Glu Leu (SEQ ID NO: 14) |
| endoplasmic reticulum | Asp Glu Glu Leu (SEQ ID NO: 15) |
| endoplasmic reticulum | Gln Glu Asp Leu (SEQ ID NO: 16) |
| endoplasmic reticulum | Arg Asp Glu Leu (SEQ ID NO: 17) |
| nucleus | Pro Lys Lys Lys Arg Lys Val (SEQ ID NO: 18) |
| nucleus | Pro Gln Lys Lys Ile Lys Ser (SEQ ID NO: 19) |
| nucleus | Gln Pro Lys Lys Pro (SEQ ID NO: 20) |
| nucleus | Arg Lys Lys Arg (SEQ ID NO: 21) |

TABLE 2A-continued

| Localization | Sequence | |
|---|---|---|
| nucleolar region | Arg Lys Lys Arg Arg Gln Arg Arg Arg Ala His Gln | (SEQ ID NO: 22) |
| nucleolar region | Arg Gln Ala Arg Arg Asn Arg Arg Arg Arg Trp Arg Glu Arg Gln Arg | (SEQ ID NO: 23) |
| nucleolar region | Met Pro Leu Thr Arg Arg Arg Pro Ala Ala Ser Gln Ala Leu Ala Pro Pro Thr Pro | (SEQ ID NO: 24) |
| endosomal | Met Asp Asp Gln Arg Asp Leu Ile | (SEQ ID NO: 25) |
| compartment | Ser Asn Asn Glu Gln Leu Pro | (SEQ ID NO: 26) |
| mitochondrial matrix | Met Leu Phe Asn Leu Arg Xaa Xaa Leu Asn Asn Ala Ala Phe Arg His Gly His Asn Phe Met Val Arg Asn Phe Arg Cys Gly Gln Pro Leu Xaa | (SEQ ID NO: 27) |
| plasma membrane | GCVCSSNP | (SEQ ID NO: 28) |
| plasma membrane | GQTVTTPL | (SEQ ID NO: 29) |
| plasma membrane | GQELSQHE | (SEQ ID NO: 30) |
| plasma membrane | GNSPSYNP | (SEQ ID NO: 31) |
| plasma membrane | GVSGSKGQ | (SEQ ID NO: 32) |
| plasma membrane | GQTITTPL | (SEQ ID NO: 33) |
| plasma membrane | GQTLTTPL | (SEQ ID NO: 34) |
| plasma membrane | GQIFSRSA | (SEQ ID NO: 35) |
| plasma membrane | GQIHGLSP | (SEQ ID NO: 36) |
| plasma membrane | GARASVLS | (SEQ ID NO: 37) |
| plasma membrane | GCTLSAEE | (SEQ ID NO: 38) |

VH and VL domains are made up of the immunoglobulin domains that generally have a conserved structural disulfide bond. In embodiments where the intrabodies are expressed in a reducing environment (e.g., the cytoplasm), such a structural feature cannot exist. Mutations can be made to the intrabody polypeptide sequence to compensate for the decreased stability of the immunoglobulin structure resulting from the absence of disulfide bond formation. In one embodiment, the VH and/or VL domains of the intrabodies contain one or more point mutations such that their expression is stabilized in reducing environments (see Steipe et al., 1994, J. Mol. Biol. 240:188-92; Wirtz and Steipe, 1999, Protein Science 8:2245-50; Ohage and Steipe, 1999, J. Mol. Biol. 291:1119-28; Ohage et al., 1999, J. Mol Biol. 291:1129-34).

Methods for Producing Antibodies

The antibodies to be used with the methods of the invention or fragments thereof can be produced by any method known in the art for the synthesis of antibodies, in particular, by chemical synthesis or preferably, by recombinant expression techniques.

Polyclonal antibodies to vaccine component of the invention can be produced by various procedures well known in the art. For example, an antigen according to the invention can be administered to various host animals including, but not limited to, rabbits, mice, rats, etc. to induce the production of sera containing polyclonal antibodies specific for the antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, bacterial ghosts, and potentially useful human adjuvants such as BCG (bacille Calmette-Guerin) and corynebacterium parvum. Such adjuvants are also well known in the art. In the case of ghosts the antigens are preferably coupled to the ghost, for instance through protein anchors, of which the AcmA protein anchor is especially preferred.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563-681 (Elsevier, N.Y., 1981). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art. Ascites fluid, which generally contains high levels of antibodies; can be generated by immunizing mice with positive hybridoma clones.

In certain embodiments, a method of generating monoclonal antibodies comprises culturing a hybridoma cell secreting an antibody of the invention wherein, preferably, the hybridoma is generated by fusing splenocytes isolated from a mouse immunized with an antigen with myeloma cells and then screening the hybridomas resulting from the fusion for hybridoma clones that secrete an antibody able to bind said antigen.

Antibody fragments which recognize the specific antigens of the invention may be generated by any technique known to those of skill in the art. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain. Further, the antibodies to be used with the present invention can also be generated using various phage display methods known in the art.

In phage display methods, functional antibody domains are displayed on the surface of phage particles which carry the polynucleotide sequences encoding them. In particular, DNA sequences encoding VH and VL domains are amplified from animal cDNA libraries (e.g., human or murine cDNA libraries of lymphoid tissues). The DNA encoding the VH and VL domains are recombined together with an scFv linker by PCR and cloned into a phagemid vector (e.g., p CANTAB 6 or pComb 3 HSS). The vector is electroporated in *E. coli* and the *E. coli* is infected with helper phage. Phage used in these methods are typically filamentous phage including fd and M13 and the VH and VL domains are usually recombinantly fused to either the phage gene III or gene VIII. Phage expressing an antigen binding domain that binds to an antigen of interest can be selected or identified with antigen, e.g., using labeled antigen or antigen bound or captured to a solid surface or bead. Examples of phage display methods that can be used to make the antibodies of the present invention include those disclosed in Brinkman et al., 1995, J. Immunol. Methods 182:41-50; Ames et al., 1995, J. Immunol. Methods 184:177-186; Kettleborough et al., 1994, Eur. J. Immunol. 24:952-958; Persic et al., 1997, Gene 187:9-18; Burton et al., 1994, Advances in Immunology 57:191-280; PCT application No. PCT/GB91/O1 134; PCT publication Nos. WO 90/02809, WO 91/10737, WO 92/01047, WO 92/18619, WO 93/1 1236, WO 95/15982, WO 95/20401, and WO97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743 and 5,969,108.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e g., as described below. Techniques to recombinantly produce Fab, Fab' and F(ab')2 fragments can also be employed using methods known in the art such as those disclosed in PCT publication No. WO 92/22324; Mullinax et al., 1992, BioTechniques 12(6):864-869; Sawai et al., 1995, AJRI 34:26-34; and Better et al., 1988, Science 240:1041-1043.

To generate whole antibodies, PCR primers including VH or VL nucleotide sequences, a restriction site, and a flanking sequence to protect the restriction site can be used to amplify the VH or VL sequences in scFv clones. Utilizing cloning techniques known to those of skill in the art, the PCR amplified VH domains can be cloned into vectors expressing a VH constant region, e.g., the human gamma 4 constant region, and the PCR amplified VL domains can be cloned into vectors expressing a VL constant region, e.g., human kappa or lamba constant regions. Preferably, the vectors for expressing the VH or VL domains comprise an EF-1α promoter, a secretion signal, a cloning site for the variable domain, constant domains, and a selection marker such as neomycin. The VH and VL domains may also cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

For some uses, including in vivo use of antibodies in humans and in vitro detection assays, it may be preferable to use human or chimeric antibodies. Completely human antibodies are particularly desirable for therapeutic treatment of human subjects. Human antibodies can be made by a variety of methods known in the art including phage display methods described above using antibody libraries derived from human immunoglobulin sequences or synthetic sequences homologous to human immunoglobulin sequences. See also U.S. Pat. Nos. 4,444,887 and 4,716,111; and PCT publications WO 98/46645, WO 98/50433, WO 98/24893, WO98/16654, WO 96/34096, WO 96/33735, and WO 91/10741.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then be bred to produce homozygous offspring which express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, Int. Rev. Immunol. 13:65-93). For a detailed discussion of this technology for producing human antibodies and human monoclonal antibodies and protocols for producing such antibodies, see, e.g., PCT publication Nos. WO 98/24893, WO 96/34096, and WO 96/33735; and U.S. Pat. Nos. 5,413,923, 5,625,126, 5,633,425, 5,569,825, 5,661,016, 5,545,806, 5,814,318, and 5,939,598. In addition, companies such as Medarex, Inc. (Princeton, N.J), Abgenix, Inc. (Freemont, Calif.) and Genpharm (San Jose, Calif.) can be engaged to provide human antibodies directed against a selected antigen using technology similar to that described above.

A chimeric antibody is a molecule in which different portions of the antibody are derived from different immunoglobulin molecules such as antibodies having a variable region derived from a non-human (e.g., murine) antibody and a human immunoglobulin constant region. Methods for producing chimeric antibodies are known in the art. See e.g., Morrison, 1985, Science 229:1202; Oi et al., 1986, BioTechniques 4:214; Gillies et al., 1989, J. Immunol. Methods 125: 191-202; and U.S. Pat. Nos. 5,807,715, 4,816,567, and 4,816, 397. Chimeric antibodies comprising one or more CDRs (complementarity determining regions) from human species and framework regions from a non-human immunoglobulin molecule can be produced using a variety of techniques known in the art including, for example, CDR-grafting (EP 239,400; PCT publication No. WO 91/09967; and U.S. Pat. Nos. 5,225,539, 5,530,101, and 5,585,089), veneering or resurfacing (EP 592,106; EP 519,596; Padlan, 1991, Molecular Immunology 28(4/5):489-498; Studnicka et al., 1994, Protein Engineering 7(6):805-814; and Roguska et al., 1994, PNAS 91:969-973), and chain shuffling (U.S. Pat. No. 5,565, 332). In a preferred embodiment, antibodies comprise one or more CDRs and human framework regions. Often, framework residues in the framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; and Riechmann et al., 1988, Nature 332:323.)

Polynucleotides encoding antibodies to be used with the invention may be obtained, and the nucleotide sequence of the polynucleotides determined, by any method known in the art. Such a polynucleotide encoding the antibody may be assembled from chemically synthesized oligonucleotides (e.g., as described in Kutmeier et al., 1994, BioTechniques 17:242).

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, preferably poly A+RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y and Ausubel et al., eds., 1998, Current Protocols in Molecular Biology, John Wiley & Sons, NY), to generate antibodies having a different amino acid sequence, for example to create amino acid substitutions, deletions, and/or insertions.

In a specific embodiment, one or more of the CDRs is inserted within framework regions using routine recombinant DNA techniques. The framework regions may be naturally occurring or consensus framework regions, and preferably human framework regions (see, e.g., Chothia et al., 1998, J. Mol. Biol. 278: 457-479 for a listing of human framework regions). Preferably, the polynucleotide generated by the combination of the framework regions and CDRs encodes an antibody that specifically binds to a vaccine component of the invention. In certain embodiments, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

Recombinant expression of an antibody to be used with the methods of the invention, derivative or analog thereof, (e.g., a heavy or light chain of an antibody of the invention or a portion thereof or a single chain antibody of the invention), requires construction of an expression vector containing a polynucleotide that encodes the antibody. Once such a polynucleotide has been obtained, the vector for the production of the antibody molecule may be produced by recombinant DNA technology using techniques well known in the art. The expression vector is transferred to a host cell by conventional techniques and the transfected cells are then cultured by conventional techniques to produce an antibody of the invention.

Antibodies according to the invention can not only be used for passive vaccination, but can also be used for diagnostic purposes and in assay systems to detect presence of bacteria and/or the antigens to which they are directed. Such a diagnosis is useful (for instance) to test material (such as food, pharmaceutical compositions or air filters) for the presence of bacteria. It is also possible to develop a test system which can detect the antibodies themselves to check for the presence or to calculate the titer of antibodies in the blood of subjects that have been immunized with a vaccine according to the invention.

A person skilled in the art is well able to generate analogous compounds of the opsonophagocytosis inducing proteins of the invention. This can for instance be done through screening of a peptide library and testing to binding to one or more of the antibodies described above. Such an analogue has essentially the same biological properties of said protein in kind, i.e. it is able to generate a similar immunological response, not necessarily in amount.

It will also be possible genetically engineer analogous compounds starting from the sequences provided in this specification. Such analogous compounds will have a sequence identity of more than 50% compared to the sequences given in the specification. Sequence identity may be defined and determined by the TBLASTN or TBLASTP program for nucleic acid or amino acid sequences, respectively, of Altschul et al. (1990), which is in standard use in the art, or, and this may be preferred, the standard program Best-Fit, which is part of the Wisconsin Package, Version 8, September 1994, (Genetics Computer Group, 575 Science Drive, Madison, Wis., USA, Wisconsin 53711). Sequence identity on nucleotide sequences can be calculated by using the BLASTN computer program (which is publicly available, for instance through the National Center for Biotechnological Information, accessible via the internet on http://www.ncbi.nlm.nih.gov/) using the default settings of 11 for wordlength (W), 10 for expectation (E), 5 as reward score for a pair of matching residues (M), −4 as penalty score for mismatches (N) and a cutoff of 100. Sequence identity may be at the nucleotide sequence and/or encoded amino acid sequence level. Preferably the nucleic acid and/or amino acid sequence shares at least 50%, or 60% sequence identity, most preferably at least about 70%, or 80% or 90% sequence identity with the sequences of the specification as provided hereunder.

It is also possible to search for orthologous proteins, i.e. proteins from other organisms, be it closely related or not to *Strepococcus pneumoniae* D39 and/or *Streptococcus pneumoniae* TIGR4, such as other *Streptococcus pneumoniae* strains, or other *Streptococcus* species, or even *Staphylococcus, Moraxella, Neisseria* and other bacteria, or even non-bacterial organisms. Orthologous proteins in this regard means proteins from other species which proteins have the same common ancestry, but are different in sequence as a result of (spontaneous) mutations. These sequences can easily been found, for instance by comparing the sequences of the invention to other sequences available in sequence databases such as GenBank or by isolating orthologous proteins from other organisms by PCR mediated amplification methods in which (degenerated) primers are designed based on the sequences of the specification. Such methods are known to the person skilled in the art.

The proteins obtained by the above described methods should further be tested with respect to their opsonophagocytosis inducing properties. Any protein obtained through the above discussed methods which appears to be opsonophagocytosis inducing is considered to be a protein of the invention and is considered to be suitable for inclusion into the vaccines of the invention. Also parts of these proteins which have retained the functional characteristic of being able to induce opsonophagocytosis are considered to be comprised in the present invention.

Opsonophagocytosis inducing proteins as vaccine components can also be combined with other opsonophagocytosis inducing proteins and/or other proteins to result in a better vaccine. This patent application discloses the use of SlrA, IgA1 proteinase and PsaA and the combination of PpmA and/or other proteins with said proteins. Preferably, a vaccine according to the invention comprises two of more opsonophagocytosis inducing proteins, wherein the combination of PpmA and SlrA, whether or not in the presence of further antigens, is most preferred.

The invention is further explained in the examples.

EXAMPLE 1

Correlation of Antibody Titers Against *Strepococcus pneumoniae* Surface Proteins with Occurrence of first Acute Otitis Media.
A Cross Sectional Population Survey in Finland.

As is shown in FIGS. 1-5 in people with first occurrence of otitis media, the IgG titers against PpmA, SlrA, and IgA1 proteinase, are all lower than the titers against alpha-enolase of *Strepococcus pneumoniae*. Because of the absence of this correlation of antibody titer and protection, SlrA and IgA1 proteinase were considered to have no added value for protective immunity, and hence would not be selected for use as a vaccine component.

EXAMPLE 2

Immune Protective Potential of *Strepococcus pneumoniae* Surface proteins

To determine the protective potential of *Strepococcus pneumoniae* surface proteins, both active and passive immunization/challenge experiments were performed.
Methods
Mouse Strains Immunisation was carried out on MF1 outbred female mice, purchased from Harlan Olac, Bicester, UK All mice were barrier reared and specified pathogen free. The active immunisation protocol started with 6 week old mice (25-30g) and passive immunisation with 9 week old mice (30-35g).
Bacterial Strains

*Strepococcus pneumoniae* D39, serotype 2, has been obtained from the National Collection of Type Cultures (NCTC 7466; Central Public Health Laboratory, London). *Strepococcus pneumoniae* TIGR4, serotype 4, has been obtained from The Institute for Genome Research. Bacteria are grown on Blood Agar Base Number 2 (Oxoid, Basingstoke, UK) plus 5% (vol/vol) defibrinated horse blood (BAB). Stock cultures are prepared by inoculating a sweep of 4-5 colonies into 25ml Brain-Heart Infusion broth (BHI, Oxoid). Cultures are grown statically at 37° C. overnight before 1 ml aliquots containing 15% sterile glycerol are frozen at −70° C. until use. Strain validation is carried out by confirming sensitivity to the antibiotic Optochin (Difco, Detroit, USA). Serotype verification is performed by checking for the presence of type specific polysaccharide capsule-using anti-type 2 or 4 capsule antiserum (Statens Seruminstitut, Copenhagen, Denmark).

For counting of CFU, serial dilutions of samples are prepared by the addition of 20 µl to 180 µl sterile PBS in sterile round-bottomed 96 well microtitre plates (Life Technologies, Paisley, UK). 20 µl volumes of each dilution are spotted in triplicate on 2 separate BAB plates. The following equation is used to calculate the number of colony forming units per ml of sample:

$$\text{CFU per ml} = \text{Mean number of colonies per sector} \times 50 \times \text{Dilution Factor.}$$

Preparation of Inoculums

100µl of sterile PBS containing approximately $10^5$ CFU *Strepococcus pneumoniae* were injected into the peritoneal cavity of mice with an insulin syringe (F. Baker Scientific, Runcorn, UK). On development of lethargy, mice were killed by cervical dislocation, the chest cavity carefully opened up and a section of ribcage removed in order to provide access to the heart. A 23 gauge needle was inserted into the right ventricle and blood slowly collected into the attached syringe. 50 µl of infected blood was used to grow passaged bacteria in 10 ml BHI statically overnight at 37° C. Bacteria were harvested by centrifugation at 3,000 rpm for 10 min (Heraeus medifuge), resuspended in fresh BHI containing 20% v/v FCS and then incubated at 37° C. until they reached mid-log phase (as judged by optical density). 1 ml aliquots of the suspension were stored at −70° C., until required. After 24h at −70° C. viability of the suspension was measured by viable counting and optochin sensitivity was confirmed. Viability was unaffected by storage at −70° C. for at least 3 months.
Intranasal Infection Aliquots of standard inoculum were rapidly thawed. A 900 µl sample was pelleted by centrifugation at 13,000 rpm (Eppendorf centrifuge 5417 C.) and resuspended in 9001 µl sterile PBS. Bacteria were diluted in sterile PBS to give $1 \times 10^6$ CFU/50 µl and this confirmed by viable counting (as described previously). Mice to be infected were lightly anesthetized with 2.5% v/v isoflourane over oxygen (1.5 L/min) with $NO_2$ (1 L/min), administered using a calibrated vaporizer and anaesthesia confirmed by observing no pinch reflex reaction. Once anesthetized the animals were held with the nose held upright, and pneumococci were introduced intranasally by adding a series of small droplets of the 50 µL inoculum in to the nostril for the mice to involuntarily inhale. After inoculation the mice were laid on their backs until recovery and the viable count of the inoculum was re-determined. Mice were monitored frequently (at least 3 times a day) during the following 14 days for signs of infection. On reaching the pre-determined endpoint (moribund) mice were killed by cervical dislocation and the survival time noted.
Passive Immunization Serum was complement inactivated by incubation at 56° C. for 30 min and was used at a pre-determined dilution. 24 h and 1 h prior to infection, mice were vaccinated by intraperitoneal injection of 200 µl serum. Mice were then infected as previously described. Bacteria were opsonized by incubation in the diluted serum at 37° C. for 1 hr prior to infection. Mice were monitored frequently (at least 3 times a day) during the following 14 days for signs of infection. On reaching the pre-determined endpoint (moribund) mice were sacrificed by cervical dislocation and the survival time noted.

Active Immunization

Mice were randomly arranged in groups of 6 and a blood sample was removed from the tail vein prior 24 h prior to initial vaccination. Vaccines were prepared in a 1:1 ratio in either Freunds complete adjuvant or incomplete adjuvant (Sigma) or Hunter's TiterMax (CytRx Corp., Norcross, Ga.) or Quill A (Accurate Chemical Scientific Corporation, Westbury, N.Y. 11590) as per manufacturers instructions. Normally 50 µg of protein was administered per mouse. 100 µl of vaccine was injected subcutaneously per mouse. Nine days later a blood sample was removed from half of the mice from a tail vein. By staggering this bleed and the next we could bleed all mice prior to vaccination and prior to infection but still monitor immune response during vaccination protocol: this kept us in line with the restrictions on the total number of bleeds/mouse (3) and the minimum time interval between bleeds (14 days). 24 h after sampling blood, vaccination was repeated as previously but if using Freunds, FIA (Freunds incomplete adjuvant) was used. 9 days after boost, a blood sample was removed from those mice not bled before last boost. 24 h later vaccination was repeated as previously. 28 days later a blood sample was removed from the tail vein of all mice. 24 h later mice were infected as previously described with approximately $10^6$ CFU *Streptococcus pneumoniae* D39 or TIGR4. Mice were monitored at least 3 times daily for signs of infection. On reaching the pre-determined endpoint (moribund) mice were sacrificed by cervical dislocation.

Preparation of Mouse Virulent Inoculum

During the course of these experiments, a maximum of 25 mice were used for the production of mouse virulent inocula. The number of times that inocula must be prepared/passaged depended on the virulence and viability of the organisms after prolonged freezing at $-80°$ C.

Infection Experiments

In order to optimize the pneumonia infection model in our laboratory, i.e. to establish the optimal number of organisms that will produce consistent pneumonia with the longest incubation period, we infected groups of 4 mice with 5 different dilutions of organisms from $10^3$, to $10^7$ cfu). We optimized the infection dose required for two heterogeneous strains of *Streptococcus pneumoniae* (D39 and TIGR4). These strains differ in their virulence and antigen characteristics. ($4 \times 5 \times 2 = 40$ mice).

Passive Immunization

For passive immunization with rabbit polyclonal anti-sera, the following sera were tested.
  Pre-immune serum PpmA
  Polyclonal serum PpmA
  6 mice per group; challenged with wild virulent strain of *Streptococcus pneumoniae* and with a strain D39 deleted for PpmA.

TABLE 1

Time Schedule Active immunization

| Week | day | Function | Housing |
|---|---|---|---|
| 0-2 | | Arrival and acclimatization of mice (4 week old) | Normal/group |
| 2 | 0 | Collect pre-immune serum | Normal/group |
| 2 | 1 | Primary vaccination | Normal/group |
| 3 | 10 | $2^{nd}$ serum collection | Normal/group |
| 3 | 11 | $1^{st}$ boost immunization | Normal/group |
| 4 | 20 | $3^{rd}$ serum collection | Normal/group |

TABLE 1-continued

Time Schedule Active immunization

| Week | day | Function | Housing |
|---|---|---|---|
| 4 | 21 | $2^{nd}$ boost immunization | Normal/group |
| 8 | 49 | $4^{th}$ serum collection | Normal/group |
| 9 | 50 | Inoculation | Small cage, filter top |
| 9-11 | 50-64 | Survival time - serum collection - pathology | Small cage, filter top |
| 11 | 64 | Experiment end - serum collection - pathology | Small cage, filter top |

TABLE 2

Time Schedule Passive immunization

| Week | day | Function | Housing |
|---|---|---|---|
| 0-2 | | Arrival and acclimatization of mice (7 week old) | Normal/group |
| 2 | 0 | $1^{st}$ intraperitoneal serum injection | Normal/group |
| 2 | 1 | $2^{nd}$ intraperitoneal serum injection | Normal/group |
| 2 | 1 | Inoculation 1 hour later | Small cage, filter top |
| 2-4 | 1-14 | Survival time - serum collection - pathology | Small cage, filter top |
| 4 | 14 | Experiment end - serum collection - pathology | Small cage, filter top |

TABLE 3

Time Schedule for preparation of inoculum

| Week | day | Function | Housing |
|---|---|---|---|
| 0-2 | | Arrival and acclimatization of mice (7 week old) | Normal/group |
| 2 | 0 | Intraparietal inoculation with $10^5$ cfu | Small cage, filter top |
| 2-3 | 0-7 | Onset of lethargy - terminate - collect blood | Small cage, filter top |
| 3 | 7 | Experiment end | Small cage, filter top |

Results:

Active immunization of CD-1 mice with *Strepococcus pneumoniae* surface protein and infection with a wild type virulent strain of *Streptococcus pneumoniae*.

Immune Protective Potentials of SlrA

SlrA elicited a good protective immune response in the mice, as is shown in table 4 and FIG. 6

TABLE 4

Survival time in hours after active immunization with SlrA
n = 12

| Control | SlrA |
|---|---|
| 49.67 | 53.16 |
| 52.25 | 53.16 |
| 47.34 | 60.33 |
| 44.67 | 200 |
| 47 | 58.83 |
| 43.17 | 146.33 |
| 200 | 53.42 |
| 45.66 | 200 |

TABLE 4-continued

Survival time in hours after active immunization with SlrA
n = 12

| Control | SlrA |
|---|---|
| 200 | 50.17 |
| 52.5 | 47.83 |
| 52.5 | 57.67 |
| 49.83 | 47.58 |

Statistically, a significant difference was found between the vaccinated and the control group concerning the survival time of mice after challenge with virulent *Strepococcus pneumoniae* D39.

| Mann Whitney test |
|---|
| P value     0.0175 |
| Gaussian Approximation P value. |
| P value summary |
| Medians are significantly different (P < 0.05) |
| One-tailed P value |
| Sum of ranks in column A, B     113, 187 |
| Mann-Whitney U     35.00 |

Immune Protective Potentials of IgA1 Proteinase

IgA1 proteinase elicited a good protective immune response in the mice, as is shown in table 5 and FIG. 7

TABLE 5

Survival time in hours after active immunization with IgA1 proteinase (n = 10)

| Control | IgA1 |
|---|---|
| >250 | 47.5 |
| >250 | 49.75 |
| 42.13 | 169.5 |
| 58.33 | 70.75 |
| 47.25 | 168.5 |
| 43.13 | >250 |
| 50.33 | 164.5 |
| 48.33 | >250 |
| 53.33 | 58.42 |
|  | >250 |

Statistically, a significant difference was found between the vaccinated and the control group concerning the survival time of mice after challenge with virulent *Streptococcus pneumoniae* D39.

| Mann Whitney test |
|---|
| P value     0.0474 |
| Gaussian Approximation of P-value |
| P value summary |
| Medians are significantly different (P < 0.05) |
| One-tailed P value. |
| Sum of ranks in column A, B     69, 121 |
| Mann-Whitney U     24.00 |
| Results are shown in FIG. 7. |

Immune Protective Potentials of PsaA

PsaA elicited a good protective immune response in the mice, as is shown in FIG. 8.

Statistically, a significant difference was found between the vaccinated and the control group concerning the survival time after challenge with virulent *Strepococcus pneumoniae* D39.

| Mann Whitney test |
|---|
| P value     0.0409 |
| Gaussian Approximation of P value. |
| P value summary |
| Medians are significantly different (P < 0.05) |
| Sum of ranks in column A, B     195.5, 300.5 |
| Mann-Whitney U     75.50 |

Combination Experiments Vaccinating with at Least one Surface Protein.

Vaccinating with two antigenic proteins resulted in a better survival time in mice after challenge with virulent *Strepococcus pneumoniae* D39 as is shown in table 6, and in FIG. 9.

TABLE 6

Survival time in hours after active immunization with PpmA and SlrA.
N = 12

| PpmA | SlrA | PpmA + SlrA |
|---|---|---|
| 53 | 53.16 | 56.25 |
| 50.34 | 53.16 | 56.25 |
| 43.67 | 60.33 | 50.58 |
| 56.17 | >200 | 56.25 |
| 56.47 | 58.83 | 56.75 |
| 53.5 | 146.33 | 56.75 |
| >200 | 53.42 | 72.17 |
| 57.58 | >200 | >200 |
| 53.58 | 50.17 | 54.67 |
| 58.58 | 47.83 | 72.17 |
| 47.58 | 57.67 | 54.75 |
| 47.58 | 47.58 | 56.67 |

| PpmA vs PpmA + SlrA Mann Whitney test |
|---|
| P value     0.0416 |
| Gaussian Approximation of P value. |
| P value summary |
| Medians are significantly different (P < 0.05) |
| One-tailed P value. |
| Sum of ranks in column A, C     119.5, 180.5 |
| Mann-Whitney U     41.50 |

| SlrA vs PpmA + SlrA Mann Whitney test |
|---|
| P value     0.3325 |
| Gaussian Approximation of P value. |
| P value Summary ns |
| Medians are not significantly different. (P < 0.05) |
| One-tailed P value |
| Sum of ranks in column B, C     142, 158 |
| Mann-Whitney U     64.00 |

Statistically, there was a significant difference between the PpmA and SlrA combined group and the PpmA alone. This shows that protective immunity as a result of vaccination with more than one protein or part thereof is superior to the immunity based on vaccination with only one antigen.

Passive Immunization of CD-1 mice with Anti-PpmA Serum and infection with a PpmA-ve Control Strain Control—mice were vaccinated (2×200 µl) with rabbit-pre immune serum (PIS)

Experiment—mice vaccinated with (2×200 µl) with polyclonal rabbit hyperimmune anti-rPpmA serum (APS).

TABLE 7

Survival time in hours after passive immunization with PpmA-antibodies (APS) or with normal pre-immune serum (PIS)

| PIS D39+ | APS D39+ | PIS PpmA- | APS PpmA- |
| --- | --- | --- | --- |
| 59.00 | 113.67 | 47.17 | 118.33 |
| 59.00 | 40.67 | 51.67 | 118.33 |
| 65.00 | 63.17 | 59.67 | 65.82 |
| 65.00 | 59.17 | 48.67 | 65.82 |
| 59.00 | 90.17 | 90.67 | 59.82 |
| 46.25 | 59.17 | 38.17 | 72.82 |
| 59.00 | 59.17 | >200 | 46.82 |
| 46.50 | 63.17 | 38.5 | 51.82 |
| 46.25 | >200 | >200 | 65.82 |
| 46.75 | 48.17 | 61 | 46.82 |

Passive Immunization Experiment
Mice Infected Intranasally with *Strepococcus pneumoniae* D39

| Mann Whitney test | |
| --- | --- |
| P value | 0.0376 |
| Exact P value | |
| P value summary | * |
| Medians significantly different (P < 0.05) | |
| One-tailed P value | |
| Sum of ranks in column A, B | 81, 129 |
| Mann-Whitney U | 26.00 |

Passive immunization Experiment.
Mice Infected Intranasally with *Strepococcus pneumoniae* D39 ppmA-mutant

| Mann Whitney test | |
| --- | --- |
| P value | 0.2644 |
| Exact P value | |
| P value summary | ns |
| Medians are not significantly different (P < 0.05) | |
| One-tailed P value | |
| Sum of ranks in column C, D | 96, 114 |
| Mann-Whitney U | 41.00 |

The results in table 7 and in FIG. 10 clearly show the protective effect of passive immunization with anti PpmA antibodies against a challenge infection with virulent streptococcal strain D39. They also show that the protection is much less against a streptococcal strain that is deleted for PpmA. The ppmA-ve D39 strain has been previously shown to be less virulent than D39.

TABLE 8

Survival time in hours after passive immunization with PpmA in MF-1 mice

| Treatment | Survival times (h) |
| --- | --- |
| Normal rabbit serum (NRS) | 41, 48, 48, 65, 72 |
| Bacteria opsonised in NRS | 48, 48, 65, 72, 89 |

TABLE 8-continued

Survival time in hours after passive immunization with PpmA in MF-1 mice

| Treatment | Survival times (h) |
| --- | --- |
| Anti-PpmA anti-serum | 71, 71, 113.5, 113.5, 137, 336, 336, 336, 336, 336 |
| Bacteria opsonised in anti-PpmA | 89, 143, 336, 336, 336 |

The results in table 8 and in FIG. 11 clearly show the protection against challenge infection after a passive immunization.

EXAMPLE 3

In Silico Search

The nucleotide sequence of PpmA was determined to search databases

The gene for PpmA was amplified by PCR from *Streptococcus pneumoniae* D39 with the primers 5' CCATG-GCTAGCCACCATCACCATCACCATTC-GAAAGGGTCAGAAGGTGC 3' (SEQ ID NO: 60) and 5' TCATGGATCCGGACTATTCGTTTGATGTAC3' (SEQ ID NO: 61) which incorporate flanking NheI and BamHI restriction sites, and a N-terminal HiS $^6$ tag. The amplified DNA was cloned into a pET11a expression vector (Stratagene, LaJolla, Calif.) and electrotransformed into *E. coli* BL21(DE3). The recombinant protein was purified by Ni $^+$ affinity chromatography with the HisTrap Kit (Amersham Pharmacia) according to the manufacturers recommendations.

The purified recombinant protein was dialysed against 10 mM HEPES buffer, pH 7.5, freeze dried, and stored at −20° C.

PpmA
ppmA nucleotide sequence *Streptococcus pneumoniae* D39

(SEQ ID NO: 39)
ATGAAGAAAAAATTATTGGCAGGTGCCATCACACTATTATCAGTAGCAAC

TTTAGCAGCTTGTTCGAAAGGGTCAGAAGGTGCAGACCTTATCAGCATGA

AAGGGGATGTCATTACAGAACATCAATTTTATGAGCAAGTGAAAAGCAAC

CCTTCAGCCCAACAAGTCTTGTTAAATATGACCATCCAAAAAGTTTTTGA

AAAACAATATGGCTCAGAGCTTGATGATAAAGAGGTTGATGATACTATTG

CCGAAGAAAAAAACAATATGGCGAAAACTACCAACGTGTCTTGTCACAA

GCAGGTATGACTCTTGAAACACGTAAAGCTCAAATTCGTACAAGTAAATT

AGTTGAGTTGGCAGTTAAGAAGGTAGCAGAAGCTGAATTGACAGATGAAG

CCTATAAGAAAGCCTTTGATGAGTACACTCCAGATGTAACGGCTCAAATC

ATCCGTCTTAATAATGAAGATAAGGCCAAAGAAGTTCTCGAAAAAGCCAA

GGCAGAAGGTGCTGATTTTGCTCAATTAGCCAAAGATAATTCAACTGATG

AAAAAACAAAAGAAAATGGTGGAGAAATTACCTTTGATTCTGCTTCAACA

GAAGTACCTGAGCAAGTCAAAAAAGCCGCTTTCGCTTTAGATGTGGATGG

TGTTTCTGATGTGATTACAGCAACTGGCACACAAGCCTACAGTAGCCAAT

ATTACATTGTAAAACTCACTAAGAAAACAGAAAAATCATCTAATATTGAT

GACTACAAAGAAAATTAAAAACTGTTATCTTGACTCAAAAACAAAATGA

TTCAACATTTGTTCAAAGCATTATCGGAAAAGAATTGCAAGCAGCCAATA

TCAAGGTTAAGGACCAAGCCTTCCAAAATATCTTTACCCAATATATCGGT

```
GGTGGAGATTCAAGCTCAAGCAGTAGTACATCAAACGAATAG

PpmA amino acid sequence
                                        (SEQ ID NO: 40)
MKKKLLAGAITLLSVATLAACSKGSEGADLISMKGDVITEHQFYEQVKSN

PSAQQVLLNMTIQKVFEKQYGSELDDKEVDDTIAEEKKQYGENYQRVLSQ

AGMTLETRKAQIRTSKLVELAVKKVAEAELTDEAYKKAFDEYTPDVTAQI

IRLNNEDKAKEVLEKAKAEGADFAQLAKDNSTDEKTKENGGEITFDSAST

EVPEQVKKAAFALDVDGVSDVITATGTQAYSSQYYIVKLTKKTEKSSNID

DYKEKLKTVILTQKQNDSTFVQSIIGKELQAANIKVKDQAFQNIFTQYIG

GGDSSSSSSTSNE*

Recombinant His tagged PpmA
                                        (SEQ ID NO: 41)
MAHHHHHHSKGSEGADLISMKGDVITEHQFYEQVKSNPSAQQVLLNMTIQ

KVFEKQYGSELDDKEVDDTIAEEKKQYGENYQRVLSQAGMTLETRKAQIR

TSKLVELAVKKVAEAELTDEAYKKAFDEYTPDVTAQIIRLNNEDKAKEVL

EKAKAEGADFAQLAKDNSTDEKTKENGGEITFDSASTEVPEQVKKAAFAL

DVDGVSDVITATGTQAYSSQYYIVKLTKKTEKSSNIDDYKEKLKTVILTQ

KQNDSTFVQSIIGKELQAANIKVKDQAFQNIFTQYIGGGDSSSSSSTSNE
```

SlrA

The gene for the active peptide of SirA was amplified by PCR from *Strepococcus pneumoniae* D39 with the primers 5'TTTACTGCATATGCACCATCACCATCAC-CATAGCAGCGTCCAACGCAGT3' (SEQ ID NO: 42) and 5'CATTAGGATCCAATCGCTGGGGAAGTG3' (SEQ ID NO: 43) which incorporate flanking NdeI and BamHI restriction sites, and a N-terminal His [6] tag. The amplified DNA was cloned into a pET11a expression vector (Stratagene, LaJolla, Calif.) and electrotransformed into *E. coli* BL21(DE3). The recombinant protein was purified by Ni+ affinity chromatography with the HisTrap Kit (Amersham Pharmacia) according to the manufacturers recommendations. The purified recombinant protein was dialysed against 10 mM HEPES buffer, pH7.5, freeze dried, and stored at –20° C.

```
SlrA
slrA nucleotide sequence Streptococcus pneumoniae
D39
                                        (SEQ ID NO: 44)
ATGAAAAAACTAGCAACCCTTCTTTTACTGTCTACTGTAGCCCTAGCTGG

GTGTAGCAGCGTCCAACGCAGTCTGCGTGGTGATGATTATGTTGATTCCA

GTCTTGCTGCTGAAGAAAGTTCCAAAGTAGCTGCCCAATCTGCCAAGGAG

TTAAACGATGCTTTAACAAACGAAAACGCCAATTTCCCACAACTATCTAA

GGAAGTTGCTGAAGATGAAGCCGAAGTGATTTTCCACACAAGCCAAGGTG

ATATTCGCATTAAACTCTTCCCTAAACTCGCTCCTCTAGCGGTTGAAAAT

TTCCTCACTCACGCCAAAGAAGGCTACTATAACGGTATTACCTTCCACCG

TGTCATCGATGGCTTTATGGTCCAAACTGGAGATCCAAAAGGGGACGGTA

CAGGTGGTCAGTCCATCTGGCATGACAAGGATAAGACTAAAGACAAAGGA

ACTGGTTTCAAGAACGAGATTACTCCTTATTTGTATAACATCCGTGGTGC

TCTTGCTATGGCTAATACTGGTCAACCAAACACCAATGGCAGCCAGTTCT

TCATCAACCAAAACTCTACAGATACCTCTTCTAAACTCCCTACAAGCAAG

TATCCACAGAAAATTATTGAAGCCTACAAAGAAGGTGGAAACCCTAGTCT

AGATGGCAAACACCCAGTCTTTGGTCAAGTGATTGACGGTATGGATGTTG

TGGATAAGATTGCTAAGGCCGAAAAAGATGAAAAAGACAAGCCAACTACT

GCTATCACAATCGACAGCATCGAAGTGGTGAAAGACTACGATTTTAAATC

TTAA

SlrA amino acid sequence
                                        (SEQ ID NO: 45)
MKKLATLLLLSTVALAGCSSVQRSLRGDDYVDSSLAAEESSKVAAQSAKE

LNDALTNENANFPQLSKEVAEDEAEVIFHTSQGDIRIKLFPKLLAPLAVE

NFLTHAKEGYYNGITFHRVIDGFMVQTGDPKGDGTGGQSIWHDKDKTKDK

GTGFKNEITPYLYNIRGALAMANTGQPNTNGSQFFINQNSTDTSSKLPTS

KYPQKILEAYKEGGNPSLDGKHPVFGQVIDGMDVVDKIAKAEKDEKDKPT

TAITIDSIEVVKDYDFKS

Recombinant His tagged SlrA
                                        (SEQ ID NO: 46)
MAHHHHHHSSVQRSLRGDDYVDSSLAAEESSKVAAQSAKELNDALTNENA

NFPQLSKEVAEDEAEVIFHTSQGDIRIKLFPKLAPLAVENFLTHAKEGYY

NGITFHRVIDGFMVQTGDPKGDGTGGQSIWHDKDKTKDKGTGFKNEITPY

LYNIRGALAMANTGQPNTNGSQFFINQNSTDTSSKLPTSKYPQKIIEAYK

EGGNPSLDGKHPVFGQVIDGMDVVDKIAKAEKDEKDKPTTAITIDSIEVV

KDYDFKS
```

Expression and Purification of His[6]rIgA1 Proteinase

A 3948 bp gene fragment which encodes amino acids 671-1987 of the IgA1 proteinase was amplified by PCR from *Strepococcus pneumoniae* TIGR4 with the primers 5'CAA-CATCACATATGGGACAAACAGAACCAGAG3' (SEQ ID NO: 47) and 5'ACTTAGATCTTAATGATGGTGGTGAT-GATGGGCTTTAAAGATTGCTCTC3' (SEQ ID NO: 48) which incorporate flanking NdeI and BglII restriction sites, and a C-terminal His [6] tag. The amplified DNA was cloned into a pET11a expression vector (Stratagene, LaJolla, Calif.) and electrotransformed into *E. coli* BL21(DE3).

Inoculate 200 ml LB broth with 50 μl/ml ampicillin and grow at 37° C. overnight.

Transfer 20-30 ml per liter of the overnight culture to prewarmed LB with 50 μl/ml ampicillin and grow to an OD$_{600}$ between 0.6 and 1.0 (2-3 hours).

Expression is induced by the addition of 1 mm IPTG (10 ml of a 100 mM stock/liter), and the cells were grown for a further 2-3hours.

Cells were harvested (10 min @ 3000 rpm) and resuspended in ice cold 20 mM sodium phosphate buffer pH7.4 with 8M urea (15 ml of buffer/liter of culture).

The cells are lysed by sonication 3×30 seconds on ice (1 min intervals to allow cooling).

Place lysate on a rotating shaker at 4° C. for 20 min (to dissolve inclusion bodies).

The crude lysate is cleared by centrifugation (15,000 rpm for 30 min in a JA20 rotor).

Place the cleared supernatant in a pre-boiled dialysis bag, and dialyze overnight against 2 L ice cold 20 mM sodium phosphate buffer pH7.4 with 1 mM DTT.

Add ammonium sulfate to the dialyses supernatant to 20% saturation (0.123 g/ml), and stir at 4° C. for 20 min.

Spin precipitate at 10,000 rpm for 15 min in a JA20 rotor at 4° C. (IgA1 proteinase will be recovered from the protein pellet).

Redisolve protein pellet (5 ml/liter culture) in start buffer (2 mM sodium phosphate buffer pH7.4, 0.5M NaCl ,10 mM imidazole 8M urea).

Filter through a 0.45 μm filter.

Load 1 ml column with Ni+ and equilibrate it with start buffer with urea.

Pump the supernatant (15 ml) through a Ni+ loaded 1 ml HisTrap column (Amersham Pharmacia).

Wash with 10 ml wash buffer (20 mM sodium phosphate buffer pH7.4, 0.5M NaCl , 20 mM imidazole 8M urea).

Elute in 1 ml fractions with elution (20 mM sodium phosphate buffer pH7.4; 0.5M NaCl; 400 mM imidazole; 8M urea).

The second fraction should contain the IgA1 proteinase.

The $2^{nd}$ fraction is then dialyzed overnight against 2 L 10 mM Hepes buffer pH7.4.

Without the Urea, the protein will re-precipitate. Recover the protein by centrifugation, Freeze dry and store at −20° C.

Protein can be resolubilized in 8M urea and then diluted in PBS etc. It will remain soluble at high concentrations in 4M urea.

```
Immunoglobulin A1 protease (iga) nucleotide
sequence [Streptococcus pneumoniae TIGR4]
                                       (SEQ ID NO: 49)
ATGGAAAAGTATTTTGGTGAAAAACAAGAGCGTTTTTCATTTAGAAAATT
ATCAGTAGGACTTGTATCTGCAACGATTTCAAGTTTATTTTTTATGTCTG
TATTAGCTAGTTCATCTGTGGATGCTCAAGAAACTGCGGGAGTTCACTAT
AAATATGTGGCAGATTCAGAGCTATCATCAGAAGAAAAGAAGCAGCTTGT
CTATGATATTCCGACATACGTGGAGAATGATGATGAAACTTATTATCTTG
TTTATAAGTTAAATTCTCAAAATCAACTGGCGGAATTGCCAAATACTGGA
AGCAAGAATGAGAGGCAAGCCCTAGTTGCTGGTGCTAGCTTAGCTGCTAT
GGGAATTTTAATTTTTGCTGTTTCCAAGAAAAAGGTTAAGAATAAAACGG
TATTACATTTAGTATTGGTTGCAGGGATAGGAAATGGTGTCTTAGTTTCA
GTCCATGCTTTAGAAAATCATCTTTTGCTAAATTACAATACGGACTATGA
ATTGACCTCTGGAGAAAAATTACCTCTTCCTAAAGAGATTTCAGGTTACA
CTTATATTGGATATATCAAAGAGGGAAAAACGACTTCTGAGTCTGAAGTA
AGTAATCAAAAGAGTTCAGTTGCCACTCCTACAAAACAACAAAAGGTGGA
TTATAATGTTACACCGAATTTTGTAGACCATCCATCAACAGTACAAGCTA
TTCAGGAACAAACACCTGTTTCTTCAACTAAGCCGACAGAAGTTCAAGTA
GTTGAAAAACCTTTCTCTACTGAATTAATCAATCCAAGAAAAGAAGAGAA
ACAATCTTCAGATTCTCAAGAACAATTAGCCGAACATAAGAATCTAGAAA
CGAAGAAAGAGGAGAAGATTTCTCCAAAAGAAAAGACTGGGGTAAATACA
TTAAATCCACAGGATGAAGTTTTATCAGGTCAATTGAACAAACCTGAACT
CTTATATCGTGAGGAAACTATGGAGACAAAAATAGATTTTCAAGAAGAAA
TTCAAGAAATCCTGATTTAGCTGAAGGAACTGTAAGAGTAAAACAAGAA
GGTAAATTAGGTAAGAAAGTTGAAATCGTCAGAATATTCTCTGTAAACAA
GGAAGAAGTTTCGCGAGAAATTGTTTCAACTTCAACGACTGCGCCTAGTC
CAAGAATAGTCGAAAAAGGTACTAAAAAAACTCAAGTTATAAAGGAACAA
CCTGAGACTGGTGTAGAACATAAGGACGTACAGTCTGGAGCTATTGTTGA
ACCCGCAATTCAGCCTGAGTTGCCCGAAGCTGTAGTAAGTGACAAAGGCG
AACCAGAAGTTCAACCTACATTACCCGAAGCAGTTGTGACCGACAAAGGT
GAGACTGAGGTTCAACCAGAGTCGCCAGATACTGTGGTAAGTGATAAAGG
TGAACCAGAGCAGGTAGCACCGCTTCCAGAATATAAGGGTAATATTGAGC
AAGTAAAACCTGAAACTCCGGTTGAGAAGACCAAAGAACAAGGTCCAGAA
AAAACTGAAGAAGTTCCAGTAAAACCAACAGAAGAAACACCAGTAAATCC
AAATGAAGGTACTACAGAAGGAACCTCAATTCAAGAAGCAGAAAATCCAG
TTCAACCTGCAGAAGAATCAACAACGAATTCAGAGAAAGTATCACCAGAT
ACATCTAGCAAAAATACTGGGGAAGTGTCCAGTAATCCTAGTGATTCGAC
AACCTCAGTTGGAGAATCAAATAAACCAGAACATAATGACTCTAAAAATG
AAAATTCAGAAAAAACTGTAGAAGAAGTTCCAGTAAATCCAAATGAAGGC
ACAGTAGAAGGTACCTCAAATCAAGAAACAGAAAAACCAGTTCAACCTGC
AGAAGAAACACAAACAAACTCTGGGAAAATAGCTAACGAAAATACTGGAG
AAGTATCCAATAAACCTAGTGATTCAAAACCACCAGTTGAAGAATCAAAT
CAACCAGAAAAAAACGGAACTGCAACAAAACCAGAAAATTCAGGTAATAC
AACATCAGAGAATGGACAAACAGAACCAGAACCATCAAACGGAAATTCAA
CTGAGGATGTTTCAACCGAATCAAACACATCCAATTCAAATGGAAACGAA
GAAATTAAACAAGAAAATGAACTAGACCCTGATAAAAAGGTAGAAGAACC
AGAGAAAACACTTGAATTAAGAAATGTTTCCGACCTAGAGTTATACAGTT
TGTCAAATGGTACTTATAAACAACACATTTCGTTAGAGCAAGTTCCAAGC
AATCCAAATAGCTACTTTGTTAAAGTGAAATCTTCTTCATTCAAAGATGT
ATACCTACCAGTAGCATCAATATCAGAGGAAAGAAAAAATGATAAAATCC
TTTATAAAATCACAGCAAAAGTAGAGAAGCTTCAGCAGGAGATAGAAAGC
AGATATAAAGATAATTTTACCTTCTATCTAGCTAAGAAGGGAACAGAAGA
AACAACAAACTTTACTTCCTTTAGTAATCTGGTCAAAGCTATAAACCAAA
ATCCCTCTGGAACCTATCATTTAGCGGCCAGCCTGAATGCTAACGAAGTG
GAGCTTGGTCCTGATGAAAGATCCTATATCAAGGACACCTTTACTGGTCG
TTTAATCGGTGAAAAAGATGGCAAGAATTATGCTATCTATAATTTGAAAA
AACCTCTGTTTGAAAACTTGAGTGGTGCTACAGTAGAAAAACTGAGTCTA
AAAAATGTTGCTATTTCAGGGAAAGATGATATCGGTTCACTGGCAAATGA
AGCTCAGAATAACACAAAAATTAAGCAAGTTCACGTCGATGGTGTTCTGG
CTGGTGAACGTGGTATCGGTGGTTTGCTGGCTAAGGCTGAGCAATCAAGC
ATCACAGAGCAGTTTCAAGGGAAGAATTATCAACACTTATGAAACGAC
TGCTGCCTACAATATCGGTGGTATGGTCGGTCATTTGACAGGTGACAAGG
CTTTACTTACTAAGTCAAAAGCGACAGTAGCCATTTCATCTAACACAAAT
ACTTCAGATCAGACTGTGGGTGGACTTGCAGGCCTAGTAGACCGAGATGC
ACAGATCCAAGATAGCTATGCTGAAGGTGATATCAACAATGTCAAGCACT
TTGGTAGAGTCGCTGGAGTGGCAGGCAATTTGTGGGATCGAACTTCTGGT
GATGTTAGGCATGCTGGAAGTTTGACCAATGTTCTCAGCGATGTTAATGT
AACCAACGGAAATGCCATCACTGGTTACCACTATAACGAAATGAAGGTAA
AGGACACATTCAGCAGCAAGGCCAACAGAGTCTACAATGTCACCTTGGTC
```

```
AAGGATGAGGTCGTCAGCAAGGAATCCTTTGAAGAAAGAGGAACAATGCT
AGATGCTTCTCAAATTGCAAGCAAAAAAGCAGAAATCAATCCTCTCATTT
TACCAACAGTGGAGCCACTTTCAACAAGTGGCAAAAAAGACAGTGATTTT
TCTAAGGTGGCCTATTATCAAGCTAAGCGCAACTTGACTTATAAAACAT
TGAAAAATTGCTACCTTTCTACAACAAGGCAACCATCGTCAAATACGGAA
ACCTGGTCAATGAGAACAGTCTTTTATATCAAAAGAACTCTTGTCAGCA
GTCATGATGAAGGACAACCAAGTCATCACAGACATTGTTTCTAACAAACA
GACTGCAAACAAACTCTTGCTTCACTACAAGGATGATTTATCTGAGAAGC
TGGATCTCAAATACCAGAATGATTTCGCCAAATTAGCAGAATATAGTCTG
GGCAATACTGGACTTCTCTATACGCCAAACCAATTCCTGTATGACCAAAC
CTCTATCATCAAGCAAGTCTTACCTGACTTACAAAAGGTTGACTATCATT
CAGAAGCCATCAGAAAGACGCTGGGTATTTCTCCAAACGTCAAGCAAACT
GAGCTCTATCTAGAAGACCAGTTCGCCAAAACAAAACAACAACTGGAAGA
CAGTTTGAAAAAACTCTTGTCAGCGGATGCTGGACTGGCTAGTGCTAACC
CCGTCACTGAAGGTTATCTTGTAGATAAAATCAAACGCAACAAGGAAGCC
TTGCTACTTGGCTTGACCTATCTGGAACGGTGGTATAACTTTAGCTATGG
TCAGGTGAATGTCAAAGACCTAGTTCTGTACCATTTGGACTTCTTTGGTA
AGGGGAATGCTTCACCATTAGATACTCTGATTGAGTTGGGTAAATCTGGC
TTTAACAATCTTCTAGCTAAGAATAATGTCGATACTTATGGTATCAGTCT
TGCCAGTCAACATGGAACGACAGATTTGTTTAGCACGCTGGAACATTACC
GAAAAGTCTTTTTACCAAATACAAGCAATAATGACTGGTTTAAATCAGAG
ACTAAGGCTTACATTGTCGAAGAAAAATCCACTATCGAAGAGGTGAAAAC
GAAGCAAGGGTTAGCTGGCACCAAGTATTCTATCGGTGTTTATGATCGTA
TCACGAGTGCCACATGGAAATACCGCAATATGGTCTTGCCTCTCCTGACC
TTGCCAGAGAGATCCGTATTTGTCATCTCGACCATGTCTAGTCTAGGATT
TGGAGCTTATGATCGCTACCGCAGTAGTGACCATAAAGCGGGCAAGGCTC
TCAATGATTTTGTTGAAGAAATGCGCGTGAAACAGCCAAACGTCAGCGA
GATCACTACGATTATTGGTATCGTATTTTAGACGACAATGCACGTGAAAA
ACTTTATAGAAATATTTGCTTTACGATGCTTATAAATTTGGCGATGATA
ATACCGTAGGGAAAGCTACAGAAGTGGCAGATTTTGATAATCCAAATCCT
GCAATGCAACATTTCTTTGGACCTGTTGGAAATAAGTTGGGCATAATCA
ACACGGTGCTTATGCTACAGGTGATGCAGTTTATTATATGGGTTATCGAA
TGTTGGATAAGGATGGAGCTATTACTTATACGCATGAGATGACACATGAC
TCAGATCAGGACATTTATCTTGGAGGATATGGTCGAAGAAGTGGCTTGGG
ACCAGAGTTCTTTGCTAAAGGATTATTACAAGCACCAGACCATCCAGATG
ATGCGACCATTACCATCAACTCCATCTTGAAACATTCAAAATCTGATAGT
ACAGAAAGTCGACGATTACAAGTACTTGATCCAACTACAAGATTTAATAA
TGCAGATGATTTGAAGCAATATGTCCACAACATGTTTGACGTTGTTTATA
TGTTGGAATATCTCGAAGGAAATTCAATTCTTAAATTGGATACGAATCAA
AAACAACAACTTCTTAGAAAAGTTACAAATGAGTACCATCCTGATCCTGA
TGGAAATAAGGTCTATGCAACAAATGTTGTCAGAAATCTAACAGTAGAAG
AAGTTGAAAGACTACGTTCATTCAATGATTTGATTGATAATAATATTCTT
TCGTCTAGGGAATATGCCTCAGGTAAATACGAAAGAAATGGCTACTTCAC
TATTAAGTTATTTGCACCGATTTATGCTGCATTAAGTAATGATATAGGAA
CACCAGGTGACCTGATGGGACGTCGTATAGCCTATGAACTACTAGCTGCT
AAAGGCTTTAAAGATGGTATGGTACCATATATCTCAAACCAATACGAAGA
AGAAGCCAAACAAAGGGCAAGACAATCAATCTCTACGGTAAAACAAGAG
GTTTGGTTACAGATGACTTGGTTTTGGAAAAGGTATTTAATAACCAATAT
CATACTTGGAGTGAGTTTAAGAAAGCTATGTATCAAGAACGACAAGATCA
GTTTGATAGATTGAACAAAGTTACTTTTAATGATACAACACAGCCTTGGC
AAACATTTGCCAAGAAAACTACAAGCAGTGTAGATGAATTACAGAAATTA
ATGGACGTTGCTGTTCGTAAGGATGCAGAACACAATTACTACCATTGGAA
TAACTACAATCCAGACATAGATAGTGAAGTCCACAAGCTCAAGAGAGCAA
TCTTTAAAGCCTATCTTGACCAAACAAATGATTTTAGAAGTTCAATTTTT
GAGAATAAAAAATAG
```

Amino Acid sequence Iga (SEQ ID NO: 51)
MEKYFGEKQERFSFRKLSVGLVSATISSLFFMSVLASSSVDAQETAGVHY
KYVADSELSSEEKKQLVYDIPTYVENDDETYYLVYKLNSQNQLAELPNTG
SKNERQALVAGASLAAMGILIFAVSKKKVKNKTVLHLVLVAGIGNGVLVS
VHALENHLLLNYNTDYELTSGEKLPLPKEISGYTYIGYIKEGKTTSESEV
SNQKSSVATPTKQQKVDYNVTPNFVDHPSTVQAIQEQTPVSSTKPTEVQV
VEKPFSTELINPRKEEKQSSDSQEQLAEHKNLETKKEEKISPKEKTGVNT
LNPQDEVLSGQLNKPELLYREETMETKIDFQEEIQENPDLAEGTVRVKQE
GKLGKKVEIVRIFSVNKEEVSREIVSTSTTAPSPRIVEKGTKKTQVIKEQ
PETGVEHKDVQSGAIVEPAIQPELPEAVVSDKGEPEVQPTLPEAVVTDKG
ETEVQPESPDTVVSDKGEPEQVAPLPEYKGNIEQVKPETPVEKTKEQGPE
KTEEVPVKPTEETPVNPNEGGTTEGTSIQEAENPVQPAEESTTNSEKVSPD
TSSKNTGEVSSNPSDSTTSVGESNKPEHNDSKNENSEKTVEEVPVNPNEG
TVEGTSNQETEKPVQPAEETQTNSGKIANENTGEVSNKPSDSKPPVEESN
QPEKNGTATKPENSGNTTSENGQTEPEPSNGNSTEDVSTESNTSNSNGNE
EIKQENELDPDKKVEEPEKTLELRNVSDLELYSLSNGTYKQHISLEQVPS
NPNSYFVKVKSSSFKDVYLPVASISEERKNDKILYKITAKVEKLQQEIES
RYKDNFTFYLAKKGTEETTNFTSFSNLVKAINQNPSGTYHLAASLNANEV
ELGPDERSYIKDTFTGRLIGEKDGKNYAIYNLKKPLFENLSGATVEKLSL
KNVAISGKDDIGSLANEAQNNTKIKQVHVDGVLAGERGIGGLLAKAEQSS
ITESSFKGRIINTYETTAAYNIGGMVGHLTGDKALLTKSKATVAISSNTN
TSDQTVGGLAGLVDRDAQIQDSYAEGDINNVKHFGRVAGVAGNLWDRTSG
DVRHAGSLTNVLSDVNVTNGNAITGYHYNEMKVKDTFSSKANRVYNVTLV
KDEVVSKESFEERGTMLDASQIASKKAEINPLILPTVEPLSTSGKKDSDF
SKVAYYQAKRNLTYKNIEKLLPFYNKATIVKYGNLVNENSLLYQKELLSA
VMMKDNQVITDIVSNKQTANKLLLHYKDDLSEKLDLKYQNDFAKLAEYSL

GNTGLLYTPNQFLYDQTSIIKQVLPDLQKVDYHSEAIRKTLGISPNVKQT

ELYLEDQFAKTKQQLEDSLKKLLSADAGLASANPVTEGYLVDKIKRNKEA

LLLGLTYLERWYNFSYGQVNVKDLVLYHLDFFGKGNASPLDTLIELGKSG

FNNLLAKNNVDTYGISLASQHGTTDLFSTLEHYRKVFLPNTSNNDWFKSE

TKAYIVEEKSTIEEVKTKQGLAGTKYSIGVYDRITSATWKYRNMVLPLLT

LPERSVFVISTMSSLGFGAYDRYRSSDHKAGKALNDFVEENARETAKRQR

DHYDYWYRILDDNAREKLYRNILLYDAYKFGDDNTVGKATEVADFDNPNP

AMQHFFGPVGNKVGHNQHGAYATGDAVYYMGYRMLDKDGAITYTHEMTHD

SDQDIYLGGYGRRSGLGPEFFAKGLLQAPDHPDDATITINSILKHSKSDS

TESRRLQVLDPTTRFNNADDLKQYVHNMFDVVYMLEYLEGNSILKLDTNQ

KQQLLRKVTNEYHPDPDGNKVYATNVVRNLTVEEVERLRSFNDLIDNNIL

SSREYASGKYERNGYFTIKLFAPIYAALSNDIGTPGDLMGRRIAYELLAA

KGFKDGMVPYISNQYEEEAKQKGKTINLYGKTRGLVTDDLVLEKVFNNQY

HTWSEFKKAMYQERQDQFDRLNKVTFNDTTQPWQTFAKKTTSSVDELQKL

MDVAVRKDAEHNYYHWNNYNPDIDSEVHKLKRAIFKAYLDQTNDFRSSIF

ENKK

Recombinant His Tagged Iga
MGQTEPEPSNGNSTEDVSTESNTSNSNGNEEIKQENELDPDKKVEEPEKT

LELRNVSDLELYSLSNGTYKQHISLEQVPSNPNSYFVKVKSSSFKDVYLP

VASISEERKNDKILYKITAKVEKLQQEIESRYKDNFTFYLAKKGTEETTN

FTSFSNLVKAINQNPSGTYHLAASLNANEVELGPDERSYIKDTFTGRLIG

EKDGKNYAIYNLKKPLFENLSGATVEKLSLKNVAISGKDDIGSLANEAQN

NTKIKQVHVDGVLAGERGIGGLLAKAEQSSITESSFKGRIINTYETTAAY

NIGGMVGHLTGDKALLTKSKATVAISSNTNTSDQTVGGLAGLVDRDAQIQ

DSYAEGDINNVKHFGRVAGVAGNLWDRTSGDVRHAGSLTNVLSDVNVTNG

NAITGYHYNEMKVKDTFSSKANRVYNTLVKDEVVSKESFEERGTMLDASQ

IASKKAEINPLILPTVEPLSTSGKKDSDFSKVAYYQAKRNLTYKNIEKLL

PFYNKATIVKYGNLVNENSLLYQKELLSAVMMKDNQVITDIVSNKQTANK

LLLHYKDDLSEKLDLKYQNDFAKLAEYSLGNTGLLYTPNQFLYDQTSIIK

QVLPDLQKVDYHSEAIRKTLGISPNVKQTELYLEDQFAKTKQQLEDSLKK

LLSADAGLASANPVTEGYLVDKIKRNKEALLLGLTYLERWYNFSYGQVNV

KDLVLYHLDFFGKGNASPLDTLIELGKSGFNNLLAKNNVDTYGISLASQH

GTTDLFSTLEHYRKVFLPNTSNNDWFKSETKAYIVEEKSTIEEVKTKQGL

AGTKYSIGVYDRITSATWKYRNMVLPLLTLPERSVFVISTMSSLGFGAYD

RYRSSDHKAGKALNDFVEENARETAKRQRDHYDYWYRILDDNAREKLYRN

ILLYDAYKFGDDNTVGKATEVADFDNPNPAMQHFFGPVGNKVGHNQHGAY

ATGDAVYYMGYRMLDKDGAITYTHEMTHDSDQDIYLGGYGRRSGLGPEFF

AKGLLQAPDHPDDATITINSILKHSKSDSTESRRLQVLDPTTRFNNADDL

KQYVHNMFDVVYMLEYLEGNSILKLDTNQKQQLLRKVTNEYHPDPDGNKV

YATNVVRNLTVEEVERLRSFNDLIDNNILSSREYASGKYERNGYFTIKLF

APIYAALSNDIGTPGDLMGRRIAYELLAAKGFKDGMVPYISNQYEEEAKQ

KGKTINLYGKTRGLVTDDLVLEKVFNNQYHTWSEFKKAMYQERQDQFDRL

NKVTFNDTTQPWQTFAKKTTSSVDELQKLMDVAVRKDAEHNYYHWNNYNP

DIDSEVHKLKRAIFKAHHHHHH

PsaA

The gene for PsaA was amplified by PCR from *Strepococcus pneumoniae* D39 with the primers 5'CCATGGCTAGC-CACCATCACCATCACCATGCTACAAACT-CAATCATCGC 3' (SEQ ID NO: 52) and 5'TTTCGGATCCTTATTTGCCAATCCTTCAGC 3' (SEQ ID NO: 53) which incorporate flanking NheI and BamHI restriction sites, and a N-terminal His6 tag. The amplified DNA was cloned into a pET11a expression vector (Stratagene, LaJolla, Calif.) and electrotransformed into *E. coli* BL21(DE3). The recombinant protein was purified by Ni$^+$ affinity chromatography with the HisTrap Kit (Amersham Pharmacia) according to the manufacturers recommendations. To prevent the formation of inclusion bodies, 8 M urea was added to all buffers throughout the purification process. The purified recombinant protein was dialysed against 10 mM HEPES buffer, pH7.5, free dried, and stored at −20° C.

psaA nucleotide sequence *Streptococcus pneumoniae* D39
(SEQ ID NO: 54)
ATGAAAAAATTAGGTACATTACTCGTTCTCTTTCTTTCTGCAATCATTCT

TGTAGCATGTGCTAGCGGAAAAAAGATACAACTTCTGGTCAAAAACTAA

AAGTTGTTGCTACAAACTCAATCATCGCTGATATTACTAAAAATATTGCT

GGTGACAAAATTGACCTTCATAGTATCGTTCCGATTGGGCAAGACCCACA

CGAATACGAACCACTTCCTGAAGACGTTAAGAAAACTTCTGAGGCTGATT

TGATTTTCTATAACGGTATCAACCTTGAAACAGGTGGCAATGCTTGGTTT

ACAAAATTGGTAGAAAATGCCAAGAAAACTGAAAACAAAGACTACTTCGC

AGTCAGCGACGGCGTTGATGTTATCTACCTTGAAGGTCAAAATGAAAAAG

GAAAAGAAGACCCACACGCTTGGCTTAACCTTGAAAACGGTATTATTTTT

GCTAAAAATATCGCCAAACAATTGAGCGCCAAAGACCCTAACAATAAAGA

ATTCTATGAAAAAAATCTCAAAGAATATACTGATAAGTTAGACAAACTTG

ATAAAGAAAGTAAGGATAAATTTAATAAGATCCCTGCTGAAAAGAAACTC

ATTGTAACCAGCGAAGGAGCATTCAAATACTTCTCTAAAGCCTATGGTGT

TCCAAGTGCCTACATCTGGGAAATCAATACTGAAGAAGAAGGAACTCCTG

AACAAATCAAGACCTTGGTTGAAAAACTTCGCCAAACAAAAGTTCCATCA

CTCTTTGTAGAATCAAGTGTGGATGACCGTCCAATGAAAACTGTTTCTCA

AGACACAAACATCCCAATCTACGCACAAATCTTTACTGACTCTATCGCAG

AACAAGGTAAAGAAGGCGACAGCTACAGCATGATGAAATACAACCTT

GACAAGATTGCTGAAGGATTGGCAAAATAA

PsaA Amino acid sequence
(SEQ ID NO: 55)
MKKLGTLLVLFLSAIILVACASGKKDTTSGQKLKVVATNSIIADITKNIA

GDKIDLHSIVPIGQDPHEYEPLPEDVKKTSEADLIFYNGINLETGGNAWF

TKLVENAKKTENKDYFAVSDGVDVIYLEGQNEKGKEDPHAWLNLENGIIF

AKNIAKQLSAKDPNNKEFYEKNLKEYTDKLDKLDKESKDKFNKIPAEKKL

-continued

IVTSEGAFKYFSKAYGVPSAYIWEINTEEEGTPEQIKTLVEKLRQTKVPS

LFVESSVDDRPMKTVSQDTNIPIYAQIFTDSIAEQGKEGDSYYSMMKYNL

DKIAEGLAK

Recombinant His tagged PsaA
(SEQ ID NO: 56)
MAHHHHHHTNSIIADITKNIAGDKIDLHSIVPIGQDPHEYEPLPEDVKKT

SEADLIFYNGINLETGGNAWFTKLVENAKKTENKDYFAVSDGVDVIYLEG

QNEKGKEDPHAWLNLENGIIFAKNIAKQLSAKDPNNKEFYEKNLKEYTDK

LDKLDKESKDKFNKIPAEKKLIVTSEGAFKYFSKAYGVPSAYIWEINTEE

EGTPEQIKTLVEKLRQTKVPSLFVESSVDDRPMKTVSQDTNIPIYAQIFT

DSIAEQGKEGDSYYSMMKYNLDKIAEGLAK

ELISA test for antibodies

IgG antibodies to Eno, Iga, PpmA and SlrA in serum of humans suffering from pneumococcus infection were measured by EIA. Microtiter plates (Maxisorp; Nunc, Roskilde, Denmark) were coated with 100 μl/well, with a coating concentration of 5 μg/ml of antigen in PBS and incubated overnight at 37° C. The plates were blocked with 1% bovine serum albumin (BSA) and 0.05% Tween 20 in PBS at 37° C. for 1 h. The samples were serially diluted (starting at 1:100) in the dilution buffer (1% BSA, 0.05% Tween 20 in PBS). Duplicates (100 μl/well) were incubated at 370° C. for 2 h. Polyclonal alkaline phosphatase-conjugated antisera to human IgG (Sigma Chemicals, St. Louis) was diluted 1:3000 in the dilution buffer, pipetted at 100 μl/well, and incubated for 2 h at 37° C. Finally, 100 μl/well of MUP (methylumbelliferyl phosphate) (Sigma, CAT#M8883) substrate solution (0.2 mM 4-methylumbelliferyl phosphate, 0.05 M NaCO3, 0.05 mM MgC12) was added, and the plates were incubated for 1 h at 37° C. The fluorescence was measured with an excitation wavelength of 365 nm, and an emission wavelength of 450 nm with a Molecular Devices SpectraMAX (Sunnyvale, USA) microplate reader. The serum endpoint antibody titer was interpolated from the intersection of the absorbance-versus-serum dilution curve at the background fluorescence plus four times the standard deviation. The end-point titer was then converted into antibody concentration (EIA units of immunoglobulin per milliliter) by comparison with a standard serum consisting of pooled healthy adult volunteers, and was considered to contain 100 U/mL of anti-a-enolase, Iga, PpmA or SlrA. Samples with antibody concentrations below the detection limit (30 U/mL for Eno, 4 U/mL for Iga, 4 U/mL for SlrA, and 5 U/mL for PpmA) were assigned the values equivalent to half the detection limit. The results are shown in Table 9.

Statistical methods: We used SPSS software (SPSS, USA) for analysis of log-transformed data. The antibody concentrations in the groups of children are reported as geometric mean concentrations . (GMC, units/ml) with 95% confidence intervals (95% CI) and compared by one way ANOVA (analysis of variable) followed by a LSD (least significant difference) post hoc test. Statistical comparisons between antibody levels in acute and convalescent phase sera were carried out using a paired Student's t test. Fisher's exact test was used when the proportions of variables were compared. A logistic regression was used to evaluate the effects of the acute phase antibody concentration, age and the nature of pneumococcal contact on the antibody response and to evaluate antibody concentrations (logarithm base e of antibody concentration) as a risk factor for the involvement of pneumococci as a risk factor for the development of AOM (acute otitis media). Children were grouped into eight 3-month groups according to the age at which the acute serum was sampled. To determine whether there were any significant differences in relation to age, groups were analyzed by 1-way ANOVA followed by a Tukey's HSD (honestly significance difference) test.

TABLE 9

Results of ELISA test

| | t = 0 (pre-immune serum) | | t = final (post-immune serum) | |
|---|---|---|---|---|
| | average | SD | average | SD |
| PpmA | | | | |
| PpmA | 0.11 | 0.41 | 5147.51 | 4576.27 |
| PpmA + Ply | 0 | 0 | 2796.24 | 1615.74 |
| PpmA + PsaA | 0.08 | 0.31 | 3700.60 | 2553.09 |
| PpmA + Enolase | 0.39 | 0.59 | 2388.10 | 1397.90 |
| PpmA + SlrA | 0.42 | 0.59 | 3407.62 | 2696.83 |
| PpmA + TetTox. | 0.57 | 0.52 | 881.93 | 813.19 |
| PpmA + IgA1 | 0.38 | 1.22 | 6902.50 | 5195.41 |
| PpmA + PsaA + IgA1 | 0.90 | 1.24 | 2008.46 | 1285.48 |
| SlrA | | | | |
| SlrA | 0 | 0 | 3897.68 | 4180.47 |
| SlrA + PpmA | 0 | 0 | 2026.06 | 1083.99 |
| IgA1 | | | | |
| IgA1 | 0.13 | 0.80 | 16365.08 | 18891.05 |
| IgA1 + PpmA | 0.17 | 0.55 | 16291.67 | 10028.60 |
| IgA1 + PsaA | 0 | 0 | 19452.50 | 13428.11 |
| IgA1 + PpmA + PsaA | 0 | 0 | 14177.78 | 7133.86 |
| PsaA | | | | |
| PsaA | 2.63 | 4.47 | 20456.25 | 21898.98 |
| PsaA + PpmA | 0.81 | 1.82 | 51793.75 | 45759.81 |
| PsaA + IgA1 | 0 | 0 | 42600.00 | 52685.55 |
| PsaA + PpmA + IgA1 | 1.71 | 2.22 | 25805.56 | 25713.50 |

EXAMPLE 2

Mucosal Vaccinations

Lactococcus lactis ghosts in combination with the AcmA cell-wall-binding domain (protein anchor) can be used as a carrier/adjuvant system for mucosal and systemic delivery of antigens (WO 99/25836 and WO 02/101026).

In the present study immunogenicity and protective activity of a tri-valent ghost-protein vaccine (SlrA, Iga1prt, PpmA) was tested as well as that of each of the monovalent ghost-protein vaccines after nasal administration of the vaccines and nasal challenge with virulent S. pneumoniae. The aim of the experiments was:

To evaluate protective activity of an intranasal administered L. lactis ghost-protein anchor tri-valent (SlrA, PpmA, Iga1prt) vaccine and of ghost-protein anchor mono-valent (SlrA), ghost-protein anchor mono-valent (PpmA) and ghost-protein anchor mono-valent (Iga1prt) vaccines.

To evaluate the immune response to intranasal administered antigens bound to ghost lactococci and compare the immune response to the antigens administered simultaneously or individually.

To evaluate correlation of bacterial load in lungs, blood and nasopharynx with protection and immune response after vaccination.

Materials and Methods

Construction of vectors. Table 10 summarises the characteristics of the antigens used in the ghost protein-based S. pneumoniae vaccines.

PpmA::PA fusion. Plasmid pPA32, specifying a fusion between the *S. pneumoniae* PpmA protein and the protein anchor (FIG. 12), was constructed by ligating an NcoI- and EcoRI-cleaved PCR-amplified fragment of CbpA into the NcoI and EcoRI sites of pPA3 (Steen et al. 2003. J. Biol. Chem. 278:23874-23881). The PpmA-specific fragment was amplified with the primers PpmA.1 (cggtctcacatgtcgaaagggt-cagaaggtgcagacc) and PpmA.2 (cggtctcgaattgcttcgtttgatgtac-tactgcttgag) with *S. pneumoniae* strain D39 chromosomal DNA as template. The ligation mix was cut with EcoRI and NheI before it was used for electroporation of *L. lactis* PA1001 (Kuipers et al. J. Biol. Chem. 2004 Mar. 24 [Epub ahead of print]). The final construct was designated pPA32.

Iga1prt::PA fusion. Plasmid pPA152, specifying a fusion between a fragment of the *S. pneumoniae* Iga1prt protein (residues 672 to 1330) and the protein anchor (FIG. 13). Plasmid pPA152 was constructed by ligating an NcoI- and EcoRI-cleaved PCR-amplified fragment of Iga1prt into the corresponding sites of pPA3. The Iga1prt-specific fragment was amplified with the primers Iga1.fw2 (cgtctcccatggga-caaacagaaccagagccatcaaacgg) and Iga1trunc2.rev (ccgtctc-gaattctagccagtccagcatc) with *S. pneumoniae* strain TIGR4 chromosomal DNA as template. The ligation mix was cut with NheI before it was used for electroporation of *L. lactis* PA1001. The final construct was designated pPA152.

SlrA::PA fusion. Plasmid pPA162, specifying a fusion between the *S. pneumoniae* SlrA protein and the protein anchor (FIG. 14), was constructed by ligating an Esp3I-cleaved PCR-amplified fragment of SlrA into the NcoI and EcoRI sites of plasmid pPA3. The SlrA-specific fragment was amplified with the primers SlrA.fw (ccgtctcccatggtccaacg-cagtctgcgt) and SlrA.rev (ccgtctcgaattccagatttaaaatcg-tagtctttcacca) with *S. pneumoniae* strain D39 chromosomal DNA as template. The ligation mix was cut with SphI before it was used for electroporation of *L. lactis* PA1001. The final construct was designated pPA162.

Production of Ghost cells. *L. lactis* Ghosts were produced as described in WO 02/101026. Each dosis representing the amount used for one nasal administration in mice, contained approximately $2.5 \times 10^9$ Ghosts.

Production of antigen. The yeast-based GLS medium was used for production of the vaccine. GLS contains 2% gistex (Gistex® LS Ferm Powder AGGL -1027180, Strik Special Additives, The Netherlands), 3% β-glycerophosphate and 2% glucose. Glucose was sterilized as a separate solution and added to the broth when the strain was inoculated. *L. lactis* PA1001 containing plasmids pPA152, pPA32 or pPA162 were grown in GLS supplemented with 5 µg/ml chloramphenicol. At OD600 levels of approximately 0.5 and 1.0 the cultures were induced by adding 1 ml of the cell-free supernatant of a nisin producing *L. lactis* culture per liter of medium (1:1000; Kuipers et al. 1997. Tibtech. 15: 135-140). The culture was left at 30° C. overnight, after which the culture supernatants were concentrated with a VivaFlow tangential flow module (Vivascience VivaFlow 200; 10,000 Da cut-off). The concentrate was sterilised through a 0.45 µm filter and stored at +4° C. until binding.

Production of the vaccines. The vaccines were produced as follows:

Ghost-SlrA::PA monovalent vaccine:
27.5 ml of a 10× concentrated supernatant of a SlrA::PA producing *L. lactis* culture was bound to 4.6 ml Ghost (46 units) on a blood suspension mixer for 30 minutes at room temperature. After washing, the pellet was resuspended in 920 µPBS and 880 µl was divided in 4 vials (220 µl each). 3 vials for the monovalent vaccine and 1 vial for the trivalent vaccine.

Ghost-PpmA::PA Monovalent Vaccine:
170 ml of a 10× concentrated supernatant of a PpmA::PA producing *L. lactis* culture was bound to 4.6 ml Ghost (46 units) on a blood suspension mixer for 30 minutes at room temperature. After washing, the pellet was resuspended in 920 µl PBS and 880 µl was divided in 4 vials (220 µl each). 3 vials for the monovalent vaccine and 1 vial for the trivalent vaccine.

Ghost-Iga1prt::PA Monovalent Vaccine:
All concentrated supernatant (25-41×) of a Iga1prt::PA producing *L. lactis* culture was bound to 4.6 ml Ghost (46 units) on a blood suspension mixer for 30 minutes at room temperature. After washing, the pellet was resuspended in 920 µl PBS and 880 µl was divided in 4 vials (220 µl each). 3 vials for the monovalent vaccine and 1 vial for the trivalent vaccine.

Trivalent Vaccine:
Three vials of monovalent vaccines were mixed and divided over 3 vials (220 µl each).

All vaccines were kept at −80° C. until the start of the immunizations. One dosis (20 µl) of a nasal vaccine contains $2.5 \times 10^9$ Ghost cells.

Mice. Female outbred CD-1 mice were purchased from Harlan France. Mice were 6 week-old at the time of starting the study.

Pneumococcal challenge strain. *S. pneumoniae* D39, serotype 2, was obtained from the National Collection of Type Cultures (NCTC 7466; Central Public Health Laboratory, London).

Immunization and treatment groups. Mice were immunized intranasally under light inhalation anaesthesia (isoflurane/$O_2$/$N_2O$) by pipeting 20 µl of the vaccine or control onto the nostrils. Complete immunization consisted of 3 doses given at 10 day-intervals.

Mice (10 per group) received PBS as control. The vaccines consisted of $2.5 \times 10^9$ ghosts and contained 5 µg Iga1prt, 10 □g PpmA and 50 µg SlrA per dose for the mono-valent vaccines, $2.5 \times 10^9$ ghosts with a third of the monovalent doses of each antigen for the tri-valent vaccine.

The following groups were used:
1. 20 µl PBS.
2. $2.5 \times 10^9$ lactococcal ghosts-protein anchor-SlrA fusion (50 µg SlrA::PA) in 20 µl PBS.
3. $2.5 \times 10^9$ lactococcal ghosts-protein anchor-PpmA fusion (10 µg PpmA::PA) in 20 µl PBS.
4. $2.5 \times 10^9$ lactococcal ghosts-protein anchor-IgAprt fusion (IgAprt::PA) in 20 µl PBS.
5. $2.5 \times 10^9$ lactococcal ghosts with bound protein anchor-SlrA/PpmA/Iga1prt fusions (antigens individually bound as in groups 2, 3 and 4 and mixed in ratio 1:1:1) in 20 µl PBS.

Challenge. Intranasal challenge was performed 4 weeks after the last immunization. Aliquots of inoculum were rapidly thawed and bacteria diluted in sterile PBS to $1\times10^6$ CFU/50 µl. Challenge was carried out under light anesthesia by pipeting 50 µl of the inoculum onto the nostrils of the mice. After inoculation were laid on their backs until recovery. Mice were weighted before challenge and at t=44-h. Condition of the mice was monitored frequently (at least three times a day) and scored for the following criteria: hunched, starry coat, lethargic, moribund. After 44-h mice blood was collected under anesthesia and mice terminated by cervical dislocation. Nose washes and lungs were collected for quantitative microbiological culture.

Scoring of health status. Each animal was scored 44 h after infection according to the criteria given in Table 11. The maximum score per group of 10 animals is 40 (all animals dead). All animals healthy results in a score of 0. The disease index is the percentage of the maximum score.

Determination of bacterial load. Blood samples, lungs homogenates and nose washes were serially diluted and plated on agar with 5% sheep blood. Plates were incubated overnight at 37° C. before counting the colonies. Statistical analyses were performed using GraphPad Instat. Difference between groups were assessed by unpaired student t-test with log values of bacterial. Loss of weight was assessed by paired t-test. Comparison of disease index was performed by Mann-Whitney analyse. A P-value <0.05 is considered significant.

ELISA. Antigens (SlrA, PpmA and Iga1protease), purified by making use of his-tag purification, were coated in 96 well plates (2 µg/ml) in coating buffer (50mM sodium carbonate, pH9.6). Only Igalprotease was coated at 10 µg/ml in coating buffer. For the calibration curve rat anti-mouse kappa chain (BD Biosciences 559749, 0.5 mg/ml) was coated at 1/500 dilution in coating buffer. After incubation overnight at 4° C., the plates were rinsed 3 times with wash buffer (0.02% Tween 20 in PBS). The plates were blocked by adding 100 µl blocking buffer (1% BSA, 0.02% Tween 20 in PBS) in each well. The plates were incubated for 1 hour at room temperature. All blood samples were diluted 1/100 with blocking buffer, and serial dilutions (1/3) of these samples were performed in 100 µl blocking buffer. For the calibration curve a serial dilution of mouse IgG1 kappa light chain (Sigma M7894) was made, starting with 1 µg/ml. All samples were tested in duplo. After incubation for 2 hours at room temperature, the plates were rinsed 3 times with wash buffer. Antigen specific antibodies were detected by using goat anti-mouse IgG (Fc)-alkaline phosphatase conjugate (Sigma A7434) diluted 1/5000 in blocking buffer. The plates were rinsed two times with washing buffer and two times with double distilled H2O and were developed with PNPP (Sigma N2765, 1 mg/ml in 50 mM sodium carbonate, 1 mM MgCl2, pH9.6). After 30 minutes of incubation with pNPP, the reaction was stopped by addition of 50 µl NaOH (2M). The absorbance at 405 nm was recorded and the IgG concentration in the blood samples was determined by comparison with the calibration curve.

Results

Composition of the vaccine. The amounts of antigen-PA fusions in the different vaccines were determined using CBB-stained SDS-PAGE gels (example in FIG. 15), containing samples from different Ghost-antigen groups and a BSA protein standard. The established amounts were for the monovalent vaccines:

| Ghost-SlrA::PA: | 50 µg/dose |
| Ghost-PpmA::PA | 10 µg/dose |
| Ghost-Iga1prt::PA | 5 µg/dose |

The trivalent vaccine was composed by mixing the monovalent vaccines in a ratio of 1:1:1 with the total number of ghost the same as in the monovalent vaccines (2.5×109) resulting in the following amounts of antigen:

| Ghost-SlrA::PA: | 17 µg/dose |
| Ghost-PpmA::PA | 3.3 µg/dose |
| Ghost-Iga1prt::PA | 1.7 µg/dose |

The vaccines were formulated in PBS without additional adjuvant.

Vaccine Efficacy.

Health status. Intranasal vaccination with the tri-valent ghost vaccine resulted in protection against a nasal challenge with virulent *S. pneumoniae*. The vaccinated mice remained healthy as reflected by a disease index significantly lower when compared to the mice that received PBS (FIG. 16). No significant loss of weight was seen in this group (FIG. 17), indicating a significant improvement in health. Of the monovalent vaccines, SlrA and PpmA did show minor protective effects (FIG. 16). The PpmA monovalent vaccine group also showing no significant loss of weight (FIG. 17), indicating a better overall health then in the PBS control group. However, overall the animals in the trivalent vaccine group clearly showed the best health status after challenge.

Bacterial counts (see FIG. 18 and Table 12). In mice vaccinated with the tri-valent vaccine the number of bacteria in the lungs and nose was significantly reduced compared to the PBS control group (P-values<0.05). This was not the case when the mice were immunized with each one of the monovalent vaccines. Also, comparison between the tri-valent vaccine group and the monovalent vaccine groups shows significant differences in the bacterial counts in nose, lung and blood. Again, clearly the tri-valent vaccine group performed best, Immune response. Serum IgG response were determined by ELISA after 3 immunizations in pre-challenge blood. FIG. 19 shows the serum IgG antigen specific responses generated in the different vaccine groups. The responses against SlrA, PpmA and Iga1prt in the monovalent vaccines are similar to the responses to these antigens in the tri-valent vaccines, indicating that the amounts of antigen in the tri-valent vaccine are sufficient to elicit serum antibody responses of this magnitude for these antigens. The combined response to the three antigens in the tri-valent vaccine is needed to obtain the protective effect, since each of the individual responses in the monovalent vaccine groups did not provide sufficient protection.

CONCLUSIONS

Nasal (mucosal) vaccination with the tri-valent SlrA, PpmA, Iga1prt vaccine provided increased protection of the mice after challenge with *S. pneumoniae*.

Nasal vaccination with the tri-valent vaccine resulted in significant reduction in the number of bacteria in lungs and nose.

Nasal immunization with the mono- and trivalent vaccines resulted in significant antigen specific IgG levels in the blood serum.

Nasal vaccination with the mono-valent vaccines had no protective effect upon challenge with *S. pneumoniae*.

TABLE 10

Overview of *S. pneumoniae* antigen characteristics. The segments that were used for the actual protein anchor fusions are indicated.

| Antigen | Genbank/SwissProt | Protein function | Size of original protein (aa) | Signal sequence | Present in PA fusion aa & percentage |
|---|---|---|---|---|---|
| SlrA | NP_345269 | Peptidyl-prolyl isomerase (chaperone) | 267 | 1-17 (lipo) | 21-267 (92%) |
| PpmA | NP_345462 | Peptidyl-prolyl isomerase (chaperone) | 313 | 1-22 (lipo) | 23-311 (92%) |
| Iga1prt | NP_345623 | Iga1 protease | 2004 | 1-36 or 42 | 672-1330 (33%) |

TABLE 11

Scoring overview of health status.

| Score | Interpretation | Parameters |
|---|---|---|
| 0 | Healthy | / |
| 1 | A bit ill | Starry coat and/of hunched + |
| 2 | Ill | Starry coat and/of hunched ++ |
|   |   | Lethargic + |
| 3 | Very ill | Starry coat and/of hunched +++ |
|   |   | Lethargic ++ |
| 4 | Dead | / |

TABLE 12

Statistical comparisons between various vaccines.
P values < 0.05 are considered significant (indicated in bold).

|  | Lungs | Nose | Blood |
|---|---|---|---|
| Ghost-SlrA::PA with PBS | 0.7185 | 0.2022 | 0.9156 |
| Ghost-PpmA::PA with PBS | 0.7096 | 0.9758 | 0.8406 |
| Ghost-Iga1::PA with PBS | 0.3527 | 0.7923 | 0.26 |
| Tri-valent Ghosts with PBS | 0.0498 | <0.0001 | 0.167 |
| Tri-valent Ghosts with Ghost-SlrA::PA | 0.0378 | 0.0465 | 0.2005 |
| Tri-valent Ghosts with Ghost-PpmA::PA | 0.1853 | 0.0026 | 0.3289 |
| Tri-valent Ghosts with Ghost-Iga1::PA | 0.0142 | 0.0023 | 0.021 |

REFERENCES

Obaro S K. The new pneumococcal vaccine. Clin Microbiol Infect 2002; 8(10): 623-33.

Darkes M J, Plosker G L. Pneumococcal conjugate vaccine (Prevnar; PNCRM7): a review of its use in the prevention of *Streptococcus pneumoniae* infection. Paediatr Drugs 2002; 4(9):609-30.

Wuorimaa T, Kayhty H. Current state of pneumococcal vaccines. Scand J Immunol 2002; 56(2):111-29.

Lee L H, Lee C J, Frasch C E. Development and evaluation of pneumococcal conjugate vaccines: clinical trials and control tests. Crit Rev Microbiol 2002; 28(1):27-41.

Klugman K P. Efficacy of pneumococcal conjugate vaccines and their effect on carriage and antimicrobial resistance. Lancet Infect Dis 2001; 1(2):85-91.

Rapola S, Jantti V, Haikala R, Syrjanen R, Carlone G M, Sampson J S, Briles DE, Paton J C, Takala A K, Kilpi T M, Kayhty H. Natural development of antibodies to pneumococcal surface protein A, pneumococcal surface adhesin A, and pneumolysin in relation to pneumococcal carriage and acute otitis media. J Infect Dis 2000; 182(4):1146-52.

Rapola S, Kilpi T, Lahdenkari M, Makela P H, Kayhty H. Antibody response to the pneumococcal proteins pneumococcal surface adhesin A and pneumolysin in children with acute otitis media. Pediatr Infect Dis J 2001; 20(5):482-7.

Zysk G, Bethe G, Nau R, Koch D, Grafin Von Bassewitz V C, Heinz H P, Reinert R R. Immune response to capsular polysaccharide and surface proteins of *Strepococcus pneumoniae* in patients with invasive pneumococcal disease. J Infect Dis 2003 Jan 15;187(2):330-3.

McCool T L, Cate T R, Moy G, Weiser J N. The immune response to pneumococcal proteins during experimental human carriage. J Exp Med 2002; 195(3):359-65.

Overweg K, Pericone C D, Verhoef G G, Weiser J N, Meiring H D, De Jong A P, De Groot R, Hermans P W. Differential protein expression in phenotypic variants of *Streptococcus pneumoniae*. Infect Immun 2000; 68(8):4604-10.

Overweg K, Kerr A, Sluijter M, Jackson M H, Mitchell T J, de Jong A P, de Groot R, Hermans P W. The putative proteinase maturation protein A of *Streptococcus pneumoniae* is a conserved surface protein with potential to elicit protective immune responses. Infect Immun 2000; 68(7):4180-8.

BRIEF DESCRIPTION OF THE DRAWINGS

FIG. 1. Titres of anti-pneumococcal IgG against PpmA in children and adults.

FIG. 2. Titres of anti-pneumococcal IgG against pneumolysin in children and adults.

FIG. 3. Titres of anti-pneumococcal IgG against IgA1 proteinase in children and adults.

FIG. 4. Titres of anti-pneumococcal IgG against alpha-enolase in children and adults.

FIG. 5. Titres of anti-pneumococcal IgG against SirA in children and adults.

FIG. 12. Sequence of the secreted PpmA::PA fusion protein. Underlined are the aminoacids of Iga1prt. Protein anchor (PA) amino acids are in italics.

FIG. 13. Sequence of the secreted Iga1prt::PA fusion protein. Underlined are the aminoacids of Iga1prt. Protein anchor (PA) amino acids are in italics.

FIG. 14. Sequence of the secreted SlrA::PA fusion protein. Underlined are the aminoacids of Iga1prt. Protein anchor (PA) amino acids are in italics.

SEQUENCE LISTING

Figure 6:
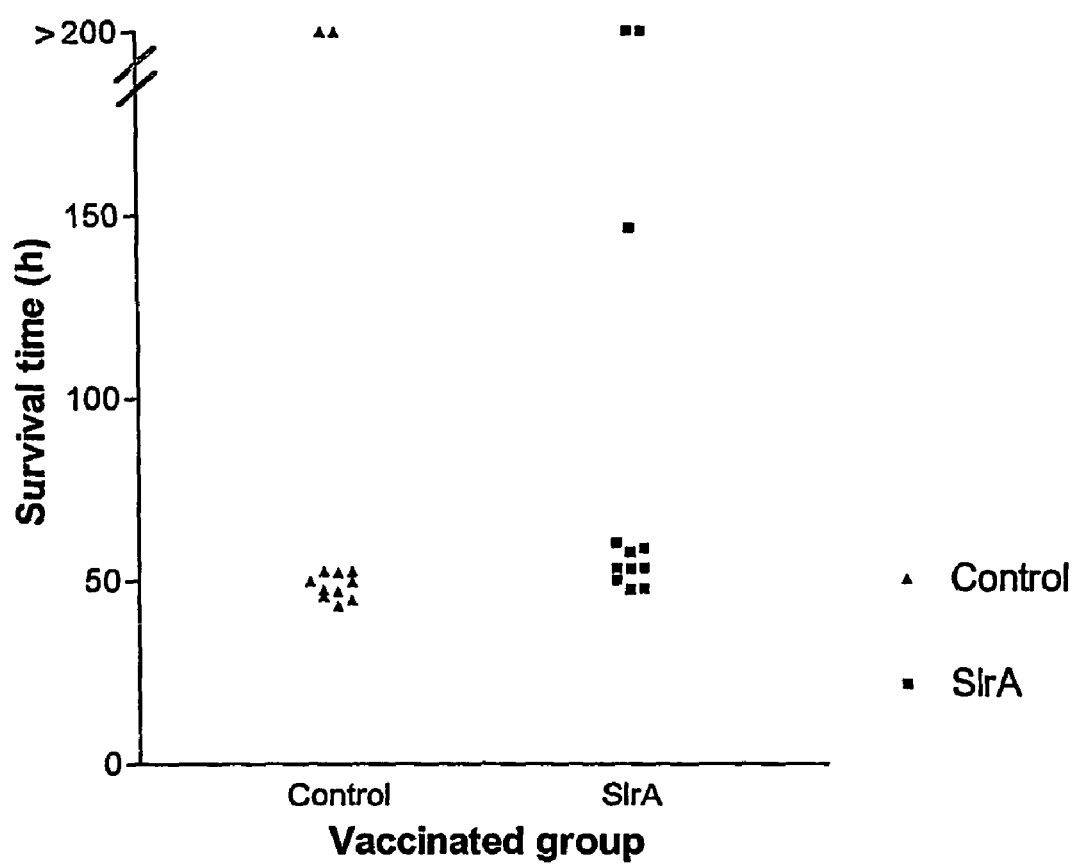
FIG. 6. Survival time of SirA-vaccinated CD-1 mice infected intranasally with *Streptococcus pneumoniae* D39.
Figure 7:
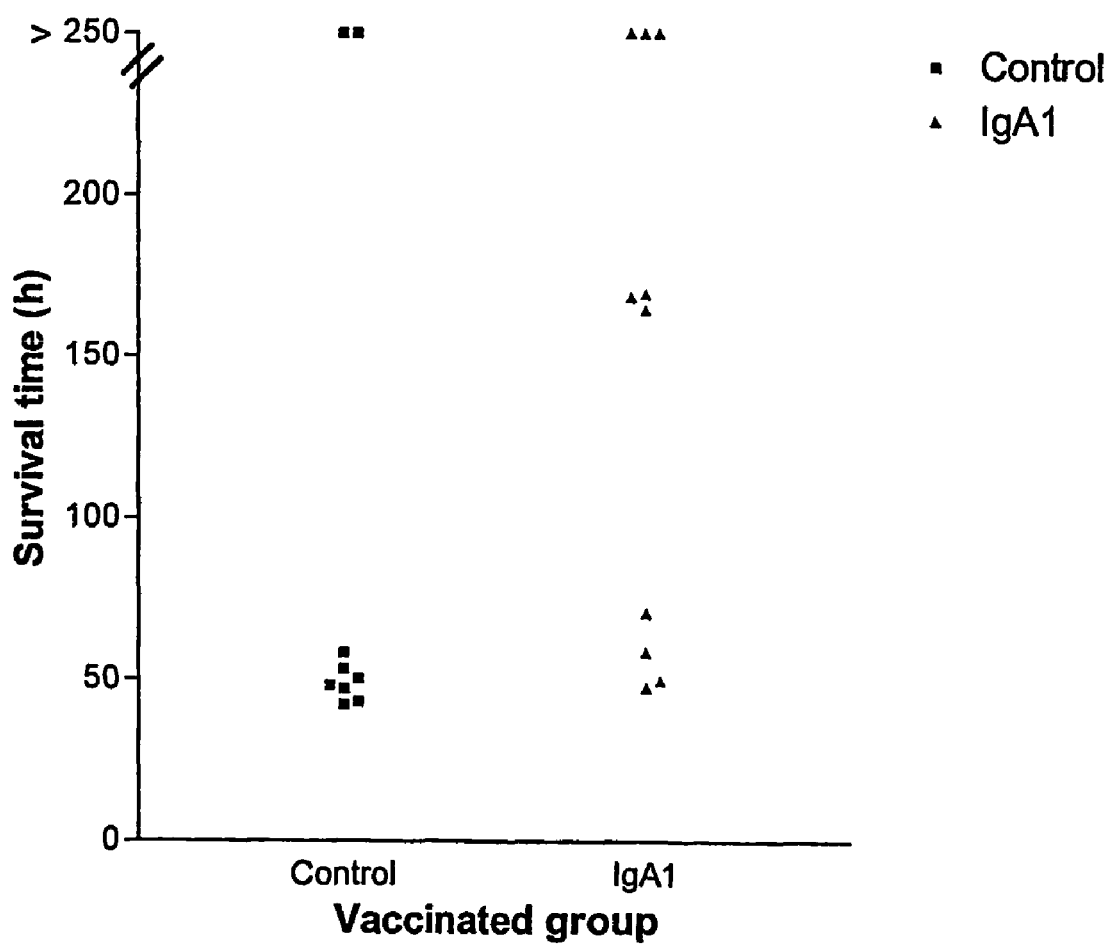
FIG. 7. Survival time of IgA1 proteinase-vaccinated CD-1 mice infected intranasally with *Streptococcus pneumnoniae* D39.
Figure 8:
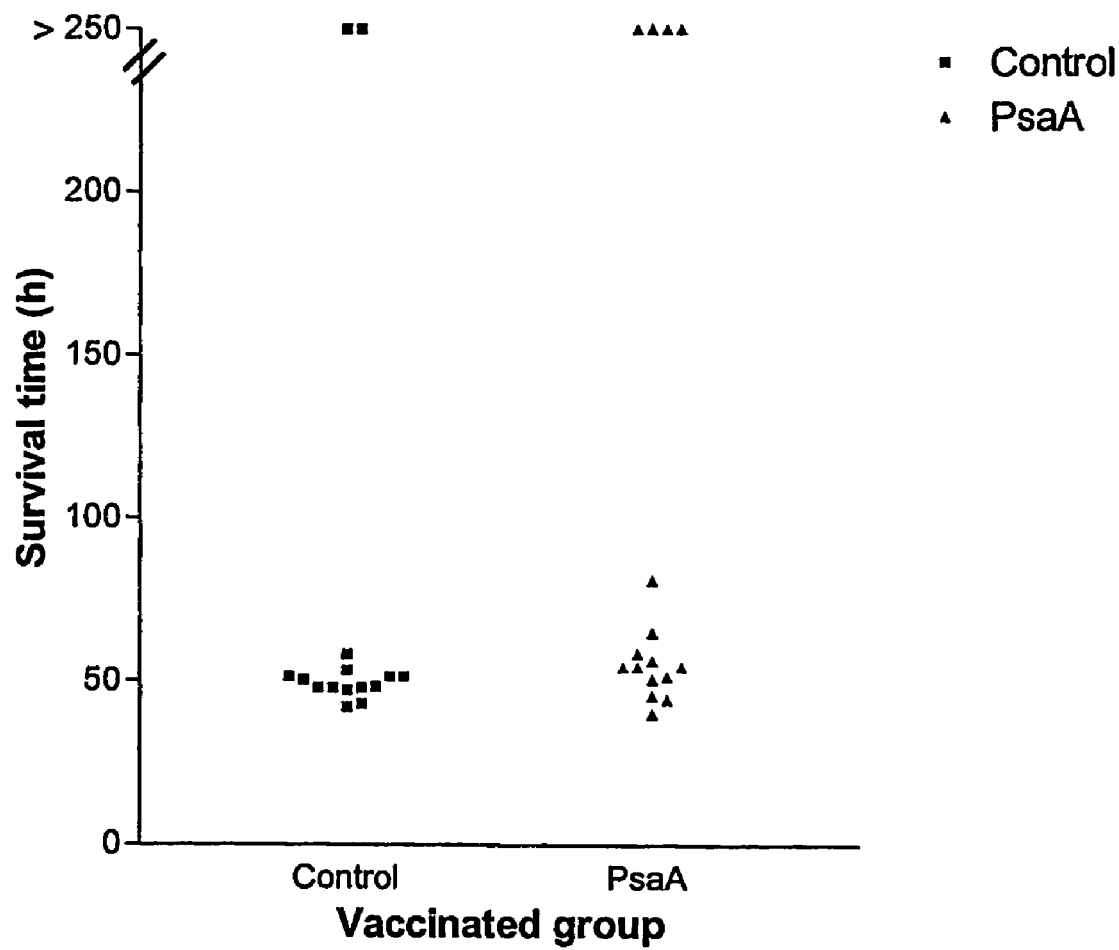
FIG. 8. Survival time of PsaA-vaccinated CD-1 mice infected intranasally with *Streptococcus pneumoniae* D39.
Figure 9:
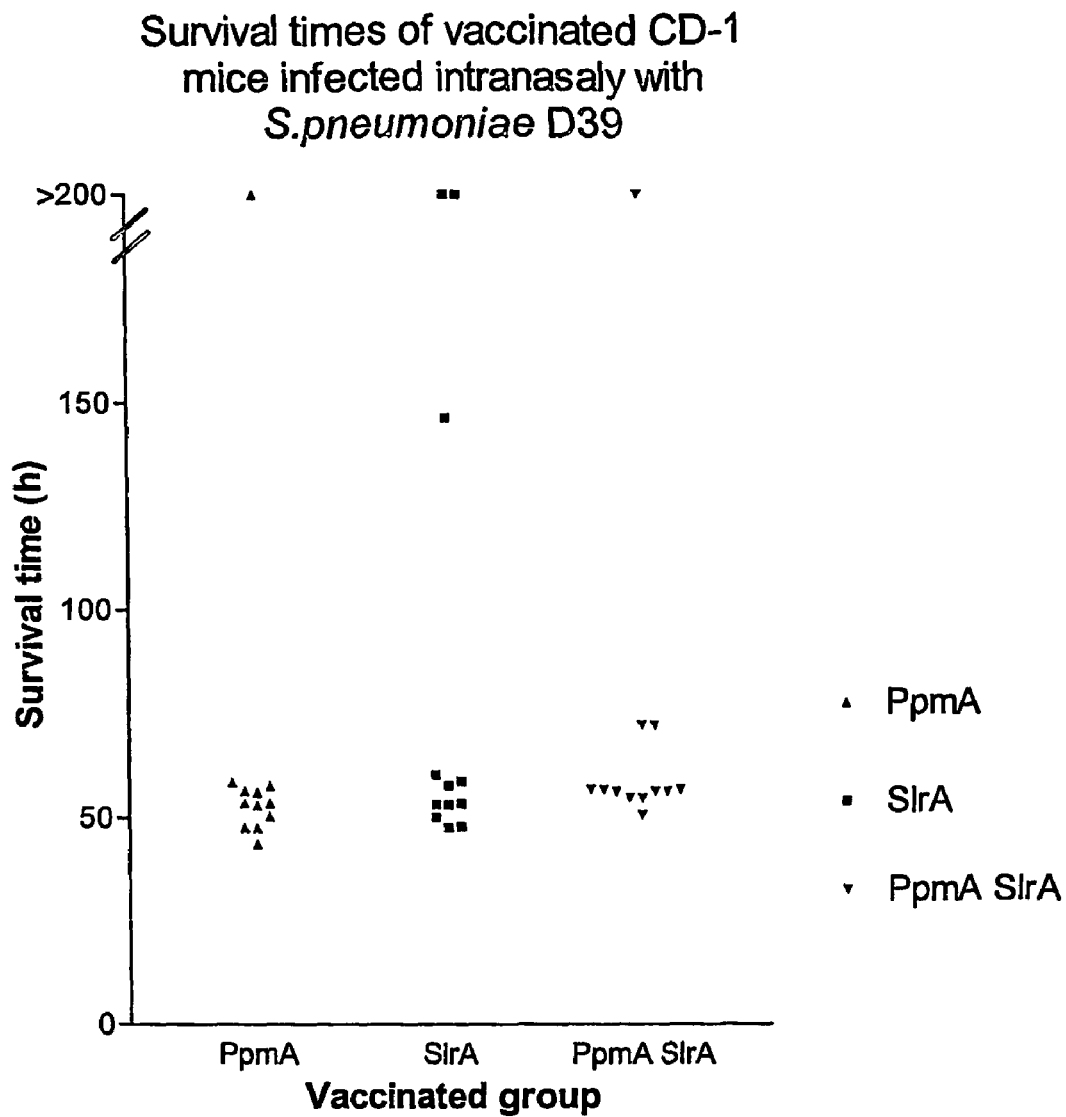
FIG. 9. Survival time of SirA- and PpmA-vaccinated CD-1 mice infected intranasally with *Streptococcus pneumoniae* D39.
Figure 10:
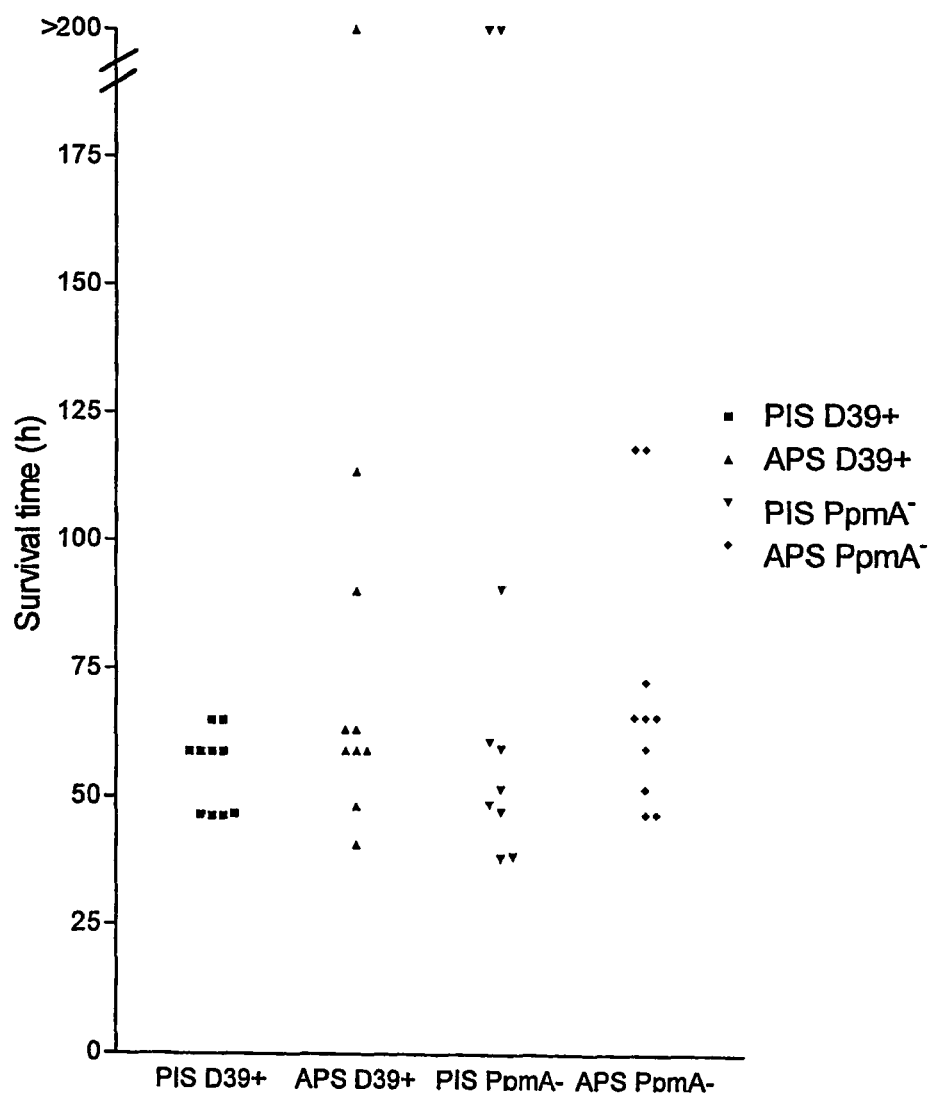
FIG. 10. Passive immunization of CD-1 mice with preimmune serum (PIS), anti-PpmA serum (APS) and challenged intranasally with *Strepococcus pneumoniae* D39 or a PpmA-negative knockout strain of *Strepococcus pneumoniae*.
Figure 11:
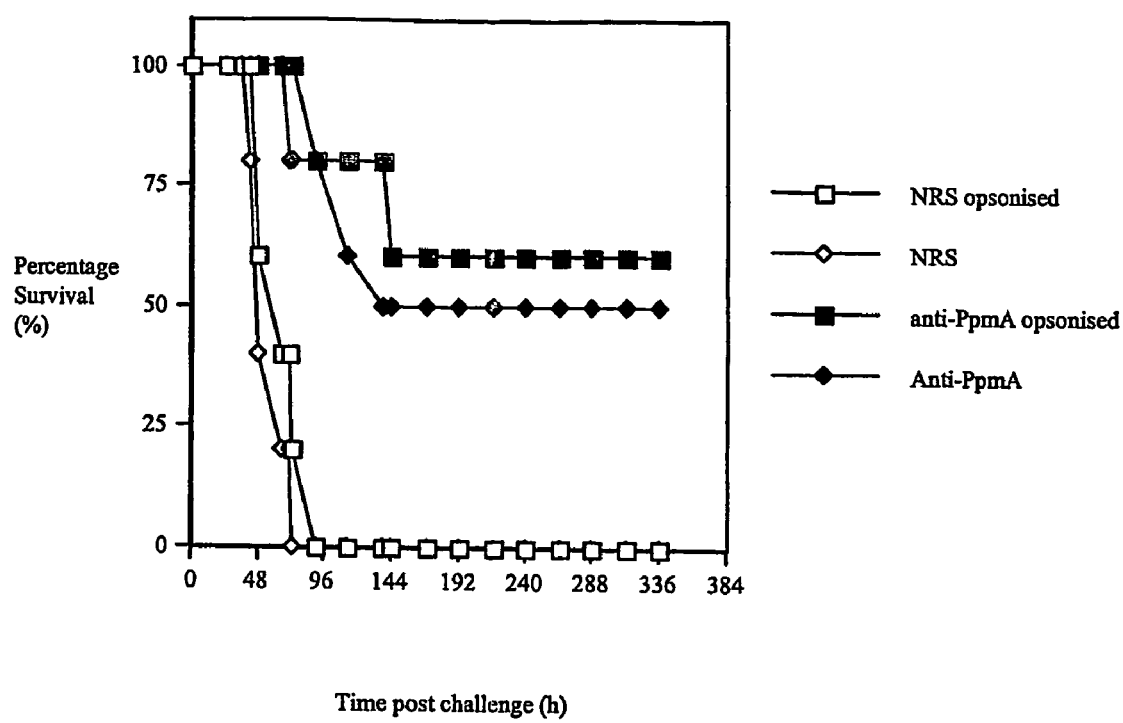
FIG. 11. Survival of MF-1 mice passively vaccinated with anti-PpmA antiserum and intranasally infected with *Strepococcus pneumoniae* D39.
Figure 15:
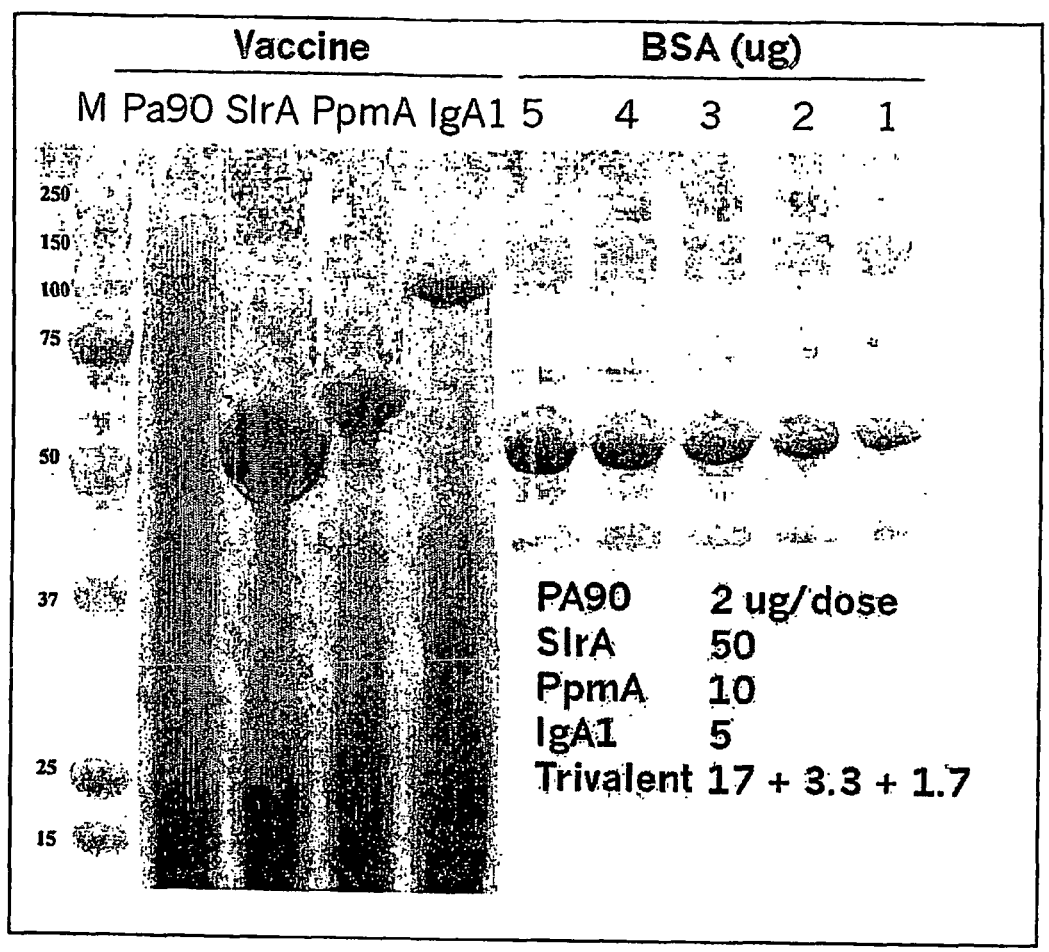
FIG. 15. A CBB (Coomassie Brilliant Blue) stained SDS-PAGE gel with the Ghost-antigen vaccines and a BSA (bovine serum albumin) reference. SlrA, PpmA and Iga1 are samples from the vaccine groups. Each sample represents one dose (20 µl). In the five lanes on the right, the number represents the amount of BSA in micrograms. An estimate of the amount of bound antigen is made and shown in the lower right part of the Figure.
Figure 16:
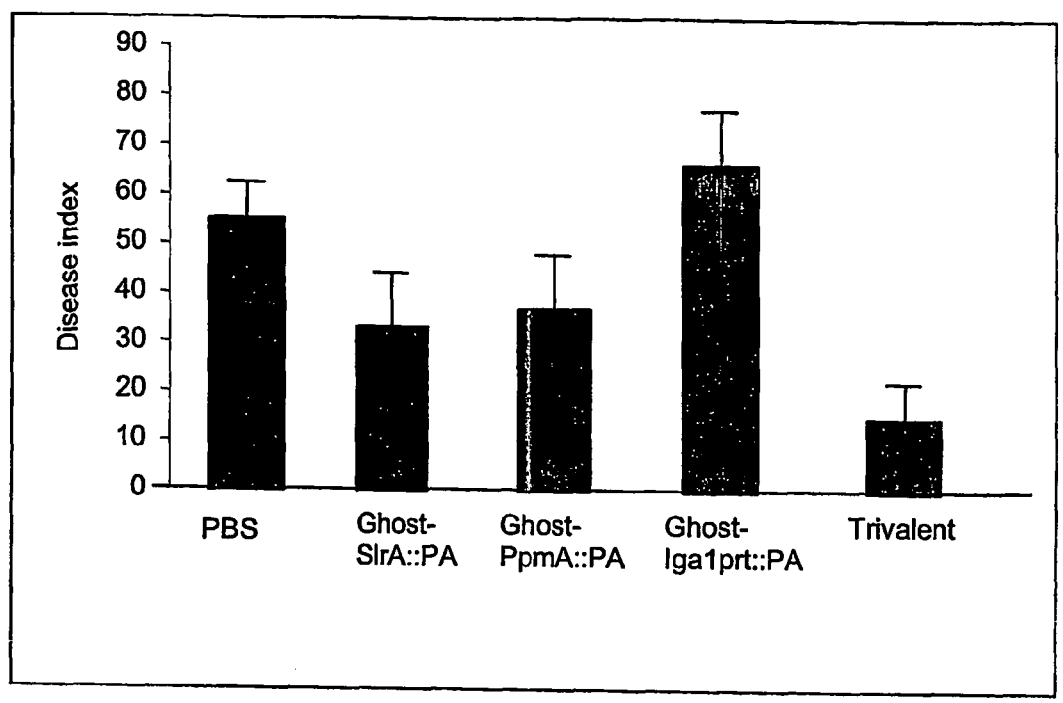
FIG. 16. Health status of the mice at the time of ending experiment (t=44-h after infection). A score ranging from 0-4 was attributed to each mouse according to the parameters described in material and methods. The disease index was calculated as percentage of maximal score and presented as average+SEM for each group. A high score indicates that most animals are diseased. A low score indicates that most animals are healthy.
Figure 17:
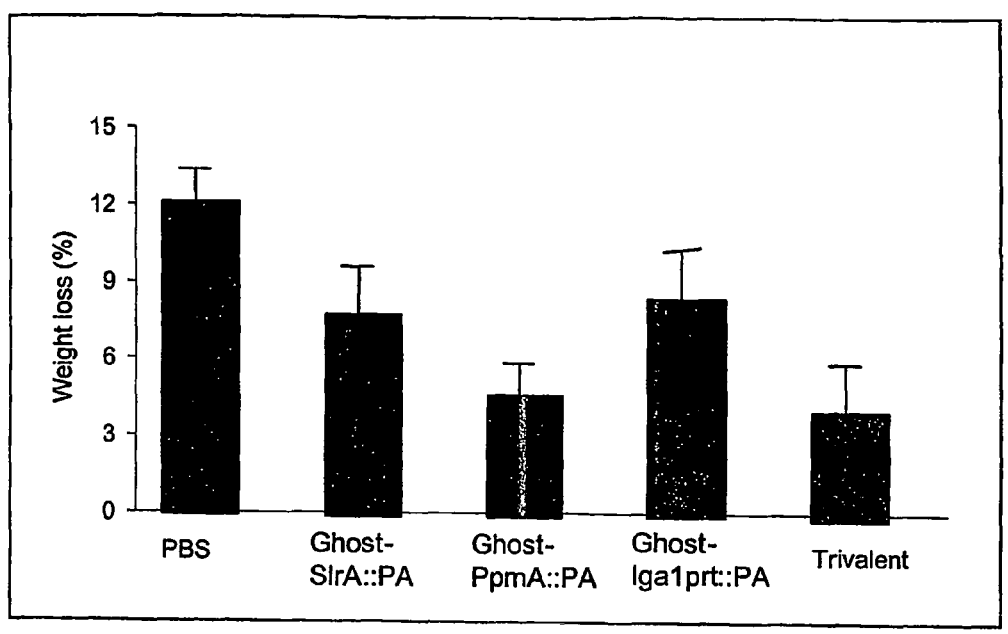
FIG. 17. Weight loss upon challenge. Mice were weighted prior infection and 44-h after challenge. Loss of weight is calculated as percentage of the initial weight and presented as average+SEM for each group. Loss of weight is an indication that animals are diseased.
Figure 18:
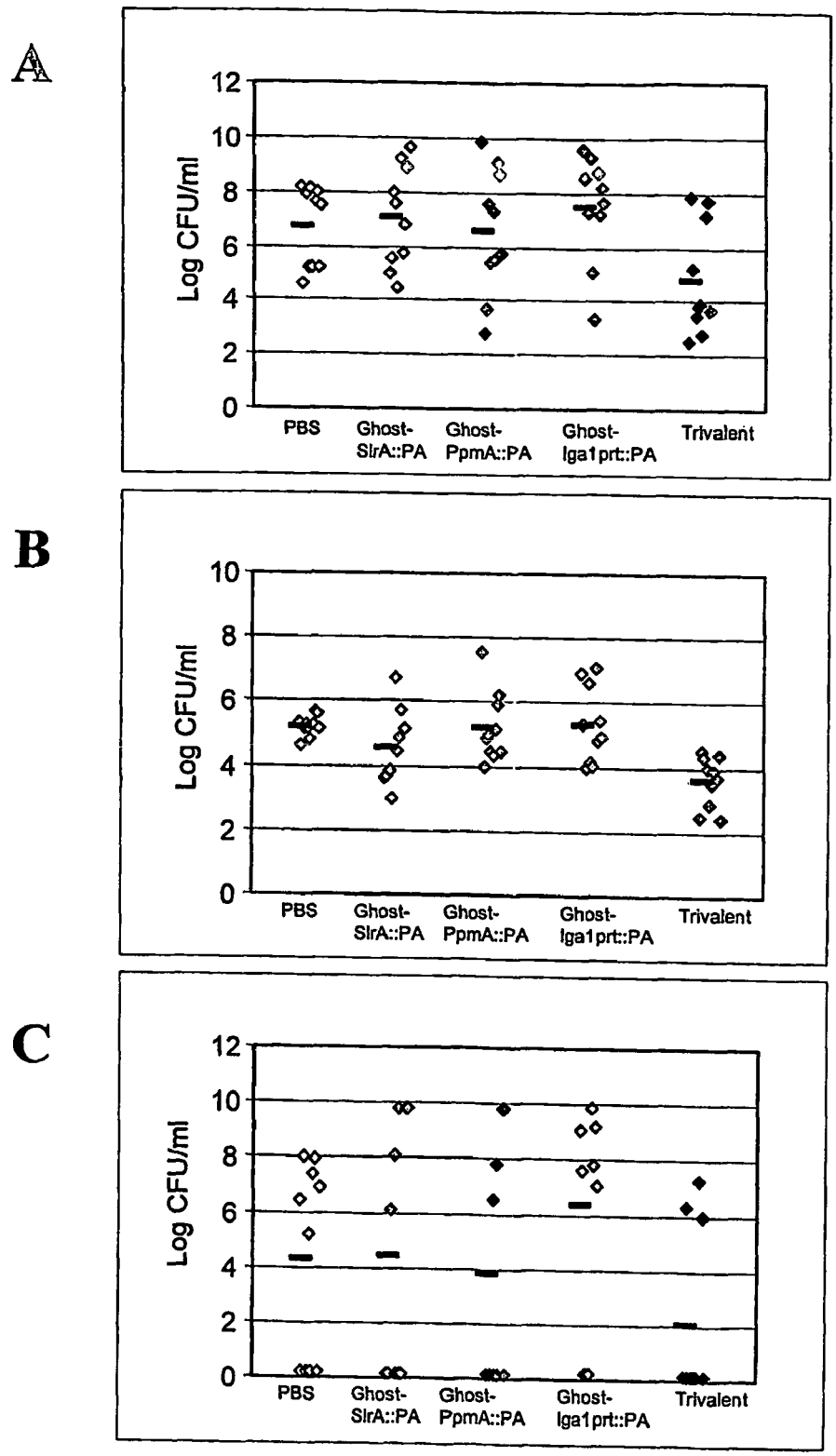
FIG. 18. Bacterial counts 44-h post-challenge in the lungs (A), nose (B) and blood (C). Graphs show individual data (◇) and the average (—) for each group. High bacterial counts are an indication that animals are not protected.
Figure 19:
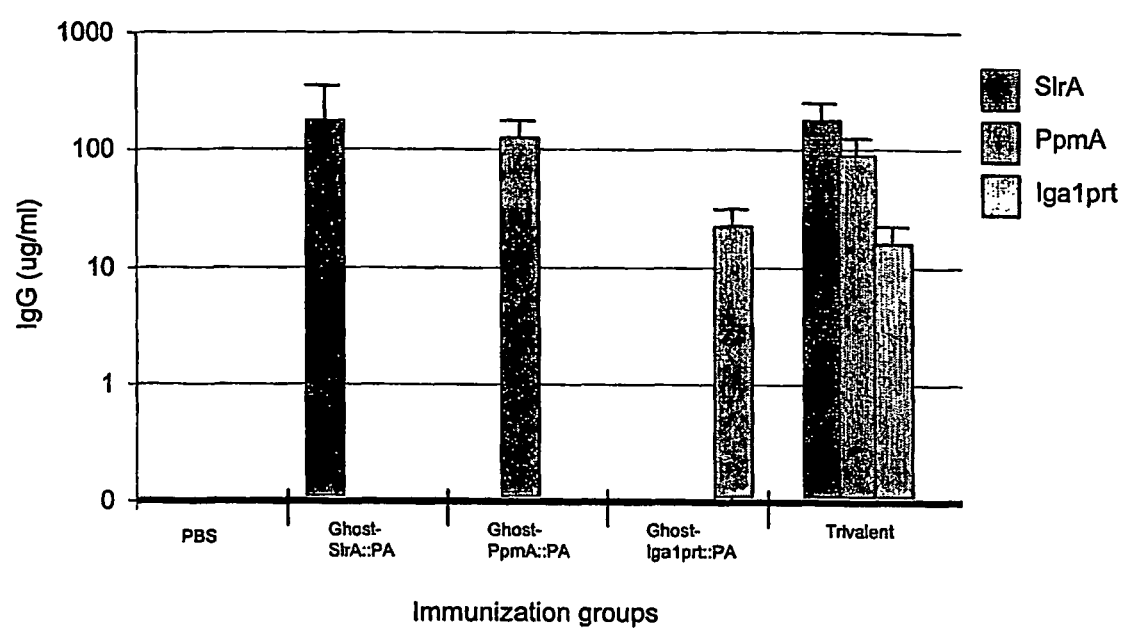
FIG. 19. Antigen specific IgG in the serum after 3 immunizations but prior to challenge. The values are presented as average+SEM for each group.

```
<160> NUMBER OF SEQ ID NOS: 62

<210> SEQ ID NO 1
<211> LENGTH: 12
<212> TYPE: PRT
<213> ORGANISM: Streptococcus pneumoniae
<220> FEATURE:
<221> NAME/KEY: SITE
<222> LOCATION: (1)..(12)
<223> OTHER INFORMATION: PBD motif
<220> FEATURE:
<221> NAME/KEY: MISC_FEATURE
<222> LOCATION: (1)..(1)
<223> OTHER INFORMATION: "X" stands for Y or V
<220> FEATURE:
<221> NAME/KEY: MISC_FEATURE
<222> LOCATION: (2)..(5)
<223> OTHER INFORMATION: "X" can be any amino acid or absent
<220> FEATURE:
<221> NAME/KEY: MISC_FEATURE
<222> LOCATION: (8)..(8)
<223> OTHER INFORMATION: "X" stands for S or T
<220> FEATURE:
<221> NAME/KEY: MISC_FEATURE
<222> LOCATION: (9)..(9)
<223> OTHER INFORMATION: "X" stands for V, L, I or A
<220> FEATURE:
<221> NAME/KEY: MISC_FEATURE
<222> LOCATION: (10)..(11)
<223> OTHER INFORMATION: "X" can be any amino acid or absent
<220> FEATURE:
<221> NAME/KEY: MISC_FEATURE
<222> LOCATION: (12)..(12)
<223> OTHER INFORMATION: "X" stands for V, L, I or A

<400> SEQUENCE: 1

Xaa Xaa Xaa Xaa Xaa Gly Asp Xaa Xaa Xaa Xaa Xaa
1               5                   10

<210> SEQ ID NO 2
<211> LENGTH: 12
<212> TYPE: PRT
<213> ORGANISM: Streptococcus pneumoniae
<220> FEATURE:
<221> NAME/KEY: MISC_FEATURE
<222> LOCATION: (2)..(6)
```

```
<223> OTHER INFORMATION: "X" can be any amino acid or absent
<220> FEATURE:
<221> NAME/KEY: SITE
<222> LOCATION: (1)..(12)
<223> OTHER INFORMATION: CBD motif
<220> FEATURE:
<221> NAME/KEY: MISC_FEATURE
<222> LOCATION: (9)..(9)
<223> OTHER INFORMATION: "X" stands for W, Y or I
<220> FEATURE:
<221> NAME/KEY: MISC_FEATURE
<222> LOCATION: (10)..(10)
<223> OTHER INFORMATION: "X" stands for W, Y or T
<220> FEATURE:
<221> NAME/KEY: MISC_FEATURE
<222> LOCATION: (11)..(11)
<223> OTHER INFORMATION: "X" stands for Y, V or L
<220> FEATURE:
<221> NAME/KEY: MISC_FEATURE
<222> LOCATION: (12)..(12)
<223> OTHER INFORMATION: "X" stands for F or V
<220> FEATURE:
<221> NAME/KEY: MISC_FEATURE
<222> LOCATION: (8)..(8)
<223> OTHER INFORMATION: "X" can be any amino acid

<400> SEQUENCE: 2

Gly Xaa Xaa Xaa Xaa Xaa Gly Xaa Xaa Xaa Xaa Xaa
1               5                   10

<210> SEQ ID NO 3
<211> LENGTH: 35
<212> TYPE: PRT
<213> ORGANISM: Streptococcus pneumoniae
<220> FEATURE:
<221> NAME/KEY: SITE
<222> LOCATION: (1)..(35)
<223> OTHER INFORMATION: Lipobox (+ signal peptide)
<220> FEATURE:
<221> NAME/KEY: MISC_FEATURE
<222> LOCATION: (2)..(12)
<223> OTHER INFORMATION: "X" on pos. 2 can be any amino acid, on pos.
      3 to 12 any amino acid or absent
<220> FEATURE:
<221> NAME/KEY: MISC_FEATURE
<222> LOCATION: (15)..(31)
<223> OTHER INFORMATION: "X" on pos. 15 to 21 can be D, E, R or K; on
      pos. 22 to 31 "X" can be D, E, R or K or absent
<220> FEATURE:
<221> NAME/KEY: MISC_FEATURE
<222> LOCATION: (32)..(32)
<223> OTHER INFORMATION: "X" stands for L, V, F, T, I, M or G
<220> FEATURE:
<221> NAME/KEY: MISC_FEATURE
<222> LOCATION: (33)..(33)
<223> OTHER INFORMATION: "X" stands for A, S, T, I, V, G, M, L, C, P,
      F or L
<220> FEATURE:
<221> NAME/KEY: MISC_FEATURE
<222> LOCATION: (34)..(34)
<223> OTHER INFORMATION: "X" stands for A, G, L, I, S, V, T, F or P
<220> FEATURE:
<221> NAME/KEY: MISC_FEATURE
<222> LOCATION: (13)..(13)
<223> OTHER INFORMATION: "X" stands for R or K
<220> FEATURE:
<221> NAME/KEY: MISC_FEATURE
<222> LOCATION: (14)..(14)
<223> OTHER INFORMATION: "X" can be any amino acid

<400> SEQUENCE: 3

Met Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30
```

```
Xaa Xaa Cys
        35

<210> SEQ ID NO 4
<211> LENGTH: 5
<212> TYPE: PRT
<213> ORGANISM: Streptococcus pneumoniae
<220> FEATURE:
<221> NAME/KEY: MISC_FEATURE
<222> LOCATION: (3)..(3)
<223> OTHER INFORMATION: "X" can be any amino acid

<400> SEQUENCE: 4

Leu Pro Xaa Thr Gly
1               5

<210> SEQ ID NO 5
<211> LENGTH: 15
<212> TYPE: PRT
<213> ORGANISM: Artificial Sequence
<220> FEATURE:
<223> OTHER INFORMATION: linker

<400> SEQUENCE: 5

Gly Gly Gly Gly Ser Gly Gly Gly Gly Ser Gly Gly Gly Gly Ser
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: linker

<400> SEQUENCE: 6

Glu Ser Gly Arg Ser Gly Gly Gly Ser Gly Gly Gly Gly Gly Ser
1               5                   10                  15

<210> SEQ ID NO 7
<211> LENGTH: 14
<212> TYPE: PRT
<213> ORGANISM: Artificial Sequence
<220> FEATURE:
<223> OTHER INFORMATION: linker

<400> SEQUENCE: 7

Glu Gly Lys Ser Ser Gly Ser Gly Ser Glu Ser Lys Ser Thr
1               5                   10

<210> SEQ ID NO 8
<211> LENGTH: 15
<212> TYPE: PRT
<213> ORGANISM: Artificial Sequence
<220> FEATURE:
<223> OTHER INFORMATION: linker

<400> SEQUENCE: 8

Glu Gly Lys Ser Ser Gly Ser Gly Ser Glu Ser Lys Ser Thr Gln
1               5                   10                  15

<210> SEQ ID NO 9
<211> LENGTH: 14
<212> TYPE: PRT
<213> ORGANISM: Artificial Sequence
<220> FEATURE:
<223> OTHER INFORMATION: linker

<400> SEQUENCE: 9
```

```
Glu Gly Lys Ser Ser Gly Ser Gly Ser Glu Ser Lys Val Asp
1               5                   10

<210> SEQ ID NO 10
<211> LENGTH: 14
<212> TYPE: PRT
<213> ORGANISM: Artificial Sequence
<220> FEATURE:
<223> OTHER INFORMATION: linker

<400> SEQUENCE: 10

Gly Ser Thr Ser Gly Ser Gly Lys Ser Ser Glu Gly Lys Gly
1               5                   10

<210> SEQ ID NO 11
<211> LENGTH: 18
<212> TYPE: PRT
<213> ORGANISM: Artificial Sequence
<220> FEATURE:
<223> OTHER INFORMATION: linker

<400> SEQUENCE: 11

Lys Glu Ser Gly Ser Val Ser Ser Glu Gln Leu Ala Gln Phe Arg Ser
1               5                   10                  15

Leu Asp

<210> SEQ ID NO 12
<211> LENGTH: 16
<212> TYPE: PRT
<213> ORGANISM: Artificial Sequence
<220> FEATURE:
<223> OTHER INFORMATION: linker

<400> SEQUENCE: 12

Glu Ser Gly Ser Val Ser Ser Glu Glu Leu Ala Phe Arg Ser Leu Asp
1               5                   10                  15

<210> SEQ ID NO 13
<211> LENGTH: 4
<212> TYPE: PRT
<213> ORGANISM: Artificial Sequence
<220> FEATURE:
<223> OTHER INFORMATION: endoplasmic reticulum localization signal

<400> SEQUENCE: 13

Lys Asp Glu Leu
1

<210> SEQ ID NO 14
<211> LENGTH: 4
<212> TYPE: PRT
<213> ORGANISM: Artificial Sequence
<220> FEATURE:
<223> OTHER INFORMATION: endoplasmic reticulum localization signal

<400> SEQUENCE: 14

Asp Asp Glu Leu
1

<210> SEQ ID NO 15
<211> LENGTH: 4
<212> TYPE: PRT
<213> ORGANISM: Artificial Sequence
<220> FEATURE:
<223> OTHER INFORMATION: endoplasmic reticulum localization signal

<400> SEQUENCE: 15
```

Asp Glu Glu Leu
1

<210> SEQ ID NO 16
<211> LENGTH: 4
<212> TYPE: PRT
<213> ORGANISM: Artificial Sequence
<220> FEATURE:
<223> OTHER INFORMATION: endoplasmic reticulum localization signal

<400> SEQUENCE: 16

Gln Glu Asp Leu
1

<210> SEQ ID NO 17
<211> LENGTH: 4
<212> TYPE: PRT
<213> ORGANISM: Artificial Sequence
<220> FEATURE:
<223> OTHER INFORMATION: endoplasmic reticulum localization signal

<400> SEQUENCE: 17

Arg Asp Glu Leu
1

<210> SEQ ID NO 18
<211> LENGTH: 7
<212> TYPE: PRT
<213> ORGANISM: Artificial Sequence
<220> FEATURE:
<223> OTHER INFORMATION: nucleus localization signal

<400> SEQUENCE: 18

Pro Lys Lys Lys Arg Lys Val
1               5

<210> SEQ ID NO 19
<211> LENGTH: 7
<212> TYPE: PRT
<213> ORGANISM: Artificial Sequence
<220> FEATURE:
<223> OTHER INFORMATION: nucleus localization signal

<400> SEQUENCE: 19

Pro Gln Lys Lys Ile Lys Ser
1               5

<210> SEQ ID NO 20
<211> LENGTH: 5
<212> TYPE: PRT
<213> ORGANISM: Artificial Sequence
<220> FEATURE:
<223> OTHER INFORMATION: nucleus localization signal

<400> SEQUENCE: 20

Gln Pro Lys Lys Pro
1               5

<210> SEQ ID NO 21
<211> LENGTH: 4
<212> TYPE: PRT
<213> ORGANISM: Artificial Sequence
<220> FEATURE:
<223> OTHER INFORMATION: nucleus localization signal

<400> SEQUENCE: 21

Arg Lys Lys Arg
1

```
<210> SEQ ID NO 22
<211> LENGTH: 12
<212> TYPE: PRT
<213> ORGANISM: Artificial Sequence
<220> FEATURE:
<223> OTHER INFORMATION: nucleolar region localization signal

<400> SEQUENCE: 22

Arg Lys Lys Arg Arg Gln Arg Arg Arg Ala His Gln
1               5                   10

<210> SEQ ID NO 23
<211> LENGTH: 16
<212> TYPE: PRT
<213> ORGANISM: Artificial Sequence
<220> FEATURE:
<223> OTHER INFORMATION: nucleolar region localization signal

<400> SEQUENCE: 23

Arg Gln Ala Arg Arg Asn Arg Arg Arg Arg Trp Arg Glu Arg Gln Arg
1               5                   10                  15

<210> SEQ ID NO 24
<211> LENGTH: 18
<212> TYPE: PRT
<213> ORGANISM: Artificial Sequence
<220> FEATURE:
<223> OTHER INFORMATION: nucleolar region localization signal

<400> SEQUENCE: 24

Met Pro Leu Thr Arg Arg Pro Ala Ala Ser Gln Ala Leu Ala Pro Pro
1               5                   10                  15

Thr Pro

<210> SEQ ID NO 25
<211> LENGTH: 8
<212> TYPE: PRT
<213> ORGANISM: Artificial Sequence
<220> FEATURE:
<223> OTHER INFORMATION: endosomal localization signal

<400> SEQUENCE: 25

Met Asp Asp Gln Arg Asp Leu Ile
1               5

<210> SEQ ID NO 26
<211> LENGTH: 7
<212> TYPE: PRT
<213> ORGANISM: Artificial Sequence
<220> FEATURE:
<223> OTHER INFORMATION: compartment localization signal

<400> SEQUENCE: 26

Ser Asn Asn Glu Gln Leu Pro
1               5

<210> SEQ ID NO 27
<211> LENGTH: 32
<212> TYPE: PRT
<213> ORGANISM: Artificial Sequence
<220> FEATURE:
<223> OTHER INFORMATION: mitochondrial matrix localization signal
<220> FEATURE:
<221> NAME/KEY: MISC_FEATURE
<222> LOCATION: (7)..(8)
<223> OTHER INFORMATION: "X" can be any amino acid
<220> FEATURE:
```

```
<221> NAME/KEY: MISC_FEATURE
<222> LOCATION: (32)..(32)
<223> OTHER INFORMATION: "X" can be any amino acid

<400> SEQUENCE: 27

Met Leu Phe Asn Leu Arg Xaa Xaa Leu Asn Asn Ala Ala Phe Arg His
1               5                   10                  15

Gly His Asn Phe Met Val Arg Asn Phe Arg Cys Gly Gln Pro Leu Xaa
            20                  25                  30

<210> SEQ ID NO 28
<211> LENGTH: 8
<212> TYPE: PRT
<213> ORGANISM: Artificial Sequence
<220> FEATURE:
<223> OTHER INFORMATION: plasma membrane localization signal

<400> SEQUENCE: 28

Gly Cys Val Cys Ser Ser Asn Pro
1               5

<210> SEQ ID NO 29
<211> LENGTH: 8
<212> TYPE: PRT
<213> ORGANISM: Artificial Sequence
<220> FEATURE:
<223> OTHER INFORMATION: plasma membrane localization signal

<400> SEQUENCE: 29

Gly Gln Thr Val Thr Thr Pro Leu
1               5

<210> SEQ ID NO 30
<211> LENGTH: 8
<212> TYPE: PRT
<213> ORGANISM: Artificial Sequence
<220> FEATURE:
<223> OTHER INFORMATION: plasma membrane localization signal

<400> SEQUENCE: 30

Gly Gln Glu Leu Ser Gln His Glu
1               5

<210> SEQ ID NO 31
<211> LENGTH: 8
<212> TYPE: PRT
<213> ORGANISM: Artificial Sequence
<220> FEATURE:
<223> OTHER INFORMATION: plasma membrane localization signal

<400> SEQUENCE: 31

Gly Asn Ser Pro Ser Tyr Asn Pro
1               5

<210> SEQ ID NO 32
<211> LENGTH: 8
<212> TYPE: PRT
<213> ORGANISM: Artificial Sequence
<220> FEATURE:
<223> OTHER INFORMATION: plasma membrane localization signal

<400> SEQUENCE: 32

Gly Val Ser Gly Ser Lys Gly Gln
1               5

<210> SEQ ID NO 33
<211> LENGTH: 8
```

```
<212> TYPE: PRT
<213> ORGANISM: Artificial Sequence
<220> FEATURE:
<223> OTHER INFORMATION: plasma membrane localization signal

<400> SEQUENCE: 33

Gly Gln Thr Ile Thr Thr Pro Leu
1               5

<210> SEQ ID NO 34
<211> LENGTH: 8
<212> TYPE: PRT
<213> ORGANISM: Artificial Sequence
<220> FEATURE:
<223> OTHER INFORMATION: plasma membrane localization signal

<400> SEQUENCE: 34

Gly Gln Thr Leu Thr Thr Pro Leu
1               5

<210> SEQ ID NO 35
<211> LENGTH: 8
<212> TYPE: PRT
<213> ORGANISM: Artificial Sequence
<220> FEATURE:
<223> OTHER INFORMATION: plasma membrane localization signal

<400> SEQUENCE: 35

Gly Gln Ile Phe Ser Arg Ser Ala
1               5

<210> SEQ ID NO 36
<211> LENGTH: 8
<212> TYPE: PRT
<213> ORGANISM: Artificial Sequence
<220> FEATURE:
<223> OTHER INFORMATION: plasma membrane localization signal

<400> SEQUENCE: 36

Gly Gln Ile His Gly Leu Ser Pro
1               5

<210> SEQ ID NO 37
<211> LENGTH: 8
<212> TYPE: PRT
<213> ORGANISM: Artificial Sequence
<220> FEATURE:
<223> OTHER INFORMATION: plasma membrane localization signal

<400> SEQUENCE: 37

Gly Ala Arg Ala Ser Val Leu Ser
1               5

<210> SEQ ID NO 38
<211> LENGTH: 8
<212> TYPE: PRT
<213> ORGANISM: Artificial Sequence
<220> FEATURE:
<223> OTHER INFORMATION: plasma membrane localization signal

<400> SEQUENCE: 38

Gly Cys Thr Leu Ser Ala Glu Glu
1               5

<210> SEQ ID NO 39
<211> LENGTH: 942
<212> TYPE: DNA
<213> ORGANISM: Streptococcus pneumoniae D39
```

```
<220> FEATURE:
<221> NAME/KEY: CDS
<222> LOCATION: (1)..(942)
<223> OTHER INFORMATION: CDS

<400> SEQUENCE: 39
atgaagaaaa aattattggc aggtgccatc acactattat cagtagcaac tttagcagct      60
tgttcgaaag ggtcagaagg tgcagacctt atcagcatga aggggatgt cattacagaa     120 catcaatttt atgagcaagt gaaaagcaac ccttcagccc aacaagtctt gttaaatatg     180
accatccaaa aagttttga aaacaatat ggctcagagc ttgatgataa agaggttgat       240
gatactattg ccgaagaaaa aaacaatat ggcgaaaact accaacgtgt cttgtcacaa      300
gcaggtatga ctcttgaaac acgtaaagct caaattcgta caagtaaatt agttgagttg     360
gcagttaaga aggtagcaga agctgaattg acagatgaag cctataagaa agcctttgat     420
gagtacactc cagatgtaac ggctcaaatc atccgtctta ataatgaaga taaggccaaa     480
gaagttctcg aaaaagccaa ggcagaaggt gctgattttg ctcaattagc caagataat     540 tcaactgatg aaaaaacaaa agaaaatggt ggagaaatta cctttgattc tgcttcaaca    600
gaagtacctg agcaagtcaa aaaagccgct ttcgctttag atgtggatgg tgtttctgat    660
gtgattacag caactggcac acaagcctac agtagccaat attacattgt aaaactcact    720
aagaaaacga aaaatcatc taatattgat gactacaaag aaaaattaaa aactgttatc     780
ttgactcaaa acaaaatga ttcaacattt gttcaaagca ttatcggaaa agaattgcaa     840
gcagccaata tcaaggttaa ggaccaagcc ttccaaaata tctttaccca atatatcggt    900
ggtggagatt caagctcaag cagtagtaca tcaaacgaat ag                       942

<210> SEQ ID NO 40
<211> LENGTH: 313
<212> TYPE: PRT
<213> ORGANISM: Streptococcus pneumoniae D39

<400> SEQUENCE: 40

Met Lys Lys Lys Leu Leu Ala Gly Ala Ile Thr Leu Leu Ser Val Ala
1               5                   10                  15

Thr Leu Ala Ala Cys Ser Lys Gly Ser Glu Gly Ala Asp Leu Ile Ser
            20                  25                  30

Met Lys Gly Asp Val Ile Thr Glu His Gln Phe Tyr Glu Gln Val Lys
        35                  40                  45

Ser Asn Pro Ser Ala Gln Gln Val Leu Leu Asn Met Thr Ile Gln Lys
    50                  55                  60

Val Phe Glu Lys Gln Tyr Gly Ser Glu Leu Asp Asp Lys Glu Val Asp
65                  70                  75                  80

Asp Thr Ile Ala Glu Glu Lys Lys Gln Tyr Gly Glu Asn Tyr Gln Arg
                85                  90                  95

Val Leu Ser Gln Ala Gly Met Thr Leu Glu Thr Arg Lys Ala Gln Ile
            100                 105                 110

Arg Thr Ser Lys Leu Val Glu Leu Ala Val Lys Lys Val Ala Glu Ala
        115                 120                 125

Glu Leu Thr Asp Glu Ala Tyr Lys Lys Ala Phe Asp Glu Tyr Thr Pro
    130                 135                 140

Asp Val Thr Ala Gln Ile Ile Arg Leu Asn Asn Glu Asp Lys Ala Lys
145                 150                 155                 160

Glu Val Leu Glu Lys Ala Lys Ala Glu Gly Ala Asp Phe Ala Gln Leu
                165                 170                 175
```

```
Ala Lys Asp Asn Ser Thr Asp Glu Lys Thr Lys Glu Asn Gly Gly Glu
            180                 185                 190

Ile Thr Phe Asp Ser Ala Ser Thr Glu Val Pro Glu Gln Val Lys Lys
        195                 200                 205

Ala Ala Phe Ala Leu Asp Val Asp Gly Val Ser Asp Val Ile Thr Ala
    210                 215                 220

Thr Gly Thr Gln Ala Tyr Ser Ser Gln Tyr Tyr Ile Val Lys Leu Thr
225                 230                 235                 240

Lys Lys Thr Glu Lys Ser Ser Asn Ile Asp Asp Tyr Lys Glu Lys Leu
                245                 250                 255

Lys Thr Val Ile Leu Thr Gln Lys Gln Asn Asp Ser Thr Phe Val Gln
            260                 265                 270

Ser Ile Ile Gly Lys Glu Leu Gln Ala Ala Asn Ile Lys Val Lys Asp
        275                 280                 285

Gln Ala Phe Gln Asn Ile Phe Thr Gln Tyr Ile Gly Gly Gly Asp Ser
    290                 295                 300

Ser Ser Ser Ser Ser Thr Ser Asn Glu
305                 310

<210> SEQ ID NO 41
<211> LENGTH: 300
<212> TYPE: PRT
<213> ORGANISM: Streptococcus pneumoniae
<220> FEATURE:
<221> NAME/KEY: SITE
<222> LOCATION: (1)..(300)
<223> OTHER INFORMATION: His-tag on pos. 3 to 8

<400> SEQUENCE: 41

Met Ala His His His His His His Ser Lys Gly Ser Glu Gly Ala Asp
1               5                   10                  15

Leu Ile Ser Met Lys Gly Asp Val Ile Thr Glu His Gln Phe Tyr Glu
            20                  25                  30

Gln Val Lys Ser Asn Pro Ser Ala Gln Gln Val Leu Leu Asn Met Thr
        35                  40                  45

Ile Gln Lys Val Phe Glu Lys Gln Tyr Gly Ser Glu Leu Asp Asp Lys
    50                  55                  60

Glu Val Asp Asp Thr Ile Ala Glu Glu Lys Lys Gln Tyr Gly Glu Asn
65                  70                  75                  80

Tyr Gln Arg Val Leu Ser Gln Ala Gly Met Thr Leu Glu Thr Arg Lys
                85                  90                  95

Ala Gln Ile Arg Thr Ser Lys Leu Val Glu Leu Ala Val Lys Lys Val
            100                 105                 110

Ala Glu Ala Glu Leu Thr Asp Glu Ala Tyr Lys Lys Ala Phe Asp Glu
        115                 120                 125

Tyr Thr Pro Asp Val Thr Ala Gln Ile Ile Arg Leu Asn Asn Glu Asp
    130                 135                 140

Lys Ala Lys Glu Val Leu Glu Lys Ala Lys Ala Glu Gly Ala Asp Phe
145                 150                 155                 160

Ala Gln Leu Ala Lys Asp Asn Ser Thr Asp Lys Thr Lys Glu Asn
                165                 170                 175

Gly Gly Glu Ile Thr Phe Asp Ser Ala Ser Thr Glu Val Pro Glu Gln
            180                 185                 190

Val Lys Lys Ala Ala Phe Ala Leu Asp Val Asp Gly Val Ser Asp Val
        195                 200                 205

Ile Thr Ala Thr Gly Thr Gln Ala Tyr Ser Ser Gln Tyr Tyr Ile Val
    210                 215                 220
```

```
Lys Leu Thr Lys Lys Thr Glu Lys Ser Ser Asn Ile Asp Asp Tyr Lys
225                 230                 235                 240

Glu Lys Leu Lys Thr Val Ile Leu Thr Gln Lys Gln Asn Asp Ser Thr
            245                 250                 255

Phe Val Gln Ser Ile Ile Gly Lys Glu Leu Gln Ala Ala Asn Ile Lys
        260                 265                 270

Val Lys Asp Gln Ala Phe Gln Asn Ile Phe Thr Gln Tyr Ile Gly Gly
    275                 280                 285

Gly Asp Ser Ser Ser Ser Ser Thr Ser Asn Glu
    290                 295                 300

<210> SEQ ID NO 42
<211> LENGTH: 49
<212> TYPE: DNA
<213> ORGANISM: Artificial Sequence
<220> FEATURE:
<223> OTHER INFORMATION: Primer

<400> SEQUENCE: 42
tttactgcat atgcaccatc accatcacca tagcagcgtc caacgcagt            49

<210> SEQ ID NO 43
<211> LENGTH: 27
<212> TYPE: DNA
<213> ORGANISM: Artificial Sequence
<220> FEATURE:
<223> OTHER INFORMATION: Primer

<400> SEQUENCE: 43
cattaggatc caatcgctgg ggaagtg                                     27

<210> SEQ ID NO 44
<211> LENGTH: 804
<212> TYPE: DNA
<213> ORGANISM: Streptococcus pneumoniae D39
<220> FEATURE:
<221> NAME/KEY: CDS
<222> LOCATION: (1)..(804)
<223> OTHER INFORMATION: CDS

<400> SEQUENCE: 44
atgaaaaaac tagcaaccct tcttttactg tctactgtag ccctagctgg gtgtagcagc    60
gtccaacgca gtctgcgtgg tgatgattat gttgattcca gtcttgctgc tgaagaaagt   120
tccaaagtag ctgcccaatc tgccaaggag ttaaacgatg ctttaacaaa cgaaaacgcc   180
aatttcccac aactatctaa ggaagttgct gaagatgaag ccgaagtgat tttccacaca   240
agccaaggtg atattcgcat taaactcttc cctaaactcg ctcctctagc ggttgaaaat   300
ttcctcactc acgccaaaga aggctactat aacggtatta ccttccaccg tgtcatcgat   360
ggctttatgg tccaaactgg agatccaaaa ggggacggta caggtggtca gtccatctgg   420
catgacaagg ataagactaa agacaaagga actggtttca agaacgagat tactccttat   480
ttgtataaca tccgtggtgc tcttgctatg gctaatactg tcaaccaaa  caccaatggc   540 agccagttct tcatcaacca aaactctaca gatacctctt ctaaactccc tacaagcaag   600
tatccacaga aaattattga agcctacaaa gaaggtggaa accctagtct agatggcaaa   660
cacccagtct ttggtcaagt gattgacggt atggatgttg tggataagat tgctaaggcc   720
gaaaaagatg aaaaagacaa gccaactact gctatcacaa tcgacagcat cgaagtggtg   780
aaagactacg attttaaatc ttaa                                          804
```

<210> SEQ ID NO 45
<211> LENGTH: 267
<212> TYPE: PRT
<213> ORGANISM: Streptococcus pneumoniae D39

<400> SEQUENCE: 45

Met Lys Lys Leu Ala Thr Leu Leu Leu Ser Thr Val Ala Leu Ala
1               5                   10                  15

Gly Cys Ser Ser Val Gln Arg Ser Leu Arg Gly Asp Asp Tyr Val Asp
            20                  25                  30

Ser Ser Leu Ala Ala Glu Glu Ser Ser Lys Val Ala Ala Gln Ser Ala
            35                  40                  45

Lys Glu Leu Asn Asp Ala Leu Thr Asn Glu Asn Ala Asn Phe Pro Gln
50                  55                  60

Leu Ser Lys Glu Val Ala Glu Asp Glu Ala Glu Val Ile Phe His Thr
65                  70                  75                  80

Ser Gln Gly Asp Ile Arg Ile Lys Leu Phe Pro Lys Leu Ala Pro Leu
                85                  90                  95

Ala Val Glu Asn Phe Leu Thr His Ala Lys Glu Gly Tyr Tyr Asn Gly
            100                 105                 110

Ile Thr Phe His Arg Val Ile Asp Gly Phe Met Val Gln Thr Gly Asp
            115                 120                 125

Pro Lys Gly Asp Gly Thr Gly Gly Gln Ser Ile Trp His Asp Lys Asp
            130                 135                 140

Lys Thr Lys Asp Lys Gly Thr Gly Phe Lys Asn Glu Ile Thr Pro Tyr
145                 150                 155                 160

Leu Tyr Asn Ile Arg Gly Ala Leu Ala Met Ala Asn Thr Gly Gln Pro
                165                 170                 175

Asn Thr Asn Gly Ser Gln Phe Phe Ile Asn Gln Asn Ser Thr Asp Thr
            180                 185                 190

Ser Ser Lys Leu Pro Thr Ser Lys Tyr Pro Gln Lys Ile Ile Glu Ala
            195                 200                 205

Tyr Lys Glu Gly Gly Asn Pro Ser Leu Asp Gly Lys His Pro Val Phe
            210                 215                 220

Gly Gln Val Ile Asp Gly Met Asp Val Val Lys Ile Ala Lys Ala
225                 230                 235                 240

Glu Lys Asp Glu Lys Asp Lys Pro Thr Thr Ala Ile Thr Ile Asp Ser
                245                 250                 255

Ile Glu Val Val Lys Asp Tyr Asp Phe Lys Ser
            260                 265

<210> SEQ ID NO 46
<211> LENGTH: 257
<212> TYPE: PRT
<213> ORGANISM: Streptococcus pneumoniae
<220> FEATURE:
<221> NAME/KEY: SITE
<222> LOCATION: (1)..(257)
<223> OTHER INFORMATION: His-tag on pos. 3 to 8

<400> SEQUENCE: 46

Met Ala His His His His His His Ser Ser Val Gln Arg Ser Leu Arg
1               5                   10                  15

Gly Asp Asp Tyr Val Asp Ser Ser Leu Ala Ala Glu Glu Ser Ser Lys
            20                  25                  30

Val Ala Ala Gln Ser Ala Lys Glu Leu Asn Asp Ala Leu Thr Asn Glu
            35                  40                  45

```
Asn Ala Asn Phe Pro Gln Leu Ser Lys Glu Val Ala Glu Asp Glu Ala
 50                  55                  60
Glu Val Ile Phe His Thr Ser Gln Gly Asp Ile Arg Ile Lys Leu Phe
 65                  70                  75                  80
Pro Lys Leu Ala Pro Leu Ala Val Glu Asn Phe Leu Thr His Ala Lys
                 85                  90                  95
Glu Gly Tyr Tyr Asn Gly Ile Thr Phe His Arg Val Ile Asp Gly Phe
            100                 105                 110
Met Val Gln Thr Gly Asp Pro Lys Gly Asp Gly Thr Gly Gly Gln Ser
        115                 120                 125
Ile Trp His Asp Lys Asp Lys Thr Lys Asp Lys Gly Thr Gly Phe Lys
    130                 135                 140
Asn Glu Ile Thr Pro Tyr Leu Tyr Asn Ile Arg Gly Ala Leu Ala Met
145                 150                 155                 160
Ala Asn Thr Gly Gln Pro Asn Thr Asn Gly Ser Gln Phe Phe Ile Asn
                165                 170                 175
Gln Asn Ser Thr Asp Thr Ser Ser Lys Leu Pro Thr Ser Lys Tyr Pro
            180                 185                 190
Gln Lys Ile Ile Glu Ala Tyr Lys Glu Gly Gly Asn Pro Ser Leu Asp
        195                 200                 205
Gly Lys His Pro Val Phe Gly Gln Val Ile Asp Gly Met Asp Val Val
    210                 215                 220
Asp Lys Ile Ala Lys Ala Glu Lys Asp Glu Lys Asp Lys Pro Thr Thr
225                 230                 235                 240
Ala Ile Thr Ile Asp Ser Ile Glu Val Val Lys Asp Tyr Asp Phe Lys
                245                 250                 255
Ser

<210> SEQ ID NO 47
<211> LENGTH: 32
<212> TYPE: DNA
<213> ORGANISM: Artificial Sequence
<220> FEATURE:
<223> OTHER INFORMATION: Primer

<400> SEQUENCE: 47
caacatcaca tatgggacaa acagaaccag ag                              32

<210> SEQ ID NO 48
<211> LENGTH: 49
<212> TYPE: DNA
<213> ORGANISM: Artificial Sequence
<220> FEATURE:
<223> OTHER INFORMATION: Primer

<400> SEQUENCE: 48
acttagatct taatgatggt ggtgatgatg ggctttaaag attgctctc            49

<210> SEQ ID NO 49
<211> LENGTH: 6014
<212> TYPE: DNA
<213> ORGANISM: Streptococcus pneumoniae TIGR4
<220> FEATURE:
<221> NAME/KEY: CDS
<222> LOCATION: (1)..(6014)
<223> OTHER INFORMATION: CDS

<400> SEQUENCE: 49
atggaaaagt attttggtga aaacaagag cgttttcat ttagaaaatt atcagtagga    60
cttgtatctg caacgatttc aagtttattt tttatgtctg tattagctag ttcatctgtg  120
```

```
gatgctcaag aaactgcggg agttcactat aaatatgtgg cagattcaga gctatcatca      180
gaagaaaaga agcagcttgt ctatgatatt ccgacatacg tggagaatga tgatgaaact      240
tattatcttg tttataagtt aaattctcaa aatcaactgg cggaattgcc aaatactgga      300
agcaagaatg agaggcaagc cctagttgct ggtgctagct tagctgctat gggaatttta      360
atttttgctg tttccaagaa aaaggttaag aataaaacgg tattacattt agtattggtt      420
gcagggatag gaaatggtgt cttagtttca gtccatgctt tagaaaatca tcttttgcta      480
aattacaata cggactatga attgacctct ggagaaaaat tacctcttcc taaagagatt      540
tcaggttaca cttatattgg atatatcaaa gagggaaaaa cgacttctga gtctgaagta      600
agtaatcaaa agagttcagt tgccactcct acaaaacaac aaaaggtgga ttataatgtt      660
acaccgaatt ttgtagacca tccatcaaca gtacaagcta ttcaggaaca aacacctgtt      720
tcttcaacta agccgacaga agttcaagta gttgaaaaac ctttctctac tgaattaatc      780
aatccaagaa aagaagagaa acaatcttca gattctcaag aacaattagc cgaacataag      840
aatctagaaa cgaagaaaga ggagaagatt tctccaaaag aaaagactgg ggtaaataca      900
ttaaatccac aggatgaagt tttatcaggt caattgaaca aacctgaact cttatatcgt      960
gaggaaacta tggagacaaa aatagatttt caagaagaaa ttcaagaaaa tcctgattta     1020
gctgaaggaa ctgtaagagt aaaacaagaa ggtaaattag gtaagaaagt tgaaatcgtc     1080
agaatattct ctgtaaacaa ggaagaagtt tcgcgagaaa ttgtttcaac ttcaacgact     1140
gcgcctagtc aagaatagt cgaaaaaggt actaaaaaaa ctcaagttat aaaggaacaa     1200
cctgagactg gtgtagaaca taaggacgta cagtctggag ctattgttga acccgcaatt     1260
cagcctgagt tgcccgaagc tgtagtaagt gacaaaggcg aaccagaagt tcaacctaca     1320
ttacccgaag cagttgtgac cgacaaaggt gagactgagg ttcaaccaga gtcgccagat     1380
actgtggtaa gtgataaagg tgaaccgagt caggtagcac cgcttccaga atataagggt     1440
aatattgagc aagtaaaacc tgaaactccg gttgagaaga ccaaagaaca aggtccagaa     1500
aaaactgaag aagttccagt aaaaccaaca gaagaaacac cagtaaatcc aaatgaaggt     1560
actacagaag gaacctcaat tcaagaagca gaaaatccag ttcaacctgc agaagaatca     1620
acaacgaatt cagagaaagt atcaccagat acatctagca aaaatactgg ggaagtgtcc     1680
agtaatccta gtgattcgac aacctcagtt ggagaatcaa ataaaccaga acataatgac     1740
tctaaaaatg aaaattcaga aaaaactgta aagaagttc cagtaaatcc aaatgaaggc     1800
acagtagaag gtacctcaaa tcaagaaaca gaaaaaccag ttcaacctgc agaagaaaca     1860
caaacaaact ctgggaaaat agctaacgaa aatactggag aagtatccaa taaacctagt     1920
gattcaaaac caccagttga agaatcaaat caaccagaaa aaaacggaac tgcaacaaaa     1980
ccagaaaatt caggtaatac aacatcagag aatggacaaa cagaaccaga accatcaaac     2040
ggaaattcaa ctgaggatgt ttcaaccgaa tcaaacacat ccaattcaaa tggaaacgaa     2100
gaaattaaac aagaaaatga actagaccct gataaaaagg tagaagaacc agagaaaaca     2160
cttgaattaa gaaatgtttc cgacctagag ttatacagtt tgtcaaatgg tacttataaa     2220
caacacattt cgttagagca agttccaagc aatccaaata gctactttgt taaagtgaaa     2280
tcttcttcat tcaaagatgt ataacctacca gtagcatcaa tatcagagga aagaaaaaat     2340
gataaaatcc tttataaaat cacagcaaaa gtagagaagc ttcagcagga gatagaaagc     2400
agatataaag ataattttac cttctatcta gctaagaagg gaacagaaga aacaacaaac     2460
tttacttcct ttagtaatct ggtcaaagct ataaaccaaa atccctctgg aacctatcat     2520
```

```
ttagcggcca gcctgaatgc taacgaagtg gagcttggtc ctgatgaaag atcctatatc   2580
aaggacacct ttactggtcg tttaatcggt gaaaaagatg gcaagaatta tgctatctat   2640
aatttgaaaa aacctctgtt tgaaaacttg agtggtgcta cagtagaaaa actgagtcta   2700
aaaaatgttg ctatttcagg gaaagatgat atcggttcac tggcaaatga agctcagaat   2760
aacacaaaaa ttaagcaagt tcacgtcgat ggtgttctgg ctggtgaacg tggtatcggt   2820
ggtttgctgg ctaaggctga gcaatcaagc atcacagaga gcagtttcaa gggaagaatt   2880
atcaacactt atgaaacgac tgctgcctac aatatcggtg gtatggtcgg tcatttgaca   2940
ggtgacaagg ctttacttac taagtcaaaa gcgacagtag ccatttcatc taacacaaat   3000
acttcagatc agactgtggg tggacttgca ggcctagtag accgagatgc acagatccaa   3060
gatagctatg ctgaaggtga tatcaacaat gtcaagcact tggtagagt cgctggagtg    3120 gcaggcaatt tgtgggatcg aacttctggt gatgttaggc atgctggaag tttgaccaat   3180
gttctcagcg atgttaatgt aaccaacgga atgccatca ctggttacca ctataacgaa     3240
atgaaggtaa aggacacatt cagcagcaag gccaacagag tctacaatgt caccttggtc   3300
aaggatgagg tcgtcagcaa ggaatccttt gaagaaagag gaacaatgct agatgcttct   3360
caaattgcaa gcaaaaaagc agaaatcaat cctctcattt taccaacagt ggagccactt   3420
tcaacaagtg gcaaaaaaga cagtgatttt tctaaggtgg cctattatca agctaagcgc   3480
aacttgactt ataaaaacat tgaaaaattg ctacctttct acaacaaggc aaccatcgtc   3540
aaatacggaa acctggtcaa tgagaacagt cttttatatc aaaaagaact cttgtcagca   3600
gtcatgatga aggacaacca agtcatcaca gacattgttt ctaacaaaca gactgcaaac   3660
aaactcttgc ttcactacaa ggatgattta tctgagaagc tggatctcaa ataccagaat   3720
gatttcgcca aattagcaga atatagtctg gcaatactg gacttctcta tacgccaaac    3780
caattcctgt atgaccaaac ctctatcatc aagcaagtct tacctgactt acaaaaggtt   3840
gactatcatt cagaagccat cagaaagacg ctgggtattt ctccaaacgt caagcaaact   3900
gagctctatc tagaagacca gttcgccaaa acaaaacaac aactggaaga cagtttgaaa   3960
aaactcttgt cagcggatgc tggactggct agtgctaacc ccgtcactga aggttatctt   4020
gtagataaaa tcaaacgcaa caaggaagcc ttgctacttg gcttgaccta tctgaacgg    4080 tggtataact ttagctatgg tcaggtgaat gtcaaagacc tagttctgta ccatttggac   4140
ttctttggta aggggaatgc ttcaccatta gatactctga ttgagttggg taaatctggc   4200
tttaacaatc ttctagctaa gaataatgtc gatacttatg gtatcagtct tgccagtcaa   4260
catggaacga cagatttgtt tagcacgctg gaacattacc gaaaagtctt tttaccaaat   4320
acaagcaata atgactggtt taaatcagag actaaggctt acattgtcga agaaaaatcc   4380
actatcgaag aggtgaaaac gaagcaaggg ttagctggca ccaagtattc tatcggtgtt   4440
tatgatcgta tcacgagtgc cacatggaaa taccgcaata tggtcttgcc tctcctgacc   4500
ttgccagaga gatccgtatt tgtcatctcg accatgtcta gtctaggatt tggagcttat   4560
gatcgctacc gcagtagtga ccataaagcg ggcaaggctc tcaatgattt tgttgaagaa   4620
aatgcgcgtg aaacagccaa acgtcagcga gatcactacg attattggta tcgtatttta   4680
gacgacaatg cacgtgaaaa actttataga aatattttgc tttacgatgc ttataaattt   4740
ggcgatgata taccgtagg gaaagctaca gaagtggcag attttgataa tccaaatcct    4800
gcaatgcaac atttctttgg acctgttgga aataaagttg gcataatca cacggtgct    4860 tatgctacag gtgatgcagt ttattatatg ggttatcgaa tgttggataa ggatggagct   4920
```

```
attacttata cgcatgagat gacacatgac tcagatcagg acatttatct tggaggatat    4980
ggtcgaagaa gtggcttggg accagagttc tttgctaaag gattattaca agcaccagac    5040
catccagatg atgcgaccat taccatcaac tccatcttga acattcaaa atctgatagt     5100 acagaaagtc gacgattaca agtacttgat ccaactacaa gatttaataa tgcagatgat    5160
ttgaagcaat atgtccacaa catgtttgac gttgttttata tgttggaata tctcgaagga    5220
aattcaattc ttaaattgga tacgaatcaa aaacaacaac ttcttagaaa agttacaaat    5280
gagtaccatc ctgatcctga tggaaataag gtctatgcaa caaatgttgt cagaaatcta    5340
acagtagaag aagttgaaag actacgttca ttcaatgatt tgattgataa taatattctt    5400
tcgtctaggg aatatgcctc aggtaaatac gaaagaaatg gctacttcac tattaagtta    5460
tttgcaccga tttatgctgc attaagtaat gatataggaa cccaggtgac ctgatgggac    5520
gtcgtatagc ctatgaacta ctagctgcta aaggctttaa agatggtatg gtaccatata    5580
tctcaaacca atacgaagaa gaagccaaac aaaagggcaa gacaatcaat ctctacggta    5640
aaacaagagg tttggttaca gatgacttgg ttttggaaaa ggtatttaat aaccaatatc    5700
atacttggag tgagtttaag aaagctatgt atcaagaacg acaagatcag tttgatagat    5760
tgaacaaagt tactttttaat gatacaacac agccttggca aacatttgcc aagaaaacta    5820
caagcagtgt agatgaatta cagaaattaa tggacgttgc tgttcgtaag gatgcagaac    5880
acaattacta ccattggaat aactacaatc cagacataga tagtgaagtc cacaagctca    5940
agagagcaat ctttaaagcc tatcttgacc aaacaaatga ttttagaagt tcaattttttg    6000 agaataaaaa atag                                                      6014
```

<210> SEQ ID NO 50
<211> LENGTH: 2004
<212> TYPE: PRT
<213> ORGANISM: Streptococcus pneumoniae TIGR4

<400> SEQUENCE: 50

```
Met Glu Lys Tyr Phe Gly Glu Lys Gln Glu Arg Phe Ser Phe Arg Lys
1               5                   10                  15

Leu Ser Val Gly Leu Val Ser Ala Thr Ile Ser Ser Leu Phe Phe Met
                20                  25                  30

Ser Val Leu Ala Ser Ser Ser Val Asp Ala Gln Glu Thr Ala Gly Val
        35                  40                  45

His Tyr Lys Tyr Val Ala Asp Ser Glu Leu Ser Ser Glu Glu Lys Lys
    50                  55                  60

Gln Leu Val Tyr Asp Ile Pro Thr Tyr Val Glu Asn Asp Asp Glu Thr
65                  70                  75                  80

Tyr Tyr Leu Val Tyr Lys Leu Asn Ser Gln Asn Gln Leu Ala Glu Leu
                85                  90                  95

Pro Asn Thr Gly Ser Lys Asn Glu Arg Gln Ala Leu Val Ala Gly Ala
            100                 105                 110

Ser Leu Ala Ala Met Gly Ile Leu Ile Phe Ala Val Ser Lys Lys Lys
        115                 120                 125

Val Lys Asn Lys Thr Val Leu His Leu Val Leu Val Ala Gly Ile Gly
    130                 135                 140

Asn Gly Val Leu Val Ser Val His Ala Leu Glu Asn His Leu Leu Leu
145                 150                 155                 160

Asn Tyr Asn Thr Asp Tyr Glu Leu Thr Ser Gly Glu Lys Leu Pro Leu
                165                 170                 175
```

-continued

```
Pro Lys Glu Ile Ser Gly Tyr Thr Tyr Ile Gly Tyr Ile Lys Glu Gly
            180                 185                 190

Lys Thr Thr Ser Glu Ser Glu Val Ser Asn Gln Lys Ser Val Ala
            195                 200                 205

Thr Pro Thr Lys Gln Gln Lys Val Asp Tyr Asn Val Thr Pro Asn Phe
            210                 215                 220

Val Asp His Pro Ser Thr Val Gln Ala Ile Gln Glu Gln Thr Pro Val
225                 230                 235                 240

Ser Ser Thr Lys Pro Thr Glu Val Gln Val Val Glu Lys Pro Phe Ser
                    245                 250                 255

Thr Glu Leu Ile Asn Pro Arg Lys Glu Lys Gln Ser Ser Asp Ser
                    260                 265                 270

Gln Glu Gln Leu Ala Glu His Lys Asn Leu Glu Thr Lys Lys Glu Glu
            275                 280                 285

Lys Ile Ser Pro Lys Glu Lys Thr Gly Val Asn Thr Leu Asn Pro Gln
            290                 295                 300

Asp Glu Val Leu Ser Gly Gln Leu Asn Lys Pro Glu Leu Leu Tyr Arg
305                 310                 315                 320

Glu Glu Thr Met Glu Thr Lys Ile Asp Phe Gln Glu Ile Gln Glu
                    325                 330                 335

Asn Pro Asp Leu Ala Glu Gly Thr Val Arg Val Lys Gln Glu Gly Lys
            340                 345                 350

Leu Gly Lys Lys Val Glu Ile Val Arg Ile Phe Ser Val Asn Lys Glu
            355                 360                 365

Glu Val Ser Arg Glu Ile Val Ser Thr Ser Thr Ala Pro Ser Pro
            370                 375                 380

Arg Ile Val Glu Lys Gly Thr Lys Thr Gln Val Ile Lys Glu Gln
385                 390                 395                 400

Pro Glu Thr Gly Val Glu His Lys Asp Val Gln Ser Gly Ala Ile Val
                    405                 410                 415

Glu Pro Ala Ile Gln Pro Glu Leu Pro Glu Ala Val Val Ser Asp Lys
            420                 425                 430

Gly Glu Pro Glu Val Gln Pro Thr Leu Pro Glu Ala Val Val Thr Asp
            435                 440                 445

Lys Gly Glu Thr Glu Val Gln Pro Glu Ser Pro Asp Thr Val Ser
450                 455                 460

Asp Lys Gly Glu Pro Glu Gln Val Ala Pro Leu Pro Glu Tyr Lys Gly
465                 470                 475                 480

Asn Ile Glu Gln Val Lys Pro Glu Thr Pro Val Glu Lys Thr Lys Glu
                    485                 490                 495

Gln Gly Pro Glu Lys Thr Glu Val Pro Val Lys Pro Thr Glu Glu
                    500                 505                 510

Thr Pro Val Asn Pro Asn Glu Gly Thr Thr Glu Gly Thr Ser Ile Gln
            515                 520                 525

Glu Ala Glu Asn Pro Val Gln Pro Ala Glu Glu Ser Thr Thr Asn Ser
            530                 535                 540

Glu Lys Val Ser Pro Asp Thr Ser Ser Lys Asn Thr Gly Glu Val Ser
545                 550                 555                 560

Ser Asn Pro Ser Asp Ser Thr Thr Ser Val Gly Glu Ser Asn Lys Pro
                    565                 570                 575

Glu His Asn Asp Ser Lys Asn Glu Asn Ser Glu Lys Thr Val Glu Glu
            580                 585                 590

Val Pro Val Asn Pro Asn Glu Gly Thr Val Glu Gly Thr Ser Asn Gln
            595                 600                 605
```

```
Glu Thr Glu Lys Pro Val Gln Pro Ala Glu Thr Gln Thr Asn Ser
    610                 615                 620
Gly Lys Ile Ala Asn Glu Asn Thr Gly Glu Val Ser Asn Lys Pro Ser
625                 630                 635                 640
Asp Ser Lys Pro Pro Val Glu Ser Asn Gln Pro Glu Lys Asn Gly
                645                 650                 655
Thr Ala Thr Lys Pro Glu Asn Ser Gly Asn Thr Thr Ser Glu Asn Gly
                660                 665                 670
Gln Thr Glu Pro Glu Pro Ser Asn Gly Asn Ser Thr Glu Asp Val Ser
            675                 680                 685
Thr Glu Ser Asn Thr Ser Asn Ser Asn Gly Asn Glu Glu Ile Lys Gln
            690                 695                 700
Glu Asn Glu Leu Asp Pro Asp Lys Lys Val Glu Glu Pro Glu Lys Thr
705                 710                 715                 720
Leu Glu Leu Arg Asn Val Ser Asp Leu Glu Leu Tyr Ser Leu Ser Asn
                725                 730                 735
Gly Thr Tyr Lys Gln His Ile Ser Leu Glu Gln Val Pro Ser Asn Pro
                740                 745                 750
Asn Ser Tyr Phe Val Lys Val Lys Ser Ser Phe Lys Asp Val Tyr
            755                 760                 765
Leu Pro Val Ala Ser Ile Ser Glu Glu Arg Lys Asn Asp Lys Ile Leu
            770                 775                 780
Tyr Lys Ile Thr Ala Lys Val Glu Lys Leu Gln Gln Glu Ile Glu Ser
785                 790                 795                 800
Arg Tyr Lys Asp Asn Phe Thr Phe Tyr Leu Ala Lys Lys Gly Thr Glu
                805                 810                 815
Glu Thr Thr Asn Phe Thr Ser Phe Ser Asn Leu Val Lys Ala Ile Asn
                820                 825                 830
Gln Asn Pro Ser Gly Thr Tyr His Leu Ala Ala Ser Leu Asn Ala Asn
            835                 840                 845
Glu Val Glu Leu Gly Pro Asp Glu Arg Ser Tyr Ile Lys Asp Thr Phe
850                 855                 860
Thr Gly Arg Leu Ile Gly Glu Lys Asp Gly Lys Asn Tyr Ala Ile Tyr
865                 870                 875                 880
Asn Leu Lys Lys Pro Leu Phe Glu Asn Leu Ser Gly Ala Thr Val Glu
                885                 890                 895
Lys Leu Ser Leu Lys Asn Val Ala Ile Ser Gly Lys Asp Asp Ile Gly
                900                 905                 910
Ser Leu Ala Asn Glu Ala Gln Asn Asn Thr Lys Ile Lys Gln Val His
            915                 920                 925
Val Asp Gly Val Leu Ala Gly Arg Gly Ile Gly Gly Leu Leu Ala
930                 935                 940
Lys Ala Glu Gln Ser Ser Ile Thr Glu Ser Ser Phe Lys Gly Arg Ile
945                 950                 955                 960
Ile Asn Thr Tyr Glu Thr Thr Ala Ala Tyr Asn Ile Gly Gly Met Val
                965                 970                 975
Gly His Leu Thr Gly Asp Lys Ala Leu Leu Thr Lys Ser Lys Ala Thr
            980                 985                 990
Val Ala Ile Ser Ser Asn Thr Asn Thr Ser Asp Gln Thr Val Gly Gly
            995                 1000                1005
Leu Ala Gly Leu Val Asp Arg Asp Ala Gln Ile Gln Asp Ser Tyr
    1010                1015                1020
Ala Glu Gly Asp Ile Asn Asn Val Lys His Phe Gly Arg Val Ala
```

-continued

```
            1025                1030                1035

Gly Val Ala Gly Asn Leu Trp Asp Arg Thr Ser Gly Asp Val Arg
        1040                1045                1050

His Ala Gly Ser Leu Thr Asn Val Leu Ser Asp Val Asn Val Thr
        1055                1060                1065

Asn Gly Asn Ala Ile Thr Gly Tyr His Tyr Asn Glu Met Lys Val
        1070                1075                1080

Lys Asp Thr Phe Ser Ser Lys Ala Asn Arg Val Tyr Asn Val Thr
        1085                1090                1095

Leu Val Lys Asp Glu Val Val Ser Lys Glu Ser Phe Glu Glu Arg
        1100                1105                1110

Gly Thr Met Leu Asp Ala Ser Gln Ile Ala Ser Lys Lys Ala Glu
        1115                1120                1125

Ile Asn Pro Leu Ile Leu Pro Thr Val Glu Pro Leu Ser Thr Ser
        1130                1135                1140

Gly Lys Lys Asp Ser Asp Phe Ser Lys Val Ala Tyr Tyr Gln Ala
        1145                1150                1155

Lys Arg Asn Leu Thr Tyr Lys Asn Ile Glu Lys Leu Leu Pro Phe
        1160                1165                1170

Tyr Asn Lys Ala Thr Ile Val Lys Tyr Gly Asn Leu Val Asn Glu
        1175                1180                1185

Asn Ser Leu Leu Tyr Gln Lys Glu Leu Leu Ser Ala Val Met Met
        1190                1195                1200

Lys Asp Asn Gln Val Ile Thr Asp Ile Val Ser Asn Lys Gln Thr
        1205                1210                1215

Ala Asn Lys Leu Leu Leu His Tyr Lys Asp Asp Leu Ser Glu Lys
        1220                1225                1230

Leu Asp Leu Lys Tyr Gln Asn Asp Phe Ala Lys Leu Ala Glu Tyr
        1235                1240                1245

Ser Leu Gly Asn Thr Gly Leu Leu Tyr Thr Pro Asn Gln Phe Leu
        1250                1255                1260

Tyr Asp Gln Thr Ser Ile Ile Lys Gln Val Leu Pro Asp Leu Gln
        1265                1270                1275

Lys Val Asp Tyr His Ser Glu Ala Ile Arg Lys Thr Leu Gly Ile
        1280                1285                1290

Ser Pro Asn Val Lys Gln Thr Glu Leu Tyr Leu Glu Asp Gln Phe
        1295                1300                1305

Ala Lys Thr Lys Gln Gln Leu Glu Asp Ser Leu Lys Lys Leu Leu
        1310                1315                1320

Ser Ala Asp Ala Gly Leu Ala Ser Ala Asn Pro Val Thr Glu Gly
        1325                1330                1335

Tyr Leu Val Asp Lys Ile Lys Arg Asn Lys Glu Ala Leu Leu Leu
        1340                1345                1350

Gly Leu Thr Tyr Leu Glu Arg Trp Tyr Asn Phe Ser Tyr Gly Gln
        1355                1360                1365

Val Asn Val Lys Asp Leu Val Leu Tyr His Leu Asp Phe Phe Gly
        1370                1375                1380

Lys Gly Asn Ala Ser Pro Leu Asp Thr Leu Ile Glu Leu Gly Lys
        1385                1390                1395

Ser Gly Phe Asn Asn Leu Leu Ala Lys Asn Asn Val Asp Thr Tyr
        1400                1405                1410

Gly Ile Ser Leu Ala Ser Gln His Gly Thr Thr Asp Leu Phe Ser
        1415                1420                1425
```

-continued

Thr Leu Glu His Tyr Arg Lys Val Phe Leu Pro Asn Thr Ser Asn
1430                1435                1440

Asn Asp Trp Phe Lys Ser Glu Thr Lys Ala Tyr Ile Val Glu Glu
1445                1450                1455

Lys Ser Thr Ile Glu Glu Val Lys Thr Lys Gln Gly Leu Ala Gly
1460                1465                1470

Thr Lys Tyr Ser Ile Gly Val Tyr Asp Arg Ile Thr Ser Ala Thr
1475                1480                1485

Trp Lys Tyr Arg Asn Met Val Leu Pro Leu Leu Thr Leu Pro Glu
1490                1495                1500

Arg Ser Val Phe Val Ile Ser Thr Met Ser Ser Leu Gly Phe Gly
1505                1510                1515

Ala Tyr Asp Arg Tyr Arg Ser Ser Asp His Lys Ala Gly Lys Ala
1520                1525                1530

Leu Asn Asp Phe Val Glu Glu Asn Ala Arg Glu Thr Ala Lys Arg
1535                1540                1545

Gln Arg Asp His Tyr Asp Tyr Trp Tyr Arg Ile Leu Asp Asp Asn
1550                1555                1560

Ala Arg Glu Lys Leu Tyr Arg Asn Ile Leu Leu Tyr Asp Ala Tyr
1565                1570                1575

Lys Phe Gly Asp Asp Asn Thr Val Gly Lys Ala Thr Glu Val Ala
1580                1585                1590

Asp Phe Asp Asn Pro Asn Pro Ala Met Gln His Phe Phe Gly Pro
1595                1600                1605

Val Gly Asn Lys Val Gly His Asn Gln His Gly Ala Tyr Ala Thr
1610                1615                1620

Gly Asp Ala Val Tyr Tyr Met Gly Tyr Arg Met Leu Asp Lys Asp
1625                1630                1635

Gly Ala Ile Thr Tyr Thr His Glu Met Thr His Asp Ser Asp Gln
1640                1645                1650

Asp Ile Tyr Leu Gly Gly Tyr Gly Arg Arg Ser Gly Leu Gly Pro
1655                1660                1665

Glu Phe Phe Ala Lys Gly Leu Leu Gln Ala Pro Asp His Pro Asp
1670                1675                1680

Asp Ala Thr Ile Thr Ile Asn Ser Ile Leu Lys His Ser Lys Ser
1685                1690                1695

Asp Ser Thr Glu Ser Arg Arg Leu Gln Val Leu Asp Pro Thr Thr
1700                1705                1710

Arg Phe Asn Asn Ala Asp Asp Leu Lys Gln Tyr Val His Asn Met
1715                1720                1725

Phe Asp Val Val Tyr Met Leu Glu Tyr Leu Glu Gly Asn Ser Ile
1730                1735                1740

Leu Lys Leu Asp Thr Asn Gln Lys Gln Gln Leu Leu Arg Lys Val
1745                1750                1755

Thr Asn Glu Tyr His Pro Asp Pro Asp Gly Asn Lys Val Tyr Ala
1760                1765                1770

Thr Asn Val Val Arg Asn Leu Thr Val Glu Glu Val Glu Arg Leu
1775                1780                1785

Arg Ser Phe Asn Asp Leu Ile Asp Asn Asn Ile Leu Ser Ser Arg
1790                1795                1800

Glu Tyr Ala Ser Gly Lys Tyr Glu Arg Asn Gly Tyr Phe Thr Ile
1805                1810                1815

Lys Leu Phe Ala Pro Ile Tyr Ala Ala Leu Ser Asn Asp Ile Gly
1820                1825                1830

```
Thr Pro Gly Asp Leu Met Gly Arg Arg Ile Ala Tyr Glu Leu Leu
    1835                1840                1845

Ala Ala Lys Gly Phe Lys Asp Gly Met Val Pro Tyr Ile Ser Asn
    1850                1855                1860

Gln Tyr Glu Glu Glu Ala Lys Gln Lys Gly Lys Thr Ile Asn Leu
    1865                1870                1875

Tyr Gly Lys Thr Arg Gly Leu Val Thr Asp Asp Leu Val Leu Glu
    1880                1885                1890

Lys Val Phe Asn Asn Gln Tyr His Thr Trp Ser Glu Phe Lys Lys
    1895                1900                1905

Ala Met Tyr Gln Glu Arg Gln Asp Gln Phe Asp Arg Leu Asn Lys
    1910                1915                1920

Val Thr Phe Asn Asp Thr Thr Gln Pro Trp Gln Thr Phe Ala Lys
    1925                1930                1935

Lys Thr Thr Ser Ser Val Asp Glu Leu Gln Lys Leu Met Asp Val
    1940                1945                1950

Ala Val Arg Lys Asp Ala Glu His Asn Tyr Tyr His Trp Asn Asn
    1955                1960                1965

Tyr Asn Pro Asp Ile Asp Ser Glu Val His Lys Leu Lys Arg Ala
    1970                1975                1980

Ile Phe Lys Ala Tyr Leu Asp Gln Thr Asn Asp Phe Arg Ser Ser
    1985                1990                1995

Ile Phe Glu Asn Lys Lys
    2000

<210> SEQ ID NO 51
<211> LENGTH: 1323
<212> TYPE: PRT
<213> ORGANISM: Streptococcus pneumoniae
<220> FEATURE:
<221> NAME/KEY: SITE
<222> LOCATION: (1)..(1323)
<223> OTHER INFORMATION: His-tag on pos. 1318 to 1323

<400> SEQUENCE: 51

Met Gly Gln Thr Glu Pro Glu Pro Ser Asn Gly Asn Ser Thr Glu Asp
1               5                   10                  15

Val Ser Thr Glu Ser Asn Thr Ser Asn Ser Asn Gly Asn Glu Glu Ile
                20                  25                  30

Lys Gln Glu Asn Glu Leu Asp Pro Asp Lys Lys Val Glu Glu Pro Glu
            35                  40                  45

Lys Thr Leu Glu Leu Arg Asn Val Ser Asp Leu Glu Leu Tyr Ser Leu
        50                  55                  60

Ser Asn Gly Thr Tyr Lys Gln His Ile Ser Leu Glu Gln Val Pro Ser
65                  70                  75                  80

Asn Pro Asn Ser Tyr Phe Val Lys Val Lys Ser Ser Ser Phe Lys Asp
                85                  90                  95

Val Tyr Leu Pro Val Ala Ser Ile Ser Glu Glu Arg Lys Asn Asp Lys
            100                 105                 110

Ile Leu Tyr Lys Ile Thr Ala Lys Val Glu Lys Leu Gln Gln Glu Ile
        115                 120                 125

Glu Ser Arg Tyr Lys Asp Asn Phe Thr Phe Tyr Leu Ala Lys Lys Gly
    130                 135                 140

Thr Glu Glu Thr Thr Asn Phe Thr Ser Phe Ser Asn Leu Val Lys Ala
145                 150                 155                 160

Ile Asn Gln Asn Pro Ser Gly Thr Tyr His Leu Ala Ala Ser Leu Asn
```

```
            165                 170                 175
Ala Asn Glu Val Glu Leu Gly Pro Asp Glu Arg Ser Tyr Ile Lys Asp
            180                 185                 190

Thr Phe Thr Gly Arg Leu Ile Gly Glu Lys Asp Gly Lys Asn Tyr Ala
            195                 200                 205

Ile Tyr Asn Leu Lys Lys Pro Leu Phe Glu Asn Leu Ser Gly Ala Thr
            210                 215                 220

Val Glu Lys Leu Ser Leu Lys Asn Val Ala Ile Ser Gly Lys Asp Asp
225                 230                 235                 240

Ile Gly Ser Leu Ala Asn Glu Ala Gln Asn Asn Thr Lys Ile Lys Gln
            245                 250                 255

Val His Val Asp Gly Val Leu Ala Gly Glu Arg Gly Ile Gly Gly Leu
            260                 265                 270

Leu Ala Lys Ala Glu Gln Ser Ser Ile Thr Glu Ser Ser Phe Lys Gly
            275                 280                 285

Arg Ile Ile Asn Thr Tyr Glu Thr Thr Ala Ala Tyr Asn Ile Gly Gly
            290                 295                 300

Met Val Gly His Leu Thr Gly Asp Lys Ala Leu Leu Thr Lys Ser Lys
305                 310                 315                 320

Ala Thr Val Ala Ile Ser Ser Asn Thr Asn Thr Ser Asp Gln Thr Val
            325                 330                 335

Gly Gly Leu Ala Gly Leu Val Asp Arg Asp Ala Gln Ile Gln Asp Ser
            340                 345                 350

Tyr Ala Glu Gly Asp Ile Asn Asn Val Lys His Phe Gly Arg Val Ala
            355                 360                 365

Gly Val Ala Gly Asn Leu Trp Asp Arg Thr Ser Gly Asp Val Arg His
            370                 375                 380

Ala Gly Ser Leu Thr Asn Val Leu Ser Asp Val Asn Val Thr Asn Gly
385                 390                 395                 400

Asn Ala Ile Thr Gly Tyr His Tyr Asn Glu Met Lys Val Lys Asp Thr
            405                 410                 415

Phe Ser Ser Lys Ala Asn Arg Val Tyr Asn Val Thr Leu Val Lys Asp
            420                 425                 430

Glu Val Val Ser Lys Glu Ser Phe Glu Glu Arg Gly Thr Met Leu Asp
            435                 440                 445

Ala Ser Gln Ile Ala Ser Lys Lys Ala Glu Ile Asn Pro Leu Ile Leu
            450                 455                 460

Pro Thr Val Glu Pro Leu Ser Thr Ser Gly Lys Lys Asp Ser Asp Phe
465                 470                 475                 480

Ser Lys Val Ala Tyr Tyr Gln Ala Lys Arg Asn Leu Thr Tyr Lys Asn
            485                 490                 495

Ile Glu Lys Leu Leu Pro Phe Tyr Asn Lys Ala Thr Ile Val Lys Tyr
            500                 505                 510

Gly Asn Leu Val Asn Glu Asn Ser Leu Leu Tyr Gln Lys Glu Leu Leu
            515                 520                 525

Ser Ala Val Met Met Lys Asp Asn Gln Val Ile Thr Asp Ile Val Ser
530                 535                 540

Asn Lys Gln Thr Ala Asn Lys Leu Leu Leu His Tyr Lys Asp Asp Leu
545                 550                 555                 560

Ser Glu Lys Leu Asp Leu Lys Tyr Gln Asn Asp Phe Ala Lys Leu Ala
            565                 570                 575

Glu Tyr Ser Leu Gly Asn Thr Gly Leu Leu Tyr Thr Pro Asn Gln Phe
            580                 585                 590
```

```
Leu Tyr Asp Gln Thr Ser Ile Ile Lys Gln Val Leu Pro Asp Leu Gln
        595                 600                 605

Lys Val Asp Tyr His Ser Glu Ala Ile Arg Lys Thr Leu Gly Ile Ser
        610                 615                 620

Pro Asn Val Lys Gln Thr Glu Leu Tyr Leu Glu Asp Gln Phe Ala Lys
625                 630                 635                 640

Thr Lys Gln Gln Leu Glu Asp Ser Leu Lys Lys Leu Leu Ser Ala Asp
                645                 650                 655

Ala Gly Leu Ala Ser Ala Asn Pro Val Thr Glu Gly Tyr Leu Val Asp
            660                 665                 670

Lys Ile Lys Arg Asn Lys Glu Ala Leu Leu Leu Gly Leu Thr Tyr Leu
        675                 680                 685

Glu Arg Trp Tyr Asn Phe Ser Tyr Gly Gln Val Asn Val Lys Asp Leu
    690                 695                 700

Val Leu Tyr His Leu Asp Phe Phe Gly Lys Gly Asn Ala Ser Pro Leu
705                 710                 715                 720

Asp Thr Leu Ile Glu Leu Gly Lys Ser Gly Phe Asn Leu Leu Ala
                725                 730                 735

Lys Asn Asn Val Asp Thr Tyr Gly Ile Ser Leu Ala Ser Gln His Gly
            740                 745                 750

Thr Thr Asp Leu Phe Ser Thr Leu Glu His Tyr Arg Lys Val Phe Leu
        755                 760                 765

Pro Asn Thr Ser Asn Asn Asp Trp Phe Lys Ser Glu Thr Lys Ala Tyr
    770                 775                 780

Ile Val Glu Glu Lys Ser Thr Ile Glu Val Lys Thr Lys Gln Gly
785                 790                 795                 800

Leu Ala Gly Thr Lys Tyr Ser Ile Gly Val Tyr Asp Arg Ile Thr Ser
                805                 810                 815

Ala Thr Trp Lys Tyr Arg Asn Met Val Leu Pro Leu Thr Leu Pro
            820                 825                 830

Glu Arg Ser Val Phe Val Ile Ser Thr Met Ser Ser Leu Gly Phe Gly
        835                 840                 845

Ala Tyr Asp Arg Tyr Arg Ser Ser Asp His Lys Ala Gly Lys Ala Leu
    850                 855                 860

Asn Asp Phe Val Glu Glu Asn Ala Arg Glu Thr Ala Lys Arg Gln Arg
865                 870                 875                 880

Asp His Tyr Asp Tyr Trp Tyr Arg Ile Leu Asp Asp Asn Ala Arg Glu
                885                 890                 895

Lys Leu Tyr Arg Asn Ile Leu Leu Tyr Asp Ala Tyr Lys Phe Gly Asp
            900                 905                 910

Asp Asn Thr Val Gly Lys Ala Thr Glu Val Ala Asp Phe Asp Asn Pro
        915                 920                 925

Asn Pro Ala Met Gln His Phe Phe Gly Pro Val Gly Asn Lys Val Gly
    930                 935                 940

His Asn Gln His Gly Ala Tyr Ala Thr Gly Asp Ala Val Tyr Tyr Met
945                 950                 955                 960

Gly Tyr Arg Met Leu Asp Lys Asp Gly Ala Ile Thr Tyr Thr His Glu
                965                 970                 975

Met Thr His Asp Ser Asp Gln Asp Ile Tyr Leu Gly Gly Tyr Gly Arg
            980                 985                 990

Arg Ser Gly Leu Gly Pro Glu Phe  Phe Ala Lys Gly Leu Leu Gln Ala
        995                 1000                1005

Pro Asp  His Pro Asp Asp Ala  Thr Ile Thr Ile Asn  Ser Ile Leu
    1010                1015                1020
```

Lys His Ser Lys Ser Asp Ser Thr Glu Ser Arg Arg Leu Gln Val
    1025            1030            1035

Leu Asp Pro Thr Thr Arg Phe Asn Asn Ala Asp Asp Leu Lys Gln
    1040            1045            1050

Tyr Val His Asn Met Phe Asp Val Val Tyr Met Leu Glu Tyr Leu
    1055            1060            1065

Glu Gly Asn Ser Ile Leu Lys Leu Asp Thr Asn Gln Lys Gln Gln
    1070            1075            1080

Leu Leu Arg Lys Val Thr Asn Glu Tyr His Pro Asp Pro Asp Gly
    1085            1090            1095

Asn Lys Val Tyr Ala Thr Asn Val Val Arg Asn Leu Thr Val Glu
    1100            1105            1110

Glu Val Glu Arg Leu Arg Ser Phe Asn Asp Leu Ile Asp Asn Asn
    1115            1120            1125

Ile Leu Ser Ser Arg Glu Tyr Ala Ser Gly Lys Tyr Glu Arg Asn
    1130            1135            1140

Gly Tyr Phe Thr Ile Lys Leu Phe Ala Pro Ile Tyr Ala Ala Leu
    1145            1150            1155

Ser Asn Asp Ile Gly Thr Pro Gly Asp Leu Met Gly Arg Arg Ile
    1160            1165            1170

Ala Tyr Glu Leu Leu Ala Ala Lys Gly Phe Lys Asp Gly Met Val
    1175            1180            1185

Pro Tyr Ile Ser Asn Gln Tyr Glu Glu Ala Lys Gln Lys Gly
    1190            1195            1200

Lys Thr Ile Asn Leu Tyr Gly Lys Thr Arg Gly Leu Val Thr Asp
    1205            1210            1215

Asp Leu Val Leu Glu Lys Val Phe Asn Asn Gln Tyr His Thr Trp
    1220            1225            1230

Ser Glu Phe Lys Lys Ala Met Tyr Gln Glu Arg Gln Asp Gln Phe
    1235            1240            1245

Asp Arg Leu Asn Lys Val Thr Phe Asn Asp Thr Thr Gln Pro Trp
    1250            1255            1260

Gln Thr Phe Ala Lys Lys Thr Thr Ser Ser Val Asp Glu Leu Gln
    1265            1270            1275

Lys Leu Met Asp Val Ala Val Arg Lys Asp Ala Glu His Asn Tyr
    1280            1285            1290

Tyr His Trp Asn Asn Tyr Asn Pro Asp Ile Asp Ser Glu Val His
    1295            1300            1305

Lys Leu Lys Arg Ala Ile Phe Lys Ala His His His His His
    1310            1315            1320

```
<210> SEQ ID NO 52
<211> LENGTH: 49
<212> TYPE: DNA
<213> ORGANISM: Artificial Sequence
<220> FEATURE:
<223> OTHER INFORMATION: Primer

<400> SEQUENCE: 52
ccatggctag ccaccatcac catcaccatg ctacaaactc aatcatcgc        49

<210> SEQ ID NO 53
<211> LENGTH: 31
<212> TYPE: DNA
<213> ORGANISM: Artificial Sequence
<220> FEATURE:
<223> OTHER INFORMATION: Primer
```

<400> SEQUENCE: 53
tttcggatcc ttattttgcc aatccttcag c                                        31

<210> SEQ ID NO 54
<211> LENGTH: 870
<212> TYPE: DNA
<213> ORGANISM: Streptococcus pneumoniae D39
<220> FEATURE:
<221> NAME/KEY: CDS
<222> LOCATION: (1)..(870)
<223> OTHER INFORMATION: CDS

<400> SEQUENCE: 54

| | | | | | |
|---|---|---|---|---|---|
| atgaaaaaat | taggtacatt | actcgttctc | tttctttctg | caatcattct | tgtagcatgt | 60 |
| gctagcggaa | aaaagatac | aacttctggt | caaaaactaa | agttgttgc | tacaaactca | 120 |
| ccgattgggc | aagacccaca | cgaatacgaa | ccacttcctg | aagacgttaa | gaaaacttct | 180 |
| gaggctgatt | tgattttcta | taacggtatc | aaccttgaaa | caggtggcaa | tgcttggttt | 240 |
| acaaaattgg | tagaaaatgc | caagaaaact | gaaacaaag | actacttcgc | agtcagcgac | 300 |
| ggcgttgatg | ttatctacct | tgaaggtcaa | atgaaaaag | gaaagaaga | cccacacgct | 360 |
| tggcttaacc | ttgaaaacgg | tattattttt | gctaaaaata | tcgccaaaca | attgagcgcc | 420 |
| aaagacccta | acaataaaga | attctatgaa | aaaaatctca | agaatatac | tgataagtta | 480 |
| gacaaacttg | ataagaaag | taaggataaa | tttaataaga | tccctgctga | aaagaaactc | 540 |
| attgtaacca | gcgaaggagc | attcaaatac | ttctctaaag | cctatggtgt | tccaagtgcc | 600 |
| tacatctggg | aaatcaatac | tgaagaagaa | ggaactcctg | aacaaatcaa | gaccttggtt | 660 |
| gaaaaacttc | gccaaacaaa | agttccatca | ctctttgtag | aatcaagtgt | ggatgaccgt | 720 |
| ccaatgaaaa | ctgtttctca | agacacaaac | atcccaatct | acgcacaaat | ctttactgac | 780 |
| tctatcgcag | aacaaggtaa | agaaggcgac | agctactaca | gcatgatgaa | atacaacctt | 840 |
| gacaagattg | ctgaaggatt | ggcaaaataa | | | | 870 |

<210> SEQ ID NO 55
<211> LENGTH: 309
<212> TYPE: PRT
<213> ORGANISM: Streptococcus pneumoniae D39

<400> SEQUENCE: 55

Met Lys Lys Leu Gly Thr Leu Leu Val Leu Phe Leu Ser Ala Ile Ile
1               5                   10                  15

Leu Val Ala Cys Ala Ser Gly Lys Lys Asp Thr Thr Ser Gly Gln Lys
            20                  25                  30

Leu Lys Val Val Ala Thr Asn Ser Ile Ile Ala Asp Ile Thr Lys Asn
        35                  40                  45

Ile Ala Gly Asp Lys Ile Asp Leu His Ser Ile Val Pro Ile Gly Gln
    50                  55                  60

Asp Pro His Glu Tyr Glu Pro Leu Pro Glu Asp Val Lys Lys Thr Ser
65                  70                  75                  80

Glu Ala Asp Leu Ile Phe Tyr Asn Gly Ile Asn Leu Glu Thr Gly Gly
                85                  90                  95

Asn Ala Trp Phe Thr Lys Leu Val Glu Asn Ala Lys Lys Thr Glu Asn
            100                 105                 110

Lys Asp Tyr Phe Ala Val Ser Asp Gly Val Asp Val Ile Tyr Leu Glu
        115                 120                 125

Gly Gln Asn Glu Lys Gly Lys Glu Asp Pro His Ala Trp Leu Asn Leu

```
            130                 135                 140
Glu Asn Gly Ile Ile Phe Ala Lys Asn Ile Ala Lys Gln Leu Ser Ala
145                 150                 155                 160

Lys Asp Pro Asn Asn Lys Glu Phe Tyr Glu Lys Asn Leu Lys Glu Tyr
                165                 170                 175

Thr Asp Lys Leu Asp Lys Leu Asp Lys Glu Ser Lys Asp Lys Phe Asn
            180                 185                 190

Lys Ile Pro Ala Glu Lys Lys Leu Ile Val Thr Ser Glu Gly Ala Phe
        195                 200                 205

Lys Tyr Phe Ser Lys Ala Tyr Gly Val Pro Ser Ala Tyr Ile Trp Glu
    210                 215                 220

Ile Asn Thr Glu Glu Glu Gly Thr Pro Glu Gln Ile Lys Thr Leu Val
225                 230                 235                 240

Glu Lys Leu Arg Gln Thr Lys Val Pro Ser Leu Phe Val Glu Ser Ser
                245                 250                 255

Val Asp Asp Arg Pro Met Lys Thr Val Ser Gln Asp Thr Asn Ile Pro
            260                 265                 270

Ile Tyr Ala Gln Ile Phe Thr Asp Ser Ile Ala Glu Gln Gly Lys Glu
        275                 280                 285

Gly Asp Ser Tyr Tyr Ser Met Met Lys Tyr Asn Leu Asp Lys Ile Ala
    290                 295                 300

Glu Gly Leu Ala Lys
305

<210> SEQ ID NO 56
<211> LENGTH: 280
<212> TYPE: PRT
<213> ORGANISM: Streptococcus pneumoniae
<220> FEATURE:
<221> NAME/KEY: SITE
<222> LOCATION: (1)..(280)
<223> OTHER INFORMATION: His-tag on pos. 3 to 8

<400> SEQUENCE: 56

Met Ala His His His His His His Thr Asn Ser Ile Ile Ala Asp Ile
1               5                   10                  15

Thr Lys Asn Ile Ala Gly Asp Lys Ile Asp Leu His Ser Ile Val Pro
            20                  25                  30

Ile Gly Gln Asp Pro His Glu Tyr Glu Pro Leu Pro Glu Asp Val Lys
        35                  40                  45

Lys Thr Ser Glu Ala Asp Leu Ile Phe Tyr Asn Gly Ile Asn Leu Glu
    50                  55                  60

Thr Gly Gly Asn Ala Trp Phe Thr Lys Leu Val Glu Asn Ala Lys Lys
65                  70                  75                  80

Thr Glu Asn Lys Asp Tyr Phe Ala Val Ser Asp Gly Val Asp Val Ile
                85                  90                  95

Tyr Leu Glu Gly Gln Asn Glu Lys Gly Lys Glu Asp Pro His Ala Trp
            100                 105                 110

Leu Asn Leu Glu Asn Gly Ile Ile Phe Ala Lys Asn Ile Ala Lys Gln
        115                 120                 125

Leu Ser Ala Lys Asp Pro Asn Asn Lys Glu Phe Tyr Glu Lys Asn Leu
    130                 135                 140

Lys Glu Tyr Thr Asp Lys Leu Asp Lys Leu Asp Lys Glu Ser Lys Asp
145                 150                 155                 160

Lys Phe Asn Lys Ile Pro Ala Glu Lys Lys Leu Ile Val Thr Ser Glu
                165                 170                 175
```

```
Gly Ala Phe Lys Tyr Phe Ser Lys Ala Tyr Gly Val Pro Ser Ala Tyr
                180                 185                 190

Ile Trp Glu Ile Asn Thr Glu Glu Gly Thr Pro Glu Gln Ile Lys
            195                 200                 205

Thr Leu Val Glu Lys Leu Arg Gln Thr Lys Val Pro Ser Leu Phe Val
    210                 215                 220

Glu Ser Ser Val Asp Asp Arg Pro Met Lys Thr Val Ser Gln Asp Thr
225                 230                 235                 240

Asn Ile Pro Ile Tyr Ala Gln Ile Phe Thr Asp Ser Ile Ala Glu Gln
                245                 250                 255

Gly Lys Glu Gly Asp Ser Tyr Tyr Ser Met Met Lys Tyr Asn Leu Asp
            260                 265                 270

Lys Ile Ala Glu Gly Leu Ala Lys
        275                 280

<210> SEQ ID NO 57
<211> LENGTH: 524
<212> TYPE: PRT
<213> ORGANISM: Artificial Sequence
<220> FEATURE:
<223> OTHER INFORMATION: Sequence of the secreted PpmA::PA fusion
      protein
<220> FEATURE:
<221> NAME/KEY: SITE
<222> LOCATION: (5)..(297)
<223> OTHER INFORMATION: Amino acids from Ppma - Streptococcus
      pneumoniae
<220> FEATURE:
<221> NAME/KEY: SITE
<222> LOCATION: (298)..(524)
<223> OTHER INFORMATION: Amino acids from protein anchor AcmA -
      Lactococcus lactis

<400> SEQUENCE: 57

Asp Thr Asn Ser Met Ser Lys Gly Ser Glu Gly Ala Asp Leu Ile Ser
1               5                   10                  15

Met Lys Gly Asp Val Ile Thr Glu His Gln Phe Tyr Glu Gln Val Lys
            20                  25                  30

Ser Asn Pro Ser Ala Gln Gln Val Leu Leu Asn Met Thr Ile Gln Lys
        35                  40                  45

Val Phe Glu Lys Gln Tyr Gly Ser Glu Leu Asp Asp Lys Glu Val Asp
    50                  55                  60

Asp Thr Ile Ala Glu Glu Lys Lys Gln Tyr Gly Glu Asn Tyr Gln Arg
65                  70                  75                  80

Val Leu Ser Gln Ala Gly Met Thr Leu Glu Thr Arg Lys Ala Gln Ile
                85                  90                  95

Arg Thr Ser Lys Leu Val Glu Leu Ala Val Lys Lys Val Ala Glu Ala
            100                 105                 110

Glu Leu Thr Asp Glu Ala Tyr Lys Lys Ala Phe Asp Glu Tyr Thr Pro
        115                 120                 125

Asp Val Thr Ala Gln Ile Ile Arg Leu Asn Asn Glu Asp Lys Ala Lys
    130                 135                 140

Glu Val Leu Glu Lys Ala Lys Ala Glu Gly Ala Asp Phe Ala Gln Leu
145                 150                 155                 160

Ala Lys Asp Asn Ser Thr Asp Glu Lys Thr Lys Glu Asn Gly Gly Glu
                165                 170                 175

Ile Thr Phe Asp Ser Ala Ser Thr Glu Val Pro Glu Gln Val Lys Lys
            180                 185                 190

Ala Ala Phe Ala Leu Asp Val Asp Gly Val Ser Asp Val Ile Thr Ala
        195                 200                 205
```

```
Thr Gly Thr Gln Ala Tyr Ser Ser Gln Tyr Tyr Ile Val Lys Leu Thr
    210                 215                 220

Lys Lys Thr Glu Lys Ser Ser Asn Ile Asp Asp Tyr Lys Glu Lys Leu
225                 230                 235                 240

Lys Thr Val Ile Leu Thr Gln Lys Gln Asn Asp Ser Thr Phe Val Gln
                245                 250                 255

Ser Ile Ile Gly Lys Glu Leu Gln Ala Ala Asn Ile Lys Val Lys Asp
            260                 265                 270

Gln Ala Phe Gln Asn Ile Phe Thr Gln Tyr Ile Gly Gly Gly Asp Ser
        275                 280                 285

Ser Ser Ser Ser Ser Thr Ser Asn Glu Ala Ile Arg Ala Pro Ser Thr
290                 295                 300

Ser Ser Gly Asn Thr Asn Ser Gly Gly Ser Thr Thr Ile Thr Asn
305                 310                 315                 320

Asn Asn Ser Gly Thr Asn Ser Ser Ser Thr Thr Tyr Thr Val Lys Ser
                325                 330                 335

Gly Asp Thr Leu Trp Gly Ile Ser Gln Arg Tyr Gly Ile Ser Val Ala
            340                 345                 350

Gln Ile Gln Ser Ala Asn Asn Leu Lys Ser Thr Ile Ile Tyr Ile Gly
        355                 360                 365

Gln Lys Leu Val Leu Thr Gly Ser Ala Ser Ser Thr Asn Ser Gly Gly
    370                 375                 380

Ser Asn Asn Ser Ala Ser Thr Thr Pro Thr Thr Ser Val Thr Pro Ala
385                 390                 395                 400

Lys Pro Thr Ser Gln Thr Thr Val Lys Val Lys Ser Gly Asp Thr Leu
                405                 410                 415

Trp Ala Leu Ser Val Lys Tyr Lys Thr Ser Ile Ala Gln Leu Lys Ser
            420                 425                 430

Trp Asn His Leu Ser Ser Asp Thr Ile Tyr Ile Gly Gln Asn Leu Ile
        435                 440                 445

Val Ser Gln Ser Ala Ala Ala Ser Asn Pro Ser Thr Gly Ser Gly Ser
    450                 455                 460

Thr Ala Thr Asn Asn Ser Asn Ser Thr Ser Ser Asn Ser Asn Ala Ser
465                 470                 475                 480

Ile His Lys Val Val Lys Gly Asp Thr Leu Trp Gly Leu Ser Gln Lys
                485                 490                 495

Ser Gly Ser Pro Ile Ala Ser Ile Lys Ala Trp Asn His Leu Ser Ser
            500                 505                 510

Asp Thr Ile Leu Ile Gly Gln Tyr Leu Arg Ile Lys
        515                 520

<210> SEQ ID NO 58
<211> LENGTH: 891
<212> TYPE: PRT
<213> ORGANISM: Artificial Sequence
<220> FEATURE:
<223> OTHER INFORMATION: Sequence of the secreted Iga1prt::PA fusion
      protein
<220> FEATURE:
<221> NAME/KEY: SITE
<222> LOCATION: (6)..(665)
<223> OTHER INFORMATION: Amino acids from Igaprt1 - Streptococcus
      pneumoniae
<220> FEATURE:
<221> NAME/KEY: SITE
<222> LOCATION: (666)..(891)
<223> OTHER INFORMATION: Amino acids from protein anchor AcmA -
      Lactococcus lactis
```

-continued

<400> SEQUENCE: 58

```
Asp Thr Asn Ser Met Gly Gln Thr Glu Pro Glu Pro Ser Asn Gly Asn
1               5                   10                  15

Ser Thr Glu Asp Val Ser Thr Glu Ser Asn Thr Ser Asn Ser Asn Gly
            20                  25                  30

Asn Glu Glu Ile Lys Gln Glu Asn Glu Leu Asp Pro Asp Lys Lys Val
        35                  40                  45

Glu Glu Pro Glu Lys Thr Leu Glu Leu Arg Asn Val Ser Asp Leu Glu
    50                  55                  60

Leu Tyr Ser Leu Ser Asn Gly Thr Tyr Lys Gln His Ile Ser Leu Glu
65                  70                  75                  80

Gln Val Pro Ser Asn Pro Asn Ser Tyr Phe Val Lys Val Lys Ser Ser
                85                  90                  95

Ser Phe Lys Asp Val Tyr Leu Pro Val Ala Ser Ile Ser Glu Glu Arg
            100                 105                 110

Lys Asn Asp Lys Ile Leu Tyr Lys Ile Thr Ala Lys Val Glu Lys Leu
        115                 120                 125

Gln Gln Glu Ile Glu Ser Arg Tyr Lys Asp Asn Phe Thr Phe Tyr Leu
    130                 135                 140

Ala Lys Lys Gly Thr Glu Glu Thr Asn Phe Thr Ser Phe Ser Asn
145                 150                 155                 160

Leu Val Lys Ala Ile Asn Gln Asn Pro Ser Thr Tyr His Leu Ala
                165                 170                 175

Ala Ser Leu Asn Ala Asn Glu Val Glu Leu Gly Pro Asp Glu Arg Ser
            180                 185                 190

Tyr Ile Lys Asp Thr Phe Thr Gly Arg Leu Ile Gly Glu Lys Asp Gly
        195                 200                 205

Lys Asn Tyr Ala Ile Tyr Asn Leu Lys Lys Pro Leu Phe Glu Asn Leu
    210                 215                 220

Ser Gly Ala Thr Val Glu Lys Leu Ser Leu Lys Asn Val Ala Ile Ser
225                 230                 235                 240

Gly Lys Asp Asp Ile Gly Ser Leu Ala Asn Glu Ala Gln Asn Asn Thr
                245                 250                 255

Lys Ile Lys Gln Val His Val Asp Gly Val Leu Ala Gly Glu Arg Gly
            260                 265                 270

Ile Gly Gly Leu Leu Ala Lys Ala Glu Gln Ser Ser Ile Thr Glu Ser
        275                 280                 285

Ser Phe Lys Gly Arg Ile Ile Asn Thr Tyr Glu Thr Thr Ala Ala Tyr
    290                 295                 300

Asn Ile Gly Gly Met Val Gly His Leu Thr Gly Asp Lys Ala Leu Leu
305                 310                 315                 320

Thr Lys Ser Lys Ala Thr Val Ala Ile Ser Ser Asn Thr Asn Thr Ser
                325                 330                 335

Asp Gln Thr Val Gly Leu Ala Gly Leu Val Asp Arg Asp Ala Gln
            340                 345                 350

Ile Gln Asp Ser Tyr Ala Glu Gly Asp Ile Asn Asn Val Lys His Phe
        355                 360                 365

Gly Arg Val Ala Gly Val Ala Gly Asn Leu Trp Asp Arg Thr Ser Gly
    370                 375                 380

Asp Val Arg His Ala Gly Ser Leu Thr Asn Val Leu Ser Asp Val Asn
385                 390                 395                 400

Val Thr Asn Gly Asn Ala Ile Thr Gly Tyr His Tyr Asn Glu Met Lys
                405                 410                 415
```

```
Val Lys Asp Thr Phe Ser Ser Lys Ala Asn Arg Val Tyr Asn Val Thr
                420                 425                 430

Leu Val Lys Asp Glu Val Val Ser Lys Glu Ser Phe Glu Arg Gly
            435                 440                 445

Thr Met Leu Asp Ala Ser Gln Ile Ala Ser Lys Lys Ala Glu Ile Asn
450                 455                 460

Pro Leu Ile Leu Pro Thr Val Glu Pro Leu Ser Thr Ser Gly Lys Lys
465                 470                 475                 480

Asp Ser Asp Phe Ser Lys Val Ala Tyr Tyr Gln Ala Lys Arg Asn Leu
                485                 490                 495

Thr Tyr Lys Asn Ile Glu Lys Leu Leu Pro Phe Tyr Asn Lys Ala Thr
                500                 505                 510

Ile Val Lys Tyr Gly Asn Leu Val Asn Glu Asn Ser Leu Leu Tyr Gln
                515                 520                 525

Lys Glu Leu Leu Ser Ala Val Met Met Lys Asp Asn Gln Val Ile Thr
530                 535                 540

Asp Ile Val Ser Asn Lys Gln Thr Ala Asn Lys Leu Leu Leu His Tyr
545                 550                 555                 560

Lys Asp Asp Leu Ser Glu Lys Leu Asp Leu Lys Tyr Gln Asn Asp Phe
                565                 570                 575

Ala Lys Leu Ala Glu Tyr Ser Leu Gly Asn Thr Gly Leu Leu Tyr Thr
                580                 585                 590

Pro Asn Gln Phe Leu Tyr Asp Gln Thr Ser Ile Ile Lys Gln Val Leu
                595                 600                 605

Pro Asp Leu Gln Lys Val Asp Tyr His Ser Glu Ala Ile Arg Lys Thr
610                 615                 620

Leu Gly Ile Ser Pro Asn Val Lys Gln Thr Glu Leu Tyr Leu Glu Asp
625                 630                 635                 640

Gln Phe Ala Lys Thr Lys Gln Gln Leu Glu Asp Ser Leu Lys Lys Leu
                645                 650                 655

Leu Ser Ala Asp Ala Gly Leu Ala Arg Ile Arg Ala Pro Ser Thr Ser
                660                 665                 670

Ser Gly Asn Thr Asn Ser Gly Gly Ser Thr Thr Ile Thr Asn Asn
                675                 680                 685

Asn Ser Gly Thr Asn Ser Ser Thr Thr Tyr Thr Val Lys Ser Gly
690                 695                 700

Asp Thr Leu Trp Gly Ile Ser Gln Arg Tyr Gly Ile Ser Val Ala Gln
705                 710                 715                 720

Ile Gln Ser Ala Asn Asn Leu Lys Ser Thr Ile Ile Tyr Ile Gly Gln
                725                 730                 735

Lys Leu Val Leu Thr Gly Ser Ala Ser Ser Thr Asn Ser Gly Gly Ser
                740                 745                 750

Asn Asn Ser Ala Ser Thr Thr Pro Thr Thr Ser Val Thr Pro Ala Lys
                755                 760                 765

Pro Thr Ser Gln Thr Thr Val Lys Val Lys Ser Gly Asp Thr Leu Trp
                770                 775                 780

Ala Leu Ser Val Lys Tyr Lys Thr Ser Ile Ala Gln Leu Lys Ser Trp
785                 790                 795                 800

Asn His Leu Ser Ser Asp Thr Ile Tyr Ile Gly Gln Asn Leu Ile Val
                805                 810                 815

Ser Gln Ser Ala Ala Ala Ser Asn Pro Ser Thr Gly Ser Gly Ser Thr
                820                 825                 830

Ala Thr Asn Asn Ser Asn Ser Thr Ser Ser Asn Ser Asn Ala Ser Ile
                835                 840                 845
```

```
His Lys Val Val Lys Gly Asp Thr Leu Trp Gly Leu Ser Gln Lys Ser
        850                 855                 860

Gly Ser Pro Ile Ala Ser Ile Lys Ala Trp Asn His Leu Ser Ser Asp
865                 870                 875                 880

Thr Ile Leu Ile Gly Gln Tyr Leu Arg Ile Lys
                885                 890

<210> SEQ ID NO 59
<211> LENGTH: 479
<212> TYPE: PRT
<213> ORGANISM: Artificial Sequence
<220> FEATURE:
<223> OTHER INFORMATION: Sequence of the secreted SlrA::PA fusion
      protein
<220> FEATURE:
<221> NAME/KEY: SITE
<222> LOCATION: (6)..(252)
<223> OTHER INFORMATION: Amino acids from SlrA - Streptococcus
      pneumoniae
<220> FEATURE:
<221> NAME/KEY: SITE
<222> LOCATION: (253)..(479)
<223> OTHER INFORMATION: Amino acids from protein anchor AcmA -
      Lactococcus lactis

<400> SEQUENCE: 59

Asp Thr Asn Ser Met Val Gln Arg Ser Leu Arg Gly Asp Asp Tyr Val
1               5                   10                  15

Asp Ser Ser Leu Ala Ala Glu Glu Ser Ser Lys Val Ala Ala Gln Ser
            20                  25                  30

Ala Lys Glu Leu Asn Asp Ala Leu Thr Asn Glu Asn Ala Asn Phe Pro
        35                  40                  45

Gln Leu Ser Lys Glu Val Ala Glu Asp Glu Ala Glu Val Ile Phe His
    50                  55                  60

Thr Ser Gln Gly Asp Ile Arg Ile Lys Leu Phe Pro Lys Leu Ala Pro
65                  70                  75                  80

Leu Ala Val Glu Asn Phe Leu Thr His Ala Lys Glu Gly Tyr Tyr Asn
                85                  90                  95

Gly Ile Thr Phe His Arg Val Ile Asp Gly Phe Met Val Gln Thr Gly
            100                 105                 110

Asp Pro Lys Gly Asp Gly Thr Gly Gln Ser Ile Trp His Asp Lys
        115                 120                 125

Asp Lys Thr Lys Asp Lys Gly Thr Gly Phe Lys Asn Glu Ile Thr Pro
130                 135                 140

Tyr Leu Tyr Asn Ile Arg Gly Ala Leu Ala Met Ala Asn Thr Gly Gln
145                 150                 155                 160

Pro Asn Thr Asn Gly Ser Gln Phe Phe Ile Asn Gln Asn Ser Thr Asp
                165                 170                 175

Thr Ser Ser Lys Leu Pro Thr Ser Lys Tyr Pro Gln Lys Ile Ile Glu
            180                 185                 190

Ala Tyr Lys Glu Gly Gly Asn Pro Ser Leu Asp Gly Lys His Pro Val
        195                 200                 205

Phe Gly Gln Val Ile Asp Gly Met Asp Val Val Asp Lys Ile Ala Lys
    210                 215                 220

Ala Glu Lys Asp Glu Lys Asp Lys Pro Thr Thr Ala Ile Thr Ile Asp
225                 230                 235                 240

Ser Ile Glu Val Val Lys Asp Tyr Asp Phe Lys Ser Gly Ile Arg Ala
                245                 250                 255

Pro Ser Thr Ser Ser Gly Asn Thr Asn Ser Gly Gly Ser Thr Thr Thr
```

```
                260              265                270
Ile Thr Asn Asn Ser Gly Thr Asn Ser Ser Ser Thr Tyr Thr
        275                 280             285
Val Lys Ser Gly Asp Thr Leu Trp Gly Ile Ser Gln Arg Tyr Gly Ile
290                 295                 300
Ser Val Ala Gln Ile Gln Ser Ala Asn Asn Leu Lys Ser Thr Ile Ile
305                 310                 315                 320
Tyr Ile Gly Gln Lys Leu Val Leu Thr Gly Ser Ala Ser Ser Thr Asn
                325                 330                 335
Ser Gly Gly Ser Asn Asn Ser Ala Ser Thr Thr Pro Thr Thr Ser Val
                340                 345                 350
Thr Pro Ala Lys Pro Thr Ser Gln Thr Thr Val Lys Val Lys Ser Gly
                355                 360                 365
Asp Thr Leu Trp Ala Leu Ser Val Lys Tyr Lys Thr Ser Ile Ala Gln
        370                 375                 380
Leu Lys Ser Trp Asn His Leu Ser Ser Asp Thr Ile Tyr Ile Gly Gln
385                 390                 395                 400
Asn Leu Ile Val Ser Gln Ser Ala Ala Ala Ser Asn Pro Ser Thr Gly
                405                 410                 415
Ser Gly Ser Thr Ala Thr Asn Asn Ser Asn Ser Thr Ser Ser Asn Ser
                420                 425                 430
Asn Ala Ser Ile His Lys Val Val Lys Gly Asp Thr Leu Trp Gly Leu
                435                 440                 445
Ser Gln Lys Ser Gly Ser Pro Ile Ala Ser Ile Lys Ala Trp Asn His
        450                 455                 460
Leu Ser Ser Asp Thr Ile Leu Ile Gly Gln Tyr Leu Arg Ile Lys
465                 470                 475

<210> SEQ ID NO 60
<211> LENGTH: 49
<212> TYPE: DNA
<213> ORGANISM: Artificial sequence
<220> FEATURE:
<223> OTHER INFORMATION: Primer

<400> SEQUENCE: 60
ccatggctag ccaccatcac catcaccatt cgaaagggtc agaaggtgc          49

<210> SEQ ID NO 61
<211> LENGTH: 30
<212> TYPE: DNA
<213> ORGANISM: Artificial sequence
<220> FEATURE:
<223> OTHER INFORMATION: Primer

<400> SEQUENCE: 61
tcatggatcc ggactattcg tttgatgtac                              30

<210> SEQ ID NO 62
<211> LENGTH: 659
<212> TYPE: PRT
<213> ORGANISM: Artificial Sequence
<220> FEATURE:
<223> OTHER INFORMATION: Amino acids from Igaprt1 - Streptococcus
      pneumoniae

<400> SEQUENCE: 62

Gly Gln Thr Glu Pro Glu Pro Ser Asn Gly Asn Ser Thr Glu Asp Val
1               5                   10                  15

Ser Thr Glu Ser Asn Thr Ser Asn Ser Asn Gly Asn Glu Glu Ile Lys
```

-continued

```
                20                  25                  30
Gln Glu Asn Glu Leu Asp Pro Asp Lys Lys Val Glu Glu Pro Glu Lys
         35                  40                  45

Thr Leu Glu Leu Arg Asn Val Ser Asp Leu Glu Leu Tyr Ser Leu Ser
 50                  55                  60

Asn Gly Thr Tyr Lys Gln His Ile Ser Leu Glu Gln Val Pro Ser Asn
 65                  70                  75                  80

Pro Asn Ser Tyr Phe Val Lys Val Lys Ser Ser Phe Lys Asp Val
                 85                  90                  95

Tyr Leu Pro Val Ala Ser Ile Ser Glu Glu Arg Lys Asn Asp Lys Ile
                100                 105                 110

Leu Tyr Lys Ile Thr Ala Lys Val Glu Lys Leu Gln Gln Glu Ile Glu
                115                 120                 125

Ser Arg Tyr Lys Asp Asn Phe Thr Phe Tyr Leu Ala Lys Lys Gly Thr
         130                 135                 140

Glu Glu Thr Thr Asn Phe Thr Ser Phe Ser Asn Leu Val Lys Ala Ile
145                 150                 155                 160

Asn Gln Asn Pro Ser Gly Thr Tyr His Leu Ala Ala Ser Leu Asn Ala
                165                 170                 175

Asn Glu Val Glu Leu Gly Pro Asp Glu Arg Ser Tyr Ile Lys Asp Thr
                180                 185                 190

Phe Thr Gly Arg Leu Ile Gly Glu Lys Asp Gly Lys Asn Tyr Ala Ile
                195                 200                 205

Tyr Asn Leu Lys Lys Pro Leu Phe Glu Asn Leu Ser Gly Ala Thr Val
         210                 215                 220

Glu Lys Leu Ser Leu Lys Asn Val Ala Ile Ser Gly Lys Asp Asp Ile
225                 230                 235                 240

Gly Ser Leu Ala Asn Glu Ala Gln Asn Asn Thr Lys Ile Lys Gln Val
                245                 250                 255

His Val Asp Gly Val Leu Ala Gly Glu Arg Gly Ile Gly Gly Leu Leu
                260                 265                 270

Ala Lys Ala Glu Gln Ser Ser Ile Thr Glu Ser Ser Phe Lys Gly Arg
         275                 280                 285

Ile Ile Asn Thr Tyr Glu Thr Thr Ala Ala Tyr Asn Ile Gly Gly Met
290                 295                 300

Val Gly His Leu Thr Gly Asp Lys Ala Leu Leu Thr Lys Ser Lys Ala
305                 310                 315                 320

Thr Val Ala Ile Ser Ser Asn Thr Asn Thr Ser Asp Gln Thr Val Gly
                325                 330                 335

Gly Leu Ala Gly Leu Val Asp Arg Asp Ala Gln Ile Gln Asp Ser Tyr
                340                 345                 350

Ala Glu Gly Asp Ile Asn Asn Val Lys His Phe Gly Arg Val Ala Gly
         355                 360                 365

Val Ala Gly Asn Leu Trp Asp Arg Thr Ser Gly Asp Val Arg His Ala
         370                 375                 380

Gly Ser Leu Thr Asn Val Leu Ser Asp Val Asn Val Thr Asn Gly Asn
385                 390                 395                 400

Ala Ile Thr Gly Tyr His Tyr Asn Glu Met Lys Val Lys Asp Thr Phe
                405                 410                 415

Ser Ser Lys Ala Asn Arg Val Tyr Asn Val Thr Leu Val Lys Asp Glu
         420                 425                 430

Val Val Ser Lys Glu Ser Phe Glu Glu Arg Gly Thr Met Leu Asp Ala
         435                 440                 445
```

-continued

```
Ser Gln Ile Ala Ser Lys Lys Ala Glu Ile Asn Pro Leu Ile Leu Pro
        450             455             460

Thr Val Glu Pro Leu Ser Thr Ser Gly Lys Lys Asp Ser Asp Phe Ser
465             470             475             480

Lys Val Ala Tyr Tyr Gln Ala Lys Arg Asn Leu Thr Tyr Lys Asn Ile
                485             490             495

Glu Lys Leu Leu Pro Phe Tyr Asn Lys Ala Thr Ile Val Lys Tyr Gly
            500             505             510

Asn Leu Val Asn Glu Asn Ser Leu Leu Tyr Gln Lys Glu Leu Leu Ser
        515             520             525

Ala Val Met Met Lys Asp Asn Gln Val Ile Thr Asp Ile Val Ser Asn
        530             535             540

Lys Gln Thr Ala Asn Lys Leu Leu Leu His Tyr Lys Asp Asp Leu Ser
545             550             555             560

Glu Lys Leu Asp Leu Lys Tyr Gln Asn Asp Phe Ala Lys Leu Ala Glu
            565             570             575

Tyr Ser Leu Gly Asn Thr Gly Leu Leu Tyr Thr Pro Asn Gln Phe Leu
            580             585             590

Tyr Asp Gln Thr Ser Ile Ile Lys Gln Val Leu Pro Asp Leu Gln Lys
        595             600             605

Val Asp Tyr His Ser Glu Ala Ile Arg Lys Thr Leu Gly Ile Ser Pro
        610             615             620

Asn Val Lys Gln Thr Glu Leu Tyr Leu Glu Asp Gln Phe Ala Lys Thr
625             630             635             640

Lys Gln Gln Leu Glu Asp Ser Leu Lys Lys Leu Leu Ser Ala Asp Ala
            645             650             655

Gly Leu Ala
```

The invention claimed is:

1. A composition for inducing an immune response to infection by *Streptococcus pneumoniae*, comprising at least an antigenic part of pneumococcal maturation protein A (PpmA), at least an antigenic part of streptococcal lipoprotein rotamase A (SlrA), and SEQ ID NO: 62.

2. The composition according to claim 1, further comprising a pharmaceutically acceptable carrier and/or adjuvant.

3. The composition according to claim 2, wherein said adjuvant is obtained from bacterial cell wall material.

4. The composition according to claim 2, wherein said adjuvant is a ghost.

5. The composition according to claim 4, wherein said ghost is a ghost from *Lactococcus lactis*.

6. The composition according to claim 1, wherein said protein is coupled to a ghost.

7. The composition according to claim 6, wherein said ghost is a ghost from *Lactococcus lactis*.

8. The composition according to claim 6, wherein said coupling is effected by a protein anchor.

9. The composition according to claim 8, wherein said protein anchor is AcmA.

10. A method for treating an infection by *Streptococcus pneumoniae* comprising administering to a mammal in need thereof a composition, said composition comprises at least an antigenic part of pneumococcal maturation protein A (PpmA), at least an antigenic part of streptococcal lipoprotein rotamase A (SlrA), and SEQ ID NO: 62.

11. A method for inducing an immune response to infection by *Streptococcus pneumoniae* comprising administering to a mammal in need thereof a composition, said composition comprises at least an antigenic part of pneumococcal maturation protein A (PpmA), at least an antigenic part of streptococcal lipoprotein rotamase A (SlrA), and SEQ ID NO: 62.

12. A method according to claim 11, wherein the administration is mucosal.

13. A method according to claim 11, wherein the administration is nasal.

* * * * *

UNITED STATES PATENT AND TRADEMARK OFFICE
CERTIFICATE OF CORRECTION

| | | |
|---|---|---|
| PATENT NO. | : 8,142,789 B2 | Page 1 of 1 |
| APPLICATION NO. | : 10/556733 | |
| DATED | : March 27, 2012 | |
| INVENTOR(S) | : Leenhouts et al. | |

It is certified that error appears in the above-identified patent and that said Letters Patent is hereby corrected as shown below:

IN THE SPECIFICATION:

Column 4, line 1

Now reads:      "The numbers is subscript";

Should read:      -- The numbers in subscript --.

Column 5, line 42

Now reads:      "comprises co-called ghosts";

Should read:      -- comprises so-called ghosts --.

Column 14, line 20

Now reads:      "then be bred to produce";

Should read:      -- then bred to produce --.

Column 25, line 29

Now reads:      "active peptide of SirA was";

Should read:      -- active peptide of SlrA was --.

Column 32, line 15

Now reads:      "N-terminal His6 tag.";

Should read:      -- N-terminal $His_6$ tag. --.

Column 32, line 24

Now reads:      "free dried, and stored at";

Should read:      -- freeze dried, and stored at --.

Signed and Sealed this
Fifth Day of November, 2013

Teresa Stanek Rea
*Deputy Director of the United States Patent and Trademark Office*